(12) United States Patent
Seibel et al.

(10) Patent No.: US 11,279,963 B2
(45) Date of Patent: Mar. 22, 2022

(54) GLYCOSYLATED MONO(2-HYDROXYETHYL) TEREPHTHALIC ACID AND GLYCOSYLATED BIS(2-HYDROXYETHYL) TEREPHTHALIC ACID

(71) Applicant: Julius-Maximilians-Universität Würzburg, Wurzbürg (DE)

(72) Inventors: Jürgen Seibel, Würzburg (DE); Malte Timm, Gerbrunn (DE)

(73) Assignee: Julius-Maximilians-Universität Würzburg, Wurzbürg (DE)

( * ) Notice: Subject to any disclaimer, the term of this patent is extended or adjusted under 35 U.S.C. 154(b) by 477 days.

(21) Appl. No.: 16/087,334

(22) PCT Filed: Mar. 23, 2017

(86) PCT No.: PCT/EP2017/056995
§ 371 (c)(1),
(2) Date: Sep. 21, 2018

(87) PCT Pub. No.: WO2017/162825
PCT Pub. Date: Sep. 28, 2017

(65) Prior Publication Data
US 2020/0332334 A1    Oct. 22, 2020

(30) Foreign Application Priority Data

Mar. 23, 2016 (EP) ..................... 16000698
Jul. 8, 2016 (EP) ..................... 16001525
Aug. 5, 2016 (EP) ..................... 16001744

(51) Int. Cl.
*C07H 15/18* (2006.01)
*C12P 19/44* (2006.01)

(52) U.S. Cl.
CPC .............. *C12P 19/44* (2013.01); *C07H 15/18* (2013.01); *C12Y 301/01* (2013.01); *C12Y 302/0102* (2013.01); *C12Y 302/0108* (2013.01); *C12Y 302/01021* (2013.01); *C12Y 302/01023* (2013.01)

(58) Field of Classification Search
None
See application file for complete search history.

(56) References Cited

U.S. PATENT DOCUMENTS 6,037,447 A  *  3/2000  Stack ..................... C07K 9/008
                                                          530/317

FOREIGN PATENT DOCUMENTS

DE           1058666 A      6/1959
WO    WO 2015-025861 A1    2/2015

OTHER PUBLICATIONS

PCT/EP2017/056995, Aug. 21, 2017, International Search Report and Written Opinion.
International Search Report and Written Opinion dated Aug. 21, 2017 in connection with PCT/EP2017/056995.
Barth et al., A dual enzyme system composed of a polyester hydrolase and a carboxylesterase enhances the biocatalytic degradation of polyethylene terephthalate films. Biotechnol J. Aug. 2016;11(8):1082-7. doi: 10.1002/biot.201600008. Epub Jun. 21, 2016.
Bornscheuer et al., Microbiology. Feeding on plastic. Science. Mar. 11, 2016;351(6278):1154-5. doi: 10.1126/science.aaf2853.
Carniel et al., Lipase from Candida antarctica (CALB) and cutinase from Humicola insolens act synergistically for PET hydrolysis to terephthalic acid. Accepted Manuscript. Proces Biochem. Aug. 2017;59(A):84-90. doi: https://doi.org/10.1016/j.procbio.2016.07.023.
Database Registry UniProt [Online]: Database Accession No. A0A0K8P6T7; Yoshida et al., XP002771141, Feb. 17, 2016; 1 page.
Database Registry UniProt [Online]: Database Accession No. A0A0K8P3N6; Yoshida et al., XP002771142, Mar. 16, 2016; 1 page.
Fujiwara et al., Purification, characterization, and molecular analysis of the gene encoding glucosyltransferase from Streptococcus oralis. Infect Immun. May 2000;68(5):2475-83.
Kren, Glycosidases in Synthesis of Glycomimetics and Unnatural Carbohydrates. Synthesis and Biological Applications of Glycoconjugates. 2011:229.
Yoshida et al., A bacterium that degrades and assimilates poly(ethylene terephthalate). Science. Mar. 11, 2016;351(6278):1196-9. doi: 10.1126/science.aad6359.
Kren, Glycosidases in synthesis of glycomimetics and unnatural carbohydrates. Synthesis Biological Applications Glycoconjugates. 2011:226-239.
Brooke et al., The synthesis of oligomers related to poly(ethyleneglycol terephthalate). Polymer. 2002;43(4):1139-1154.

* cited by examiner

*Primary Examiner* — Layla D Berry
(74) *Attorney, Agent, or Firm* — Wolf, Greenfield & Sacks, P.C.

(57) ABSTRACT

The invention concerns a compound characterised by a mono(2-hydroxyethyl) terephthalic acid (MHET) and bis(2-hydroxyethyl) terephthalic acid chemically bonded to a saccharide. Furthermore, the invention concerns a corresponding compound which is used as a synthesis component for polymers or fine chemicals.

16 Claims, 47 Drawing Sheets

Specification includes a Sequence Listing.

GLYCOSYLATED MONO(2-HYDROXYETHYL) TEREPHTHALIC ACID AND GLYCOSYLATED BIS(2-HYDROXYETHYL) TEREPHTHALIC ACID

CROSS REFERENCE TO RELATED APPLICATION(S)

This Application is a National Stage filing under 35 U.S.C. 371 of International Patent Application Serial No. PCT/EP2017/056995, filed Mar. 23, 2017, and claims priority to European Application No. 16000698.7, filed Mar. 23, 2016; European Application No. 16001525.1, filed Jul. 8, 2016; and European Application No. 16001744.8, filed Aug. 5, 2016. The entire contents of these applications are incorporated herein by reference in their entirety.

FIELD OF THE INVENTION

The invention concerns a compound containing mono(2-hydroxyethyl) terephthalic acid or bis(2-hydroxyethyl) terephthalic acid, which is used as a fine chemical, active ingredient or starting material for biohybrid polymers.

PRIOR ART

S. Yoshida et. al reported on the bacterial strain *I. sakaiensis*. It is able to attach to and degrade polyethylene terephthalate (abbreviation PET), a thermoplastic material from the polyester family produced by polycondensation. The enzyme PETase is released from the bacterial strain, it hydrolyses PET and produces mono(2-hydroxyethyl) terephthalic acid (MHET) (FIG. 1) (Lit. S. Yoshida et. al. *Science* 351, 1196 (2016); U. Bornscheuer, *Science* 351, 1154 (2016). In a further step MHET is hydrolysed to the monomers ethylene glycol and terephthalic acid.

DESCRIPTION OF THE INVENTION

PET is used for the production of plastic bottles (PET bottles), films, textile fibres and the like. Worldwide production is 40 million tons per year. Up to now, it has been difficult to break down PET into usable substances or to use it for synthesis.

This object is achieved according to the invention by glycosylation of the substance mono(2-hydroxyethyl) terephthalic acid (MHET) and glycosylation of the substance bis(2-hydroxyethyl) terephthalic acid (BHET).

The advantage of this invention is that it makes it possible to produce new chemical compounds from waste and degradation products from PET production. These chemical compounds comprise glycosylated mono(2-hydroxyethyl) terephthalic acid (MHET) or glycosylated bis(2-hydroxyethyl) terephthalic acid (BHET). These chemical compounds can be used advantageously in various ways, for example as fine chemicals, active ingredients or biopolymers. Thus, the invention makes it possible to produce new chemicals from PET waste and degradation products.

Another advantageous aspect of the invention is that the glycosylation of mono(2-hydroxyethyl) terephthalic acid (MHET) or bis(2-hydroxyethyl) terephthalic acid (BHET) and the other optional method steps of the invention can be carried out almost completely enzymatically.

In addition, glycosylated compounds according to the invention have advantageous surface properties. Due to these properties, the compounds can be used in many ways according to the invention, for example as cell culture substrates.

In addition, according to the invention, the glycosylation of the compounds of the present invention promotes their biodegradability and biocompatibility. For this reason the compounds according to the invention can be used advantageously in medical applications, especially in biomedical applications.

The present invention thus provides the following preferred embodiments:

Preferred Embodiments

1. Compound comprising glycosylated mono(2-hydroxyethyl) terephthalic acid (MHET) or glycosylated bis(2-hydroxyethyl) terephthalic acid (BHET).
2. The compound according to Embodiment 1, wherein the MHET or BHET and a saccharide are chemically bonded to each other via a glycosidic bond.
3. Compound comprising mono(2-hydroxyethyl) terephthalic acid (MHET) or bis(2-hydroxyethyl) terephthalic acid chemically bonded to a saccharide.
4. The compound according to Embodiment 3, wherein the MHET or BHET and the saccharide are chemically bonded to each other via a glycosidic bond.
5. The compound according to at least one of Embodiments 2 to 4, wherein the saccharide is a monosaccharide or disaccharide.
6. The compound according to Embodiment 5, wherein the monosaccharide or disaccharide is selected from the group consisting of hexoses and pentoses.
7. The compound according to Embodiment 5 wherein the monosaccharide or disaccharide is selected from α-glucose, β-glucose, α-fructose, β-fructose, α-galactose and β-galactose, α-mannose and β-mannose, xylose, N-acetylglucosamine, glucosamine and glucuronic acid.
8. The compound according to at least one of Embodiments 1 to 7, wherein the compound is obtained by enzymatic glycosylation of MHET or BHET.
9. The compound according to at least one of Embodiments 1 to 8, wherein the compound is formed by enzymatic glycosylation of MHET or BHET.
10. The compound according to Embodiments 8 or 9, wherein the enzymatic glycosylation is catalysed by a glucosidase, a galactosidase or a fructosidase.
11. The compound according to Embodiment 10, wherein the enzymatic glycosylation is catalysed by a glucosidase.
12. The compound according to Embodiment 11, wherein the glucosidase is an α-glucosidase or a β-glucosidase.
13. The compound according to at least one of Embodiments 8 to 12, wherein the MHET or BHET is obtainable by bacterial degradation or enzymatic degradation from polyethylene terephthalate (PET).
14. The compound according to at least one of Embodiments 8 to 13, wherein the MHET or BHET is formed by bacterial degradation or enzymatic degradation from polyethylene terephthalate (PET).
15. The compound according to Embodiments 13 or 14, wherein the enzymatic degradation of PET is catalysed by a hydrolase.
16. The compound according to Embodiment 15, wherein the hydrolase PETase is from *Idionella sakaiensis*.
17. The compound according to Embodiment 15 or 16, wherein the hydrolase comprises the amino acid sequence shown in SEQ ID NO: 1.

18. The compound according to at least one of Embodiments 13 to 17, wherein the enzyme for the enzymatic glycosylation of MHET or BHET and the enzyme for the enzymatic degradation of PET are used together.
19. The compound according to Embodiment 18, wherein a microorganism containing the enzyme for enzymatic glycosylation and the enzyme for enzymatic degradation of PET is used.
20. The compound according to at least one of Embodiments 1 to 19, consisting of MHET or BHET chemically bonded to a saccharide via a glycosidic bond.
21. The compound according to at least one of Embodiments 1 to 20, wherein the compound has one of the following structures (a) or (b):

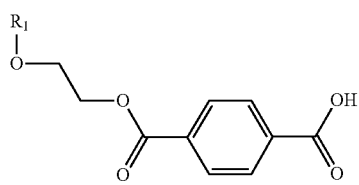

(a)

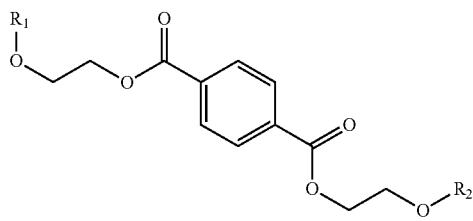

(b)

wherein $R_1$ comprises a saccharide bound via a glycosidic bond, and $R_2$ comprises a saccharide bound via a glycosidic bond or is H.

22. The compound according to at least one of Embodiments 1 to 19, wherein the compound further comprises at least one methacrylic residue.
23. The compound according to embodiment 22, wherein the compound has the following structure:

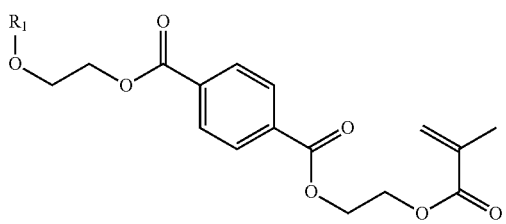

wherein $R_1$ comprises a saccharide bound via a glycosidic bond and $R_2$ comprises a methacrylic residue.

24. The compound according to embodiment 23, wherein the compound has the following structure:

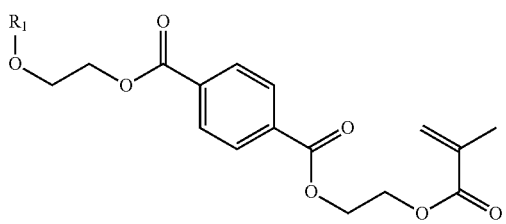

25. The compound according to embodiment 23, wherein the compound has the following structure:

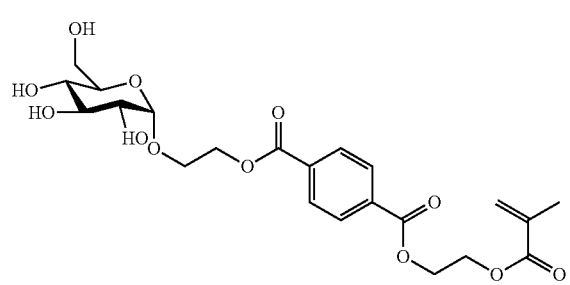

26. Compound according to embodiment 23, said compound having the following structure:

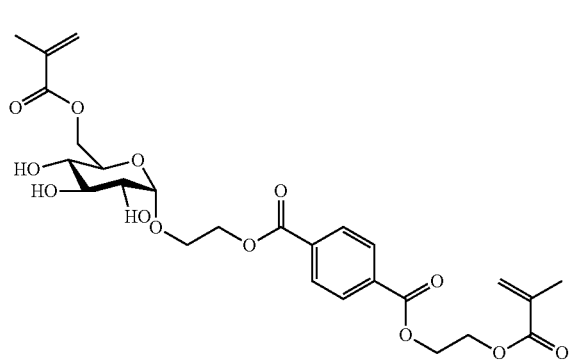

27. The compound according to at least one of Embodiments 1 to 19, wherein the compound comprises a lipophilic side chain.
28. The compound according to Embodiment 27, wherein the compound has the following structure:

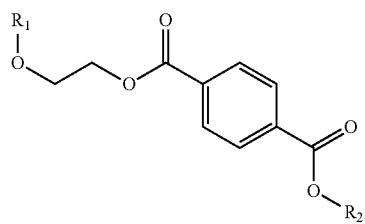

wherein $R_1$ comprises a saccharide bound via a glycosidic bond and $R_2$ comprises a lipophilic side chain, preferably a saturated or unsaturated aliphatic hydrocarbon side chain, or a linker.

29. The compound according to Embodiment 28, wherein $R_2$ is a saturated or unsaturated aliphatic $C_5$ to $C_{20}$ hydrocarbon side chain, preferably a saturated or unsaturated aliphatic $C_5$ to $C_{15}$ hydrocarbon side chain, more preferably a saturated or unsaturated aliphatic $C_8$ to $C_{12}$ hydrocarbon side chain, more preferably a saturated or unsaturated aliphatic $C_{10}$ hydrocarbon side chain and more particularly preferably a saturated aliphatic $C_{10}$ hydrocarbon side chain.

30. The compound according to Embodiment 28 selected from a compound having the following structure (a) to (j):

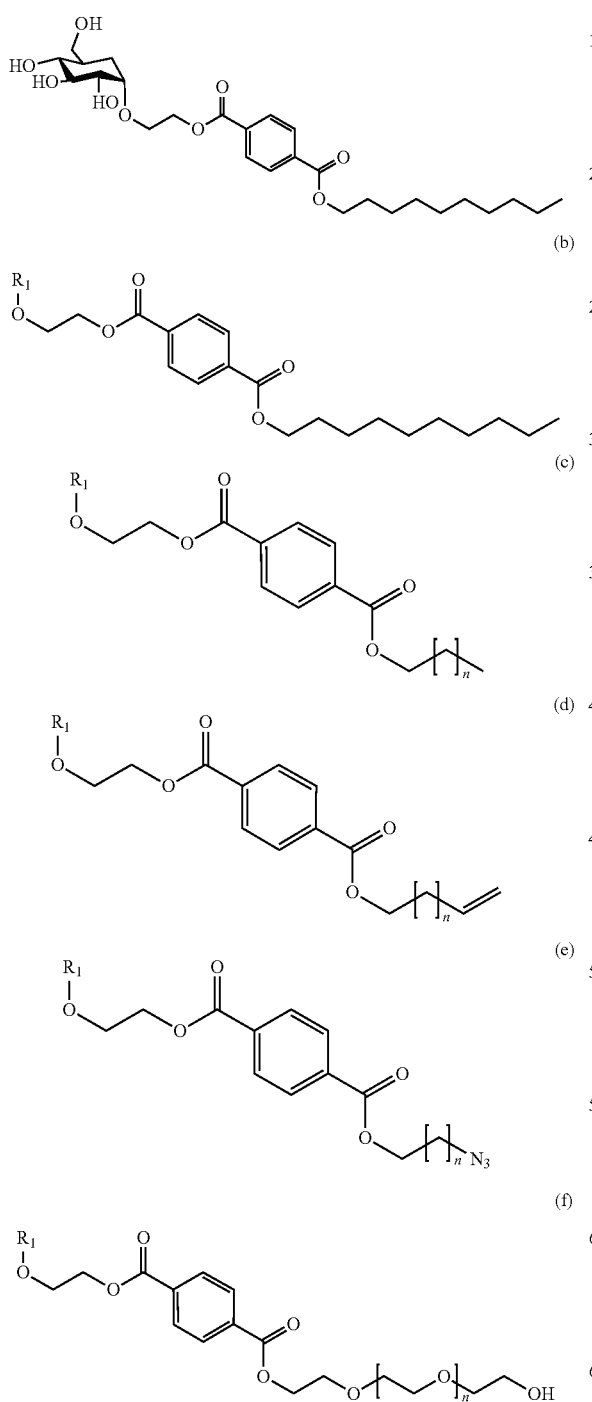

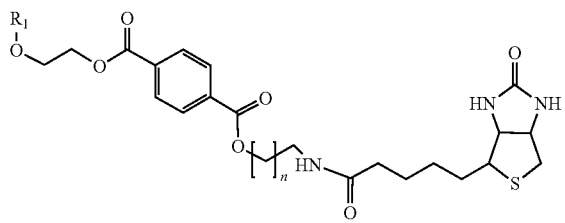

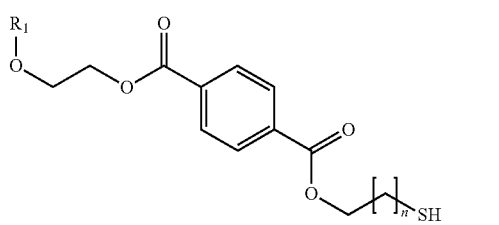

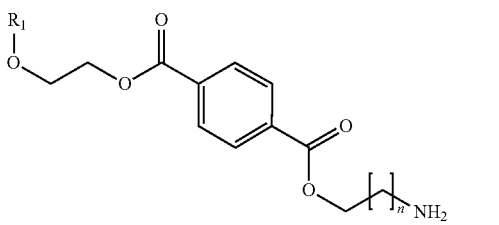

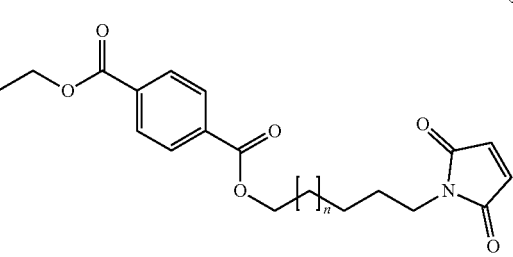

wherein n is 1, 2, 3, 4, 5, 6, 7, 8, 9, 10, 11, 12, 13, 14, 15, 16, 17, 18, 19 or 20.

31. The compound according to Embodiments 2 to 24, 26 to 29 or 30(b)-(j), wherein the saccharide chemically bonded to MHET or BHET via a glycosidic bond is methacrylated.

32. A Polymer of a compound according to at least one of Embodiments 1 to 31.

33. The polymer according to Embodiment 32, wherein the polymer is a biohybrid polymer.

34. A method for preparing a compound comprising glycosylated mono(2-hydroxyethyl) terephthalic acid (MHET) or glycosylated bis(2-hydroxyethyl) terephthalic acid (BHET), said method comprising the step of enzymatic glycosylation of mono(2-hydroxyethyl) terephthalic acid (MHET) or bis(2-hydroxyethyl) terephthalic acid (BHET).

35. The method according to embodiment 34, wherein in the step of enzymatic glycosylation the MHET or BHET and a saccharide are chemically bonded together via a glycosidic bond.

36. The method according to Embodiment 35, wherein the saccharide is a monosaccharide or disaccharide.

37. The method according to Embodiment 36, wherein the monosaccharide or disaccharide is selected from a group containing hexoses and pentoses.

38. The method according to Embodiment 37 wherein the monosaccharide or disaccharide is selected from α-glucose, β-glucose, α-fructose, β-fructose, α-galactose and β-galactose, α-mannose and β-mannose, xylose, N-acetylglucosamine, glucosamine and glucuronic acid.

39. The method according to at least one of Embodiments 34 to 38, wherein the enzymatic glycosylation is catalysed by a glucosidase, a galactosidase or a fructosidase.

40. The method according to Embodiment 39, wherein the enzymatic glycosylation is catalysed by a glucosidase.

41. The method according to Embodiment 40, wherein the glucosidase is an α-glucosidase or a β-glucosidase.

42. The method according to at least one of the Embodiments 34 to 41, wherein the MHET or BHET is obtainable by bacterial degradation or enzymatic degradation from polyethylene terephthalate (PET).

43. The method according to at least one of the Embodiments 34 to 42, wherein the method preferably comprises a step of bacterial degradation or enzymatic degradation of polyethylene terephthalate (PET) to MHET or BHET before the step of enzymatic glycosylation.

44. The method according to Embodiment 42 or 43, wherein the enzymatic degradation of PET is catalysed by a hydrolase.

45. The method according to Embodiment 44, wherein the hydrolase PETase is from *Idionella sakaiensis*.

46. The method according to Embodiment 44 or 45, wherein the hydrolase comprises the amino acid sequence shown in SEQ ID NO: 1.

47. The method according to at least one of Embodiments 42 to 46, wherein the enzyme for the enzymatic glycosylation of MHET or BHET and the enzyme for the enzymatic degradation of PET are used together.

48. The method according to Embodiment 47, wherein a microorganism containing the enzyme for enzymatic glycosylation and the enzyme for enzymatic degradation of PET is used.

49. The method according to one of Embodiments 34 to 48, wherein a methacrylic residue is chemically bonded to the glycosylated MHET or BHET in a further step, wherein the methacrylic residue is preferably chemically bonded to the glycosylated MHET or BHET by enzymatic esterification, wherein the enzymatic esterification is preferably catalysed by a lipase.

50. The method according to Embodiment 49, wherein the methacrylic residue is chemically bonded to the glycosylated MHET or BHET by addition of vinylmethyl methacrylate.

51. The method according to at least one of Embodiments 34 to 48, wherein a lipophilic side chain, preferably a saturated or unsaturated aliphatic hydrocarbon side chain, is chemically bonded to the glycosylated MHET or BHET in a further step.

52. The method according to claim 51, wherein the lipophilic side chain is a saturated or unsaturated $C_5$ to $C_{20}$ hydrocarbon side chain, preferably a saturated or unsaturated $C_5$ to $C_{15}$ hydrocarbon side chain, more preferably a saturated or unsaturated $C_8$ to $C_{12}$ hydrocarbon side chain, more preferably a saturated or unsaturated $C_{10}$ hydrocarbon side chain and especially preferably a saturated $C_{10}$ hydrocarbon side chain.

53. The method according to Embodiment 52, wherein the lipophilic side chain is a saturated $C_{10}$ hydrocarbon side chain.

54. The method according to one of Embodiments 51 to 53, wherein the lipophilic side chain is bound by addition of decanol.

55. The method according to at least one of Embodiments 34 to 54, wherein a step of polymerisation follows after the step of enzymatic glycosylation.

56. A Polymer obtainable by the method according to one of Embodiments 34 to 55.

57. The polymer according to Embodiment 56, wherein the polymer is a biohybrid polymer.

58. A Microorganism containing at least one enzyme for the enzymatic glycosylation of MHET and/or BHET and at least one enzyme for the enzymatic degradation of PET.

59. The microorganism according to Embodiment 58, wherein the microorganism is a recombinant microorganism and the enzyme for enzymatic glycosylation of MHET and/or BHET and/or the enzyme for enzymatic degradation of PET is a recombinant enzyme.

60. The microorganism according to Embodiment 58 or 59, wherein the enzyme for enzymatic glycosylation is a glucosidase, a galactosidase or a fructosidase.

61. The microorganism according to Embodiment 60, wherein the enzyme for the enzymatic glycosylation is a glucosidase.

62. The microorganism according to Embodiment 61, wherein the glucosidase is an α-glucosidase or a β-glucosidase.

63. The microorganism according to at least one of the Embodiments 58 to 62, wherein the enzyme for the enzymatic degradation of PET is a hydrolase.

64. The microorganism according to Embodiment 63, wherein the hydrolase PETase is from *Idionella sakaiensis*.

65. The microorganism according to Embodiment 63 or 64, wherein the hydrolase comprises the amino acid sequence shown in SEQ ID NO: 1.

66. A Compound produced by enzymatic glycosylation of mono(2-hydroxyethyl) terephthalic acid (MHET) or bis (2-hydroxyethyl) terephthalic acid, wherein MHET or bis(2-hydroxyethyl) terephthalic acid is produced by bacterial or enzymatic degradation from PET.

67. A compound characterised by a mono(2-hydroxyethyl) terephthalic acid (MHET) or bis(2-hydroxyethyl) terephthalic acid chemically bound to a saccharide.

68. The compound according to Embodiments 66 and 67, wherein the MHET or bis(2-hydroxyethyl) terephthalic acid and the saccharide are chemically bonded to each other via a glycoside bond.

69. A compound, which can be polymerised after glycosylation of mono(2-hydroxyethyl) terephthalic acid (MHET) or bis(2-hydroxyethyl) terephthalic acid.

70. The compound according to Embodiment 66 or 67, wherein the saccharide is a monosaccharide or disaccharide.

71. The compound according to Embodiment 70, said monosaccharide or disaccharide being selected from the group consisting of hexoses and pentoses (α-glucose, β-glucose, α-fructose, β-fructose, α-galactose and β-galactose, α-mannose and β-mannose, xylose, N-acetylglucosamine, glucosamine, glucuronic acid).

DETAILED DESCRIPTION OF THE INVENTION

Figure 1:
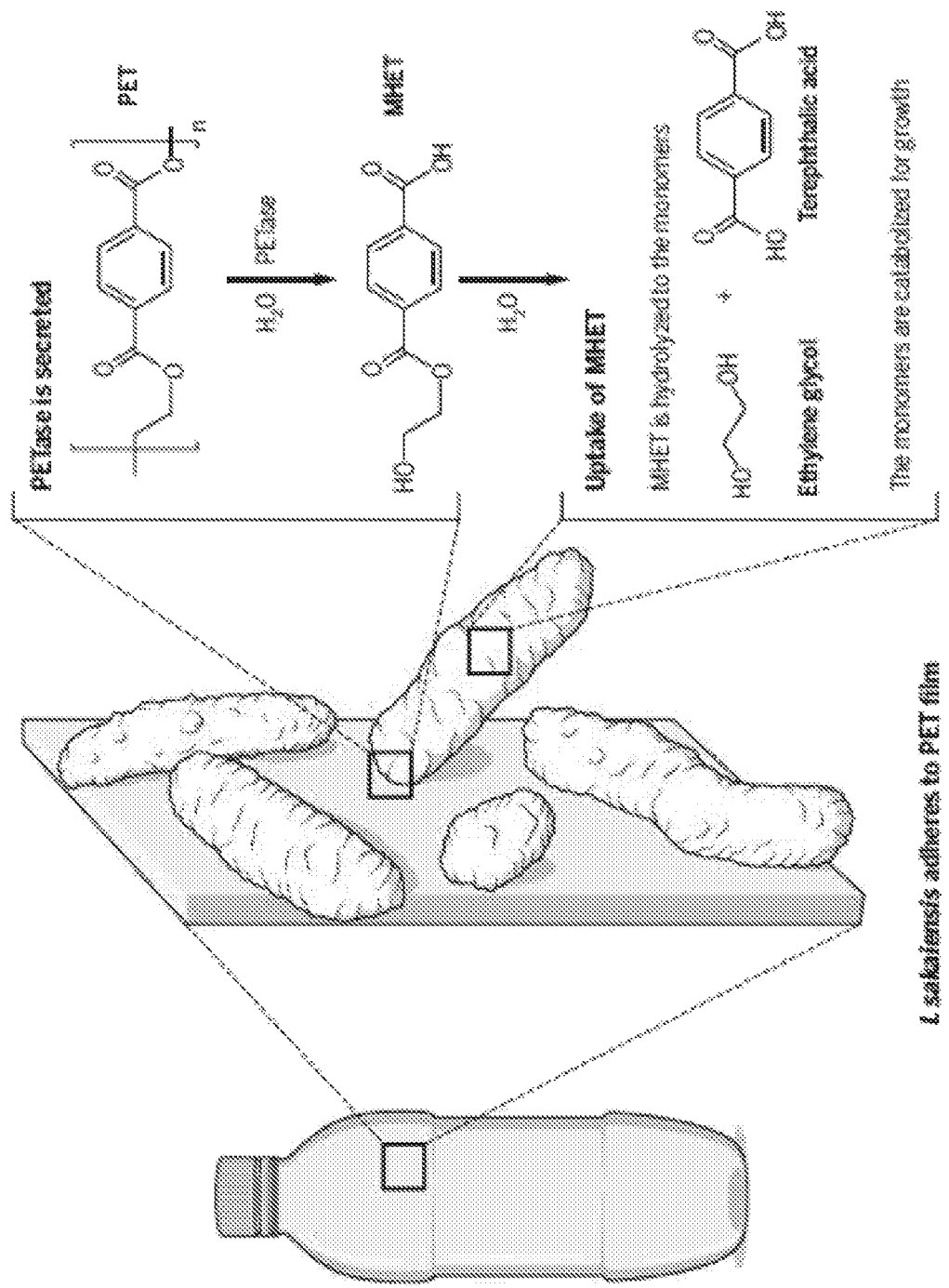
FIG. 1: Figure from: U. Bornscheuer, *Science* 351, 1154 (2016); Decomposition of PET by *I. sakaiensis*.

Definitions and general techniques Unless otherwise indicated, the terms used in this invention are to be understood in their usual meaning for the skilled person.

Terms such as "comprise" or "comprising" are used here in such a way that any occurrence of these terms can optionally be replaced by "consist of" or "consisting of".

Terms such as "contain" or "containing" are used here in their usual meaning for the skilled person. Optionally, each occurrence of these terms can be replaced by "consist of" or "consisting of".

The term "compound" is used here in such a way as it would be understood by the skilled person, i.e. meaning "chemical compound" in particular.

The term "compound comprising glycosylated mono(2-hydroxyethyl) terephthalic acid (MHET) or glycosylated bis(2-hydroxyethyl) terephthalic acid (BHET)" should be understood to mean that with the respective mono(2-hydroxyethyl) terephthalic acid (MHET) or bis(2-hydroxyethyl) terephthalic acid (BHET) optional also esters, amides, thioesters and ethers of the respective mono(2-hydroxyethyl) terephthalic acid (MHET) or bis(2-hydroxyethyl) terephthalic acid (BHET) are meant. In one embodiment esters, amides, thioesters and ethers of the respective mono (2-hydroxyethyl) terephthalic acid (MHET) or bis(2-hydroxyethyl) terephthalic acid (BHET) are not comprised under the term "compound comprising glycosylated mono (2-hydroxyethyl) terephthalic acid (MHET) or glycosylated bis(2-hydroxyethyl) terephthalic acid (BHET)".

The glycosidic bond is the chemical bond between the anomeric carbon atom of a glycon, i.e. a saccharide, and the hetero or less common carbon atom of an aglycon, a "non-sugar". A glycosidic bond can be both an α-glycosidic bond and a β-glycosidic bond. The prefixes α and β define the anomeric configuration.

A glycosidic bond can be formed by enzymatic glycosylation. Enzymatic glycosylation can be catalysed by a glycosidase, glycosidases belonging to the enzyme class of hydrolases and being classified under EC 3.2.1. Glycosidases can reversibly hydrolyse α- or β-glycosidic bonds. Examples of glycosidases comprise glucosidases, galactosidases, sialidases, mannosidases, fucosidases, xylosidases, glucuronidase, α-L-arabinofuranosidase, exo-β-glucosaminidase, galacturonase, glucosaminidase, N-acetylglucosaminidase and fructosidases. Specifically, a glycosidase can be an α or a β-glucosidase. Furthermore, a glycosidase can be a β-galactosidase.

Lipophilic can particularly mean hydrophobic. Lipophilic side chains comprise, for example, hydrocarbons, and in particular aliphatic hydrocarbons.

A hydrocarbon side chain is a side chain consisting of carbon and hydrogen. The hydrocarbon side chain can be saturated or unsaturated. An unsaturated hydrocarbon side chain includes both a monounsaturated and a polyunsaturated hydrocarbon side chain. The hydrocarbon side chain may contain double bonds and triple bonds between two carbon atoms. Furthermore, individual carbon atoms in the hydrocarbon chain can optionally be replaced by heteroatoms. The hydrocarbon chain can be unbranched or branched. The hydrocarbon chain can be acyclic or cyclic.

In multiple glycosylations, the acceptor is typically glycosylated first. If sufficient monoglycosylated acceptor is present in the reaction mixture, multiple glycosylations may occur.

As glycosidases for enzymatic syntheses can be used, for example:

α glucosidase (sucrose isomerase): in suspension of microorganisms (*Protaminobacter rubrum* Z 12 (CBD 574.77)). It can preferably be used for monoglucosylation. The optimal pH value for the enzymatic reaction is pH=6.

α glucosidase, GTFR from *Streptococcus oralis* first transfers glucose to the acceptor. After a longer reaction time, another glucose unit is transferred to the glucose of the glucosylated acceptor, as demonstrated in example (6). The optimal pH value for the enzymatic reaction is pH=6. GTFR can be purified from *S. oralis* as in Fujiwara et al. (Fujiwara et al., Infect Immun., 2000; 68(5):2475-83 2000).

β glucosidase from almonds EC.3.2.1.21, CAS 9001-22-3 (BioChemika 49290, WA10531). The optimal pH value for the enzymatic reaction is pH=5.2.

β galactosidase from *Aspergillus oryzae*, CAS 9031-11-2 (Sigma G5160-25KU). The optimal pH value for the enzymatic reaction is pH=5.2.

β fructosidase from yeast (Boehringer Mannheim GmbH, order number 104914). The optimal pH value for the enzymatic reaction is pH=5.2.

Lipase Novozymes 435 can be used for enzymatic esterification or transesterification. The optimal pH value for the enzymatic reaction is pH=7.5.

General description of the separation of reaction mixtures and isolation of reaction products according to the invention:

All compounds of the invention can be isolated. Accordingly, all methods according to the invention preferably include the isolation of the respective compound.

This can preferably be done as follows:

The reaction mixtures are distilled off from solvents or lyophilized. Glycosylated MHET or glycosylated BHET is separated by column chromatography. The chromatography material is silica gel 60 (Macherey Nagel, 0.044-0.063 mm). For each gram of reaction mixture to be separated, 100 g silica gel are used. The separation vessels are glass columns. Preferably columns with a diameter to length of 1:20 are used. The silica gel is sponged in a solvent mixture of ethyl acetate:isopropanol:water (volume ratio 6:3:1), for non-polar substances a mixture of ethyl acetate:methanol (volume ratio 12:1) is used, and the column is filled. Then the reaction mixture is dissolved in as little solvent as possible (preferably 1 g in 1 ml) and placed on the column. Separation takes place by elution with the solvent. The eluate is collected in vessels (a 10 ml) and determined by HPLC in which vessels the product is contained. The vessels are combined with the product and the solvents are evaporated. A solid is obtained.

Embodiments

In the invention, MHET or bis(2-hydroxyethyl) terephthalic acid is glycosylated using an enzyme and a glycose substrate. Disaccharides (e.g. sucrose, lactose, maltose), oligosaccharides (maltooligosaccharides) or polysaccharides (dextran, fructooligosaccharides, chitin, mannan, cellulose) are used as glycosubstrates. The preparation of glycosylated MHET or bis(2-hydroxyethyl) terephthalic acid can be carried out from MHET or bis(2-hydroxyethyl) terephthalic acid. MHET or bis(2-hydroxyethyl) terephthalic acid can be produced from PET using a hydrolase, e.g. with the PETase from *I. sakaiensis*, e.g. having the amino acid sequence shown in SEQ ID NO: 1: MNFPRAS-RLMQAAVLGGLMAVSAAATAQTNP-YARGPNPTAASLEASAGPFTVRSFTVSRPSGYGA GTVYYPTNAGGTVGAIAIVPGYTARQSSIKWWGPR-LASHGFVVITIDTNSTLDQPSSRSSQQMAALR QVASLNGTSSSPIYGKVDTARMGVMGWSMGG-GGSLISAANNPSLKAAAPQAPWDSSTNFSSVTVP TLI-FACENDSIAPVNSSALPIYDSMSRNAKQFLEINGGSH-SCANSGNSNQALIGKKGVAWMKRFMDN DTRYST-FACENPNSTRVSDFRTANCS (SEQ ID NO: 1). Both enzymes can be used together. A microorganism containing both enzymes can also be used for production (see FIG. 2).

The compound of the invention is characterised by a MHET or bis(2-hydroxyethyl) terephthalic acid chemically bonded to a saccharide. Glycosylated MHET or bis(2-hydroxyethyl) terephthalic acid can be used as an active ingredient. Glycosylated MHET or bis(2-hydroxyethyl) terephthalic acid can also be polymerised to biohybrid polymers (see FIG. 3).

Especially preferred, MHET or bis(2-hydroxyethyl) terephthalic acid and the saccharide are chemically bonded to each other via a glycosidic bond. The glycosidic bond is the chemical bond between the anomeric carbon atom of a glycon, i.e. a saccharide, and the hetero or less common carbon atom of an aglycon, a "non-sugar". Compounds containing a glycosidic bond are commonly referred to as glycosides. The hydrolysis of a glycosidic bond in a glycoside is reversibly catalysed in particular by glucosidases, wherein the glycon, i.e. the saccharide present, and the aglycon, here MHET or bis(2-hydroxyethyl) terephthalic acid, are released using a water molecule.

Preferably the saccharide is a monosaccharide. Monosaccharides are simple sugars with a basic structure of at least three linked carbon atoms which have a carbonyl group (—C=O) and at least one hydroxyl group (—OH).

Figure 4:
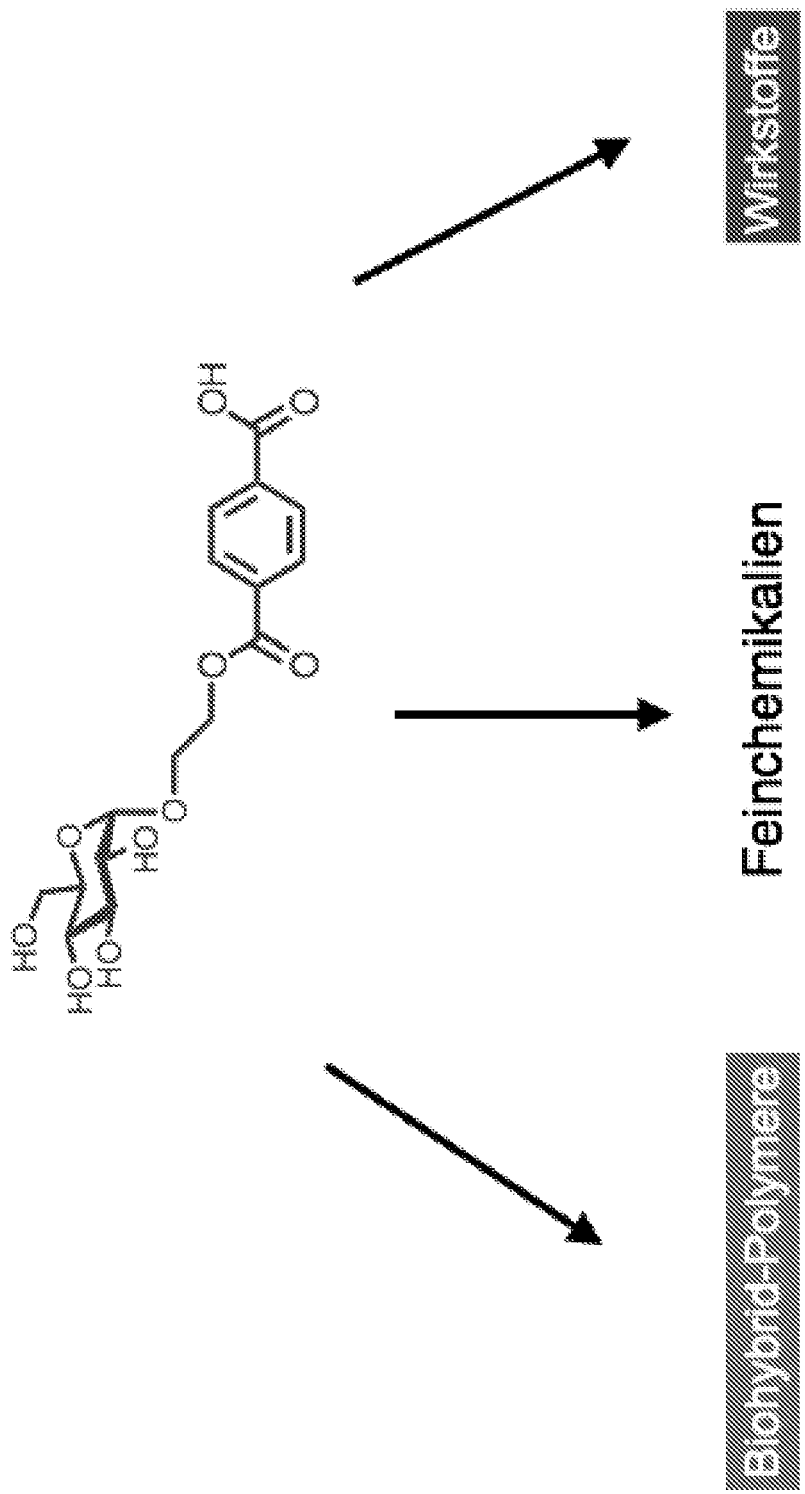
FIG. 4: Glycosylated MHET is used as active ingredient, fine chemical or for the synthesis of polymers.

Glycosylated MHET or bis(2-hydroxyethyl) terephthalic acid serves as a fine chemical, active ingredient or starting material for biohybrid polymers (see FIG. 4). By polycondensation of glycosylated MHET or bis(2-hydroxyethyl) terephthalic acid a thermoplastic polymer of the polyester family can be formed. By polycondensation of glycosylated MHET or bis(2-hydroxyethyl) terephthalic acid a thermoplastic from the polyester family is formed.

Furthermore, a polyester can be prepared by transesterification of di- and monoglucosylated bis(2-hydroxyethyl) terephthalic acid with ethanediol. Since this is an equilibrium reaction, split-off ethanediol is distilled in albumin. The glycosylated bis(2-hydroxyethyl) terephthalic acid is enriched. Likewise, mono- and diglycosylated bis(2-hydroxyethyl) terephthalic acid is esterified directly with terephthalic acid to a polyester.

Antimony(III) oxide, for example, can be used as a catalyst.

Figure 5:
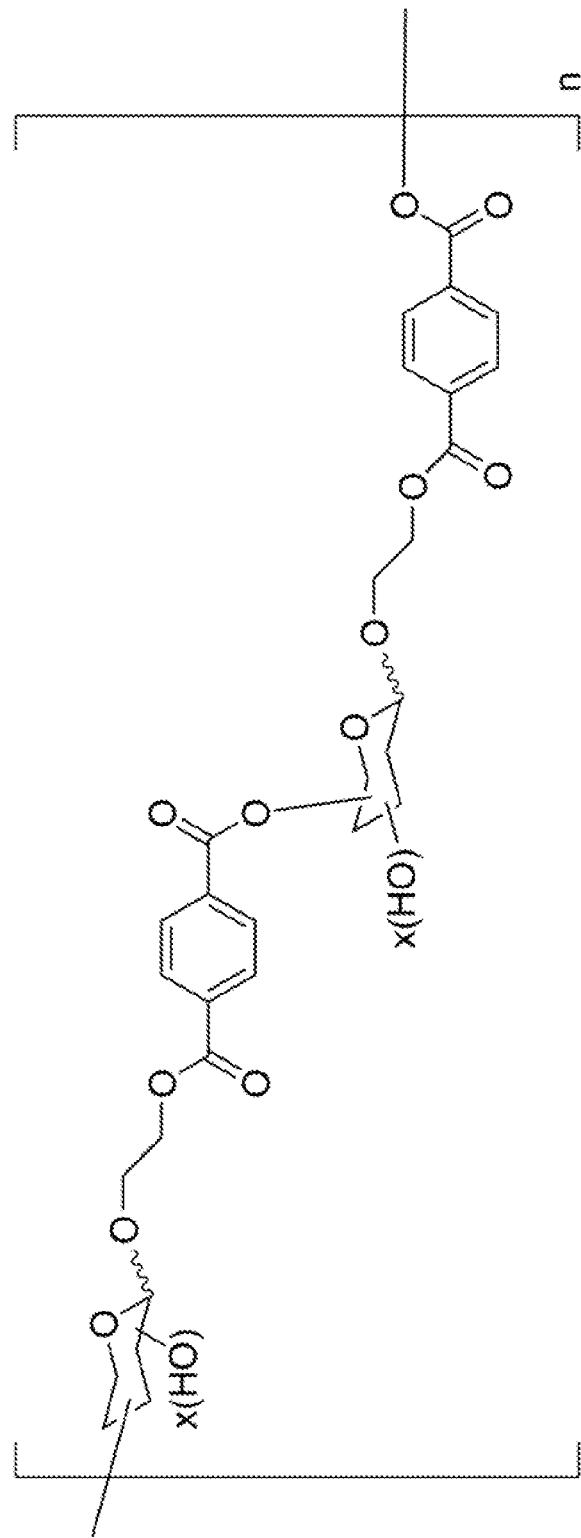
FIG. 5: Exemplary structure of a biohybrid polymer of glucosylated MHET or bis(2-hydroxyethyl) terephthalic acid.

A biohybrid polymer of glucosylated MHET or bis(2-hydroxyethyl) terephthalic acid can assume the structure from FIG. 5.

Glycosylated MHET and BHET Methacrylates

Similarly, glycosylated MHET and glycosylated bis(2-hydroxyethyl) terephthalic acid can be combined with methacrylate. For this purpose, methacrylate is esterified enzymatically with one or more alcohol functions of MHET or bis(2-hydroxyethyl) terephthalic acid. When BHET-α-Glc is reacted with vinyl methyl acrylate at 50° C. and Lipase Novozymes 435, when tert-butyl alcohol is used as the solvent, the double esterified product $MA_2$-BHET-α-Glc and the single glycosylated MA-BHET-α-Glc (FIG. 6) is formed.

Figure 8:
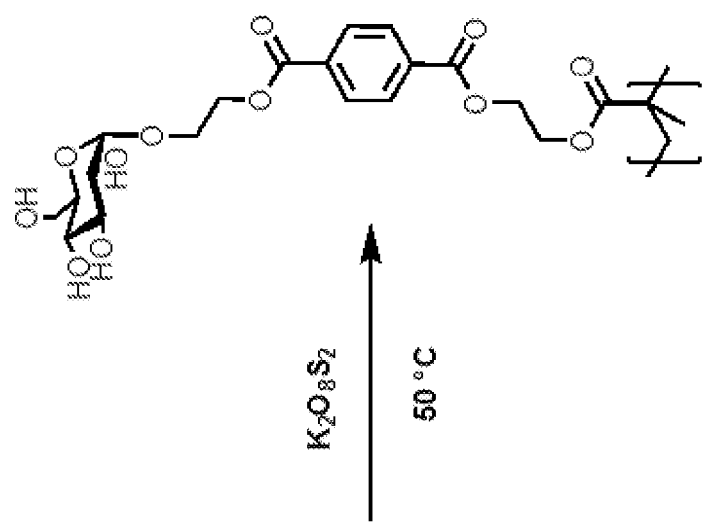
FIG. 8: Synthesized glycosylated BHET methacrylates and glycosylated MHET methacrylates can be polymerised using a radical initiator, e.g. potassium peroxodisulfate.
Figure 8:
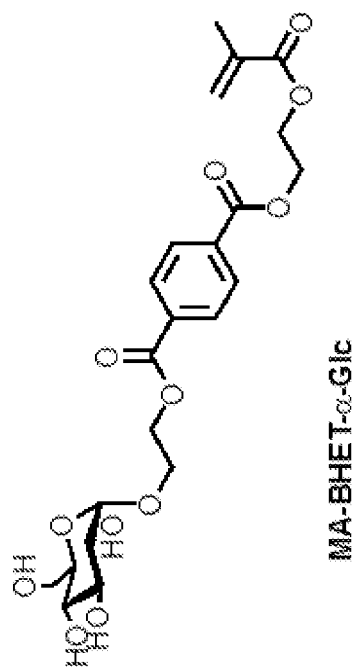
Figure 9:
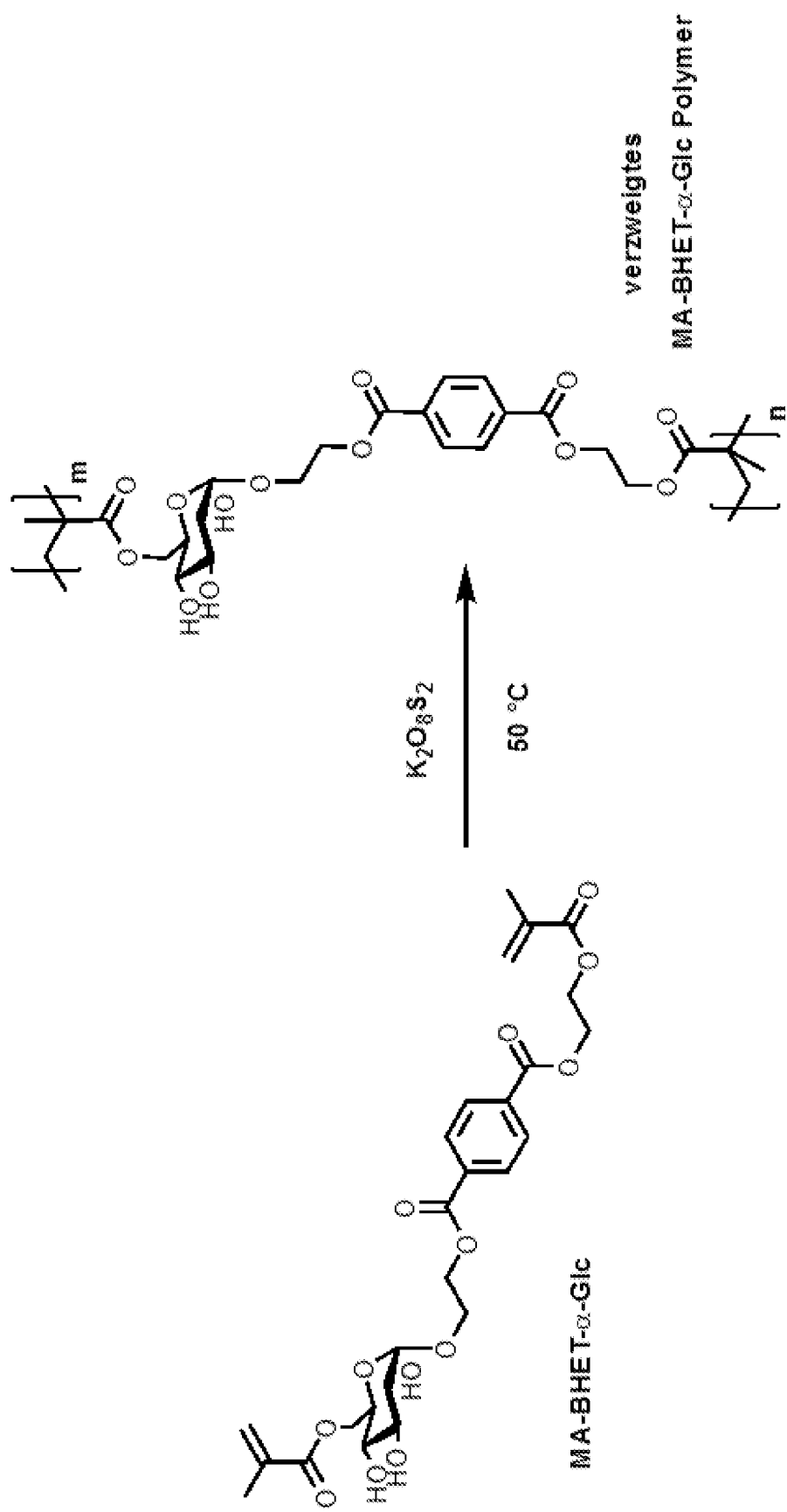
FIG. 9: Synthetized glycosylated BHET methacrylates and glycosylated MHET methacrylates can be polymerised with the aid of a radical initiator, e.g. potassium peroxodisulfate.
Figure 10:
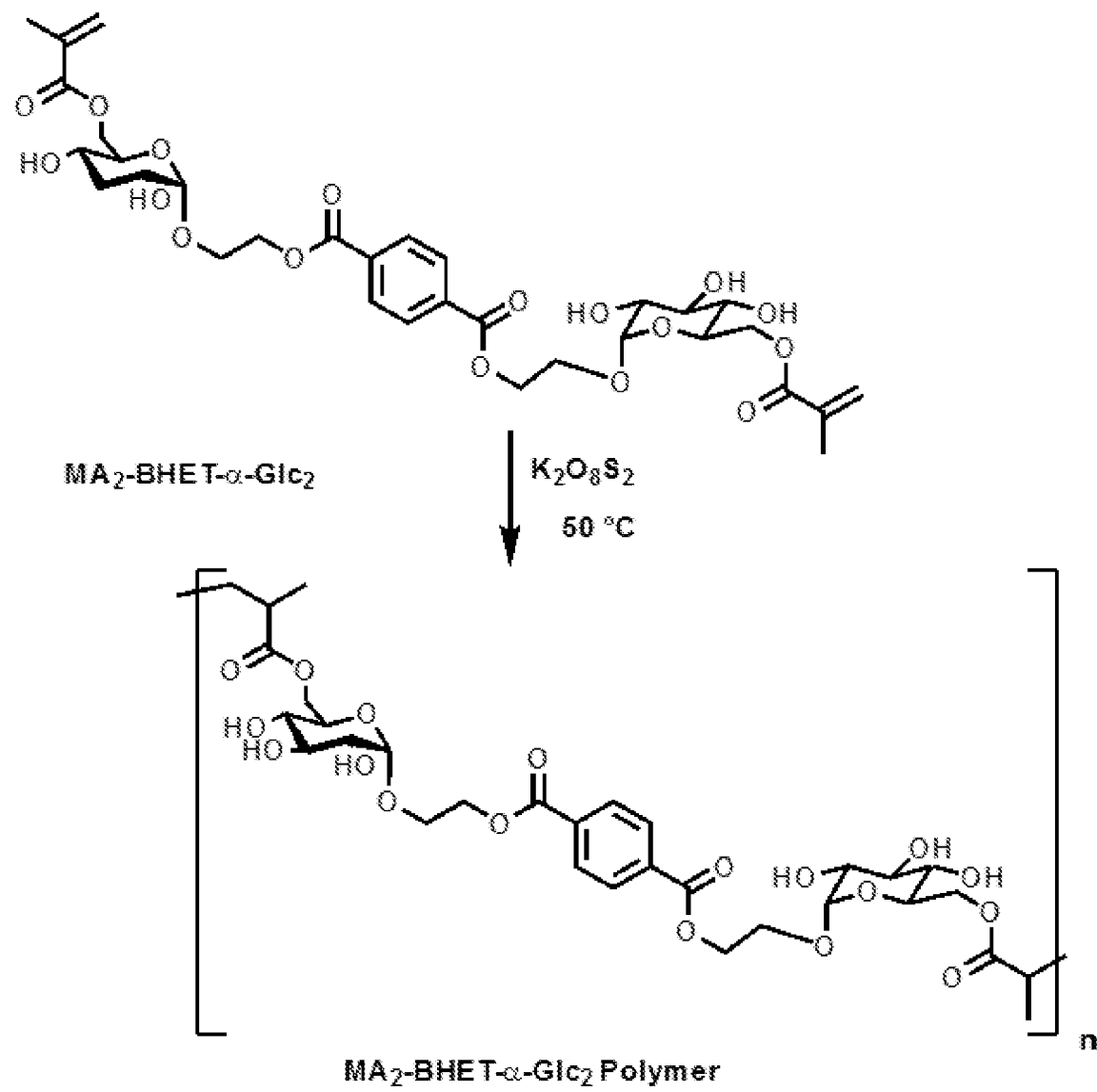
FIG. 10: Synthesized glycosylated BHET methacrylates and glycosylated MHET methacrylates can be polymerised with the aid of a radical initiator, e.g. potassium peroxodisulfate.

Polymerisation of Glycosylated BHET Methacrylates and Glycosylated MHET Methacrylates The synthesized glycosylated BHET methacrylates and glycosylated MHET methacrylates can be polymerised using a radical initiator, e.g. potassium peroxodisulfate (FIG. 8, FIG. 9, FIG. 10).

It is also possible to mix various methacrylates in different ratios and polymerise the mixtures. In this way, block polymers can also be produced.

Glycosylated MHET and BHET Lipids

Figure 11:
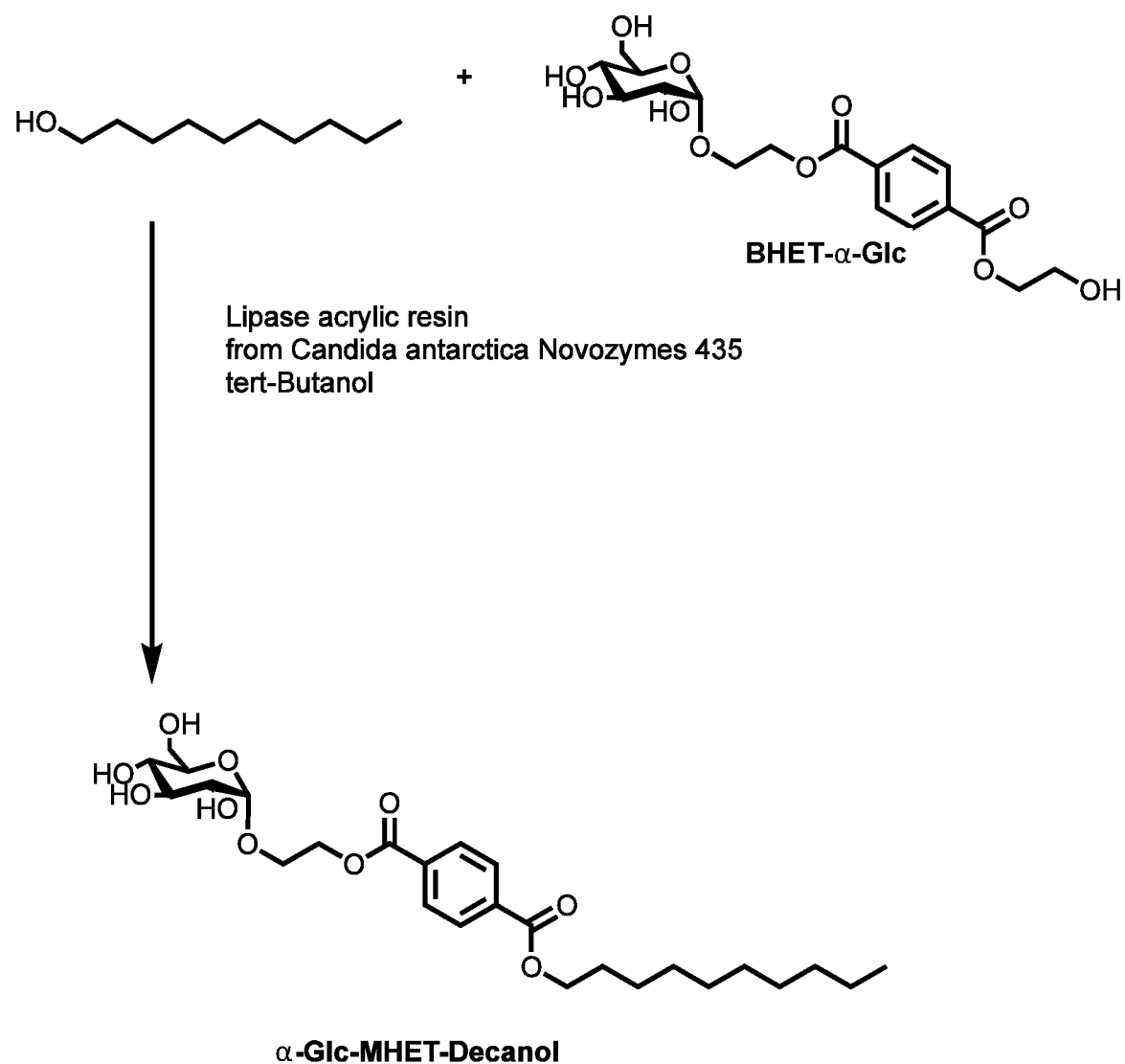
FIG. 11: Glycosylated MHET and glycosylated bis(2-hydroxyethyl) terephthalic acid can also be linked to aliphatic alcohols. For this e.g. dodecanol esterified enzymatically with BHET-α-Glc.
Figure 12:
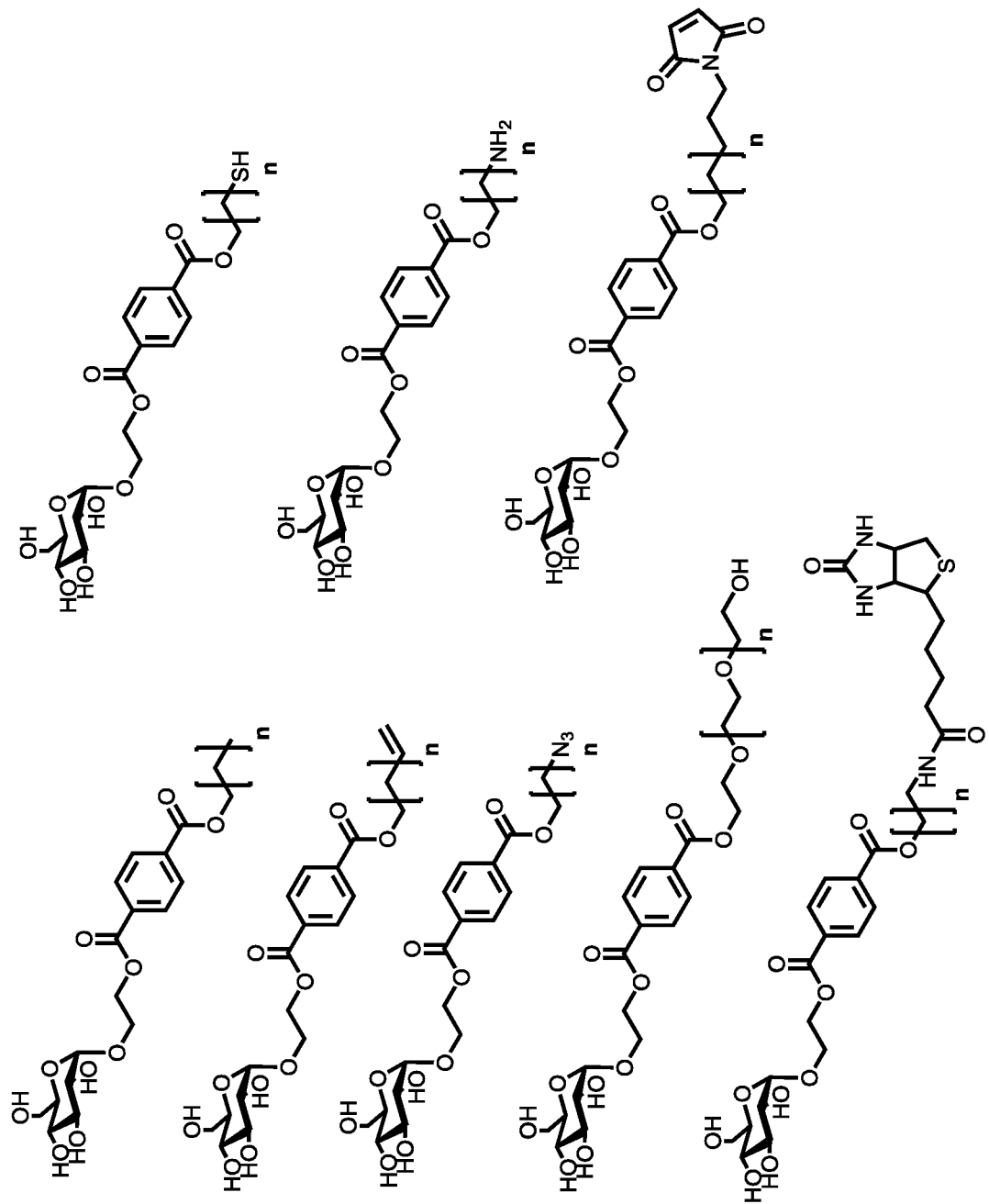
FIG. 12: Instead of decanol, thiols, amines and other alcohols can also be conjugated with glycosylated BHET.

Glycosylated MHET and glycosylated bis(2-hydroxyethyl) terephthalic acid can also be linked to aliphatic alcohols. For this purpose, e.g. decanol is enzymatically esterified with BHET-α-Glc (FIG. 11). When BHET-α-Glc is reacted with decanol at 50° C. and Lipase Novozymes 435, when using the solvent tert-Butanol, α-Glc-MHET-Decanol is preferably produced (FIG. 11). Instead of decanol, thiols, amines and other alcohols can also be conjugated with glycosylated BHET. This allows the introduction of different linkers that contain biotin or can be used for bioorthogonal click reactions to build cell culture scaffolds (FIG. 12).

It is particularly preferable that the monosaccharide is selected from a group containing pentoses and hexoses. Hexoses ($C_6H_{12}O_6$) have a carbon backbone with six carbon atoms and differ fundamentally in the type of carbonyl function. With a non-terminal carbonyl function ($R_1$—C(O)—$R_2$), a ketogroup, a ketohexose is meant. A terminal carbonyl function, an aldehyde group, is aldohexose.

Pentoses ($C_5H_{10}O_5$) have a carbon backbone with five carbon atoms.

The hexoses are preferably selected from a group containing α-glucose, β-glucose, α-fructose, β-fructose, α-mannose, β-mannose, α-galactose and β-galactose, N-acetyl glucosamine, glucosamine, glucuronic acid. Depending on which saccharide is chemically bound to the MHET or bis(2-hydroxyethyl) terephthalic acid, the nomenclature of the compound also differs. In an α or β glucose chemically bound to MHET or bis(2-hydroxyethyl) terephthalic acid, the compound is a or 13 glucosylated MHET or bis(2-hydroxyethyl) terephthalic acid. An α or a β galactose as chemically bound saccharide is called α or β galactosylated MHET or bis(2-hydroxyethyl) terephthalic acid. If an α or a ρ fructose is bound to the MHET as saccharide, it is α or β fructosylated MHET or bis(2-hydroxyethyl) terephthalic acid.

Advantageously, the pentoses are selected from a group containing xylose, arabinose or xylose.

In a particularly advantageous embodiment of the invention a glucose is connected via a glycosidic bond with MHET or bis(2-hydroxyethyl) terephthalic acid. Synthesis of α-glycosylated MHET or bis(2-hydroxyethyl) terephthalic acid is carried out with water separation from α-glucose and MHET or bis(2-hydroxyethyl) terephthalic acid. This produces α-glycosylated MHET or bis(2-hydroxyethyl) terephthalic acid.

Figure 13:
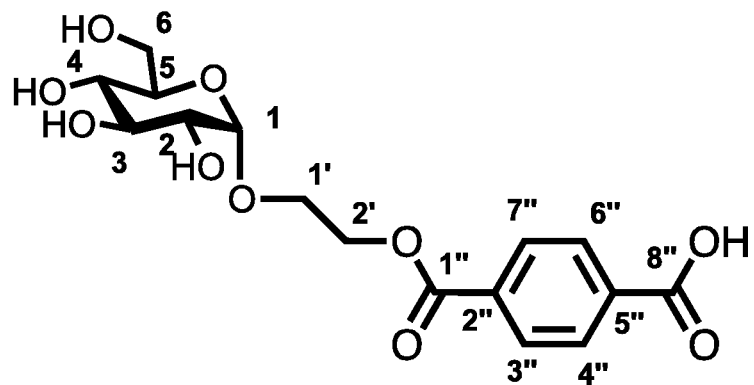
FIG. 13: Exemplary representation of the structure of α-glycosylated MHET.

The compound α-glycosylated MHET is preferably characterised by the structural formula shown in FIG. 13.

In the synthesis of α-glycosylated MHET, a glycosidic bond is formed between α-glucose and MHET. Bonding is particularly advantageous selectively via the hydroxyl group of the MHET bonded to the 1' carbon atom. The oxygen atom bridging the α-glucose with the MHET comes from the MHET. In principle, this bond linkage—independent of the saccharide used—preferably occurs selectively via the hydroxyl group of the MHET bonded to the 1' carbon atom. The enzyme used is responsible for the selectivity of the bond linkage at the 1'C atom.

In the following, exemplary embodiments of the invention will be explained in more detail with reference to the manufacturing methods of the compound.

EXAMPLES

All following exemplary embodiments were carried out experimentally.

(1) Production of MHET

Figure 14:
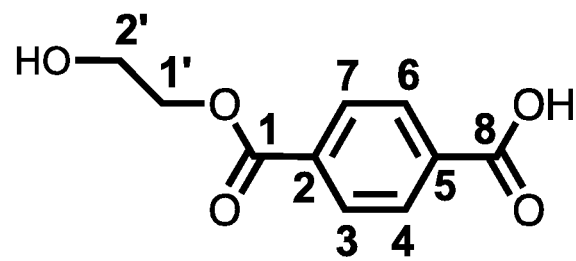
FIG. 14: Exemplary representation of the structure of MHET.

MHET is shown as an example in FIG. 14.

$NaHCO_3$ (3.05 g, 36 mmol) was added to a solution of terephthalic acid (2.00 g, 12.04 mmol) in DMF (15 ml). The mixture was stirred for 50 minutes at 85° C. Then 2-bromo-1-ethanol (0.75 g, 426 µl, 6 mmol) was added and stirred for another 4 h at 85° C. The course of the reaction is monitored by thin-layer chromatography (MeOH/$CH_2Cl_2$, 1:4). The reaction mixture is then filtered over silica and separated after concentration in silica (MeOH/$CH_2Cl_2$, 1:4).

For the spectroscopic detection of MHET, $^1$H-NMR spectra and $^{13}$C-NMR spectra were recorded.

The $^1$H-NMR spectrum 1 was recorded at 400 MHz in deuterated dimethyl sulfoxide, the assignment of the signals is shown in Table 1.

Table 1: Signal assignment $^1$H-NMR spectrum of MHET

TABLE 1

Signal assignment $^1$H-NMR spectrum of MHET

| δ [ppm] | Assignment | Relative integral | Multiplicity | Coupling ratio J [Hz] |
| --- | --- | --- | --- | --- |
| 8.01 | H-3, H-7 | 2H | Doublet | 8.37 |
| 7.93 | H-4, H-6 | 2H | Doublet | 8.37 |

TABLE 1-continued

Signal assignment ¹H-NMR spectrum of MHET

| δ [ppm] | Assignment | Relative integral | Multiplicity | Coupling ratio J [Hz] |
|---|---|---|---|---|
| 4.28 | H-1' | 2H | Triplet | |
| 3.71 | H-2' | 2H | Triplet | |

Figure 50:
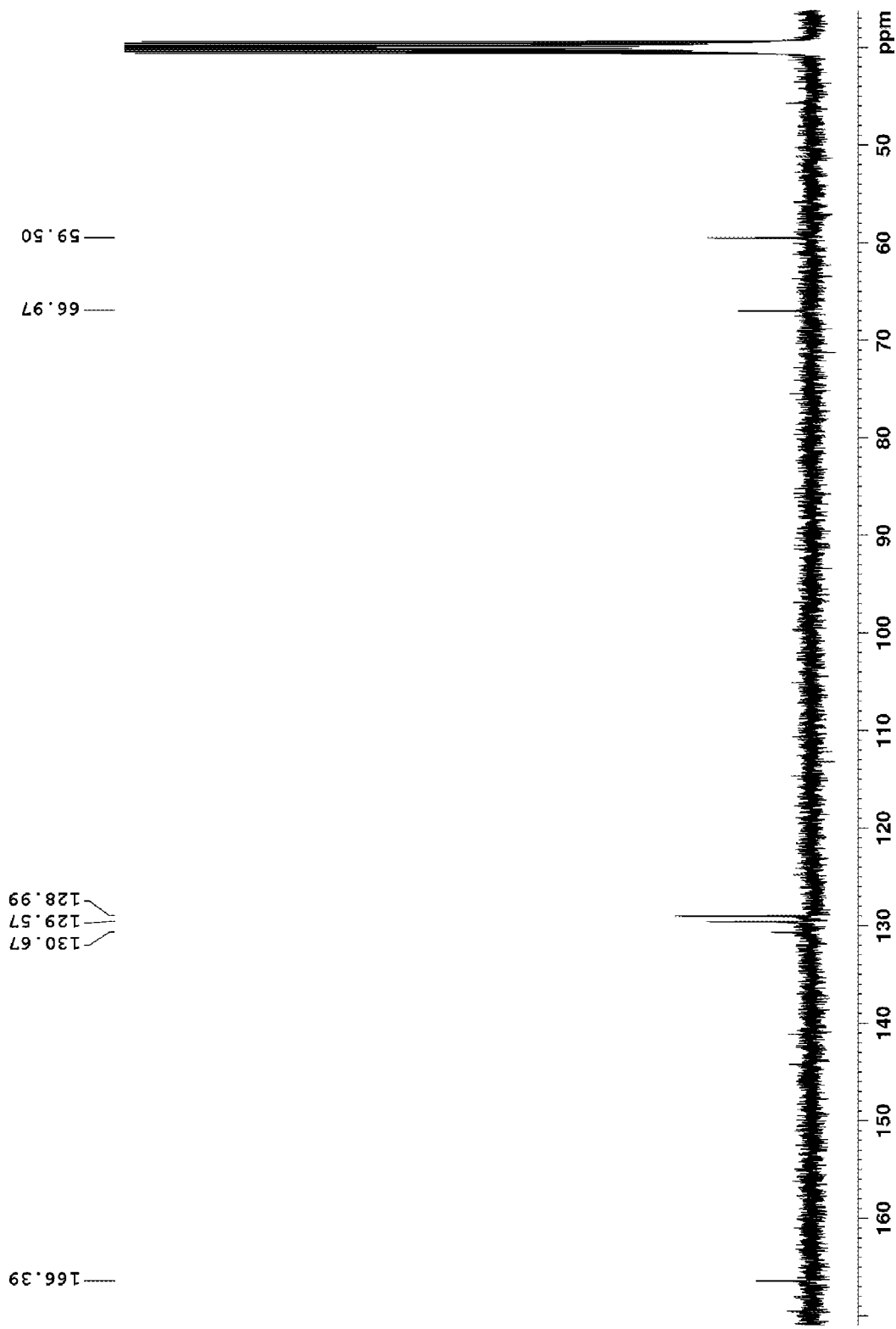
FIG. 50: Exemplary $^{13}$C-NMR spectrum of MHET shown

FIG. 50 shows an example $^{13}$C-NMR spectrum of MHET. The $^{13}$C-NMR spectrum 11 was also recorded at 100 MHz in deuterated dimethyl sulfoxide. The assignment of the signals is listed in Table 2.

TABLE 2

Signal assignment of the $^{13}$C-NMR spectrum of MHET

| δ [ppm] | Assignment |
|---|---|
| 166.39 | C-1, C-8 |
| 130.67 | C-2, C-5 |
| 129.57 | C-3, C-7 |
| 128.99 | C-4, C-6 |
| 66.97 | C-1' |
| 59.50 | C-2' |

MHET is clearly determined by the chemical shifts of the signals of the H or C atoms and the integral values (in the case of the H atoms), which can be taken from the tables. A mass spectrum was also measured. This also confirms MHET.

MS (ESI, negative): calculated for $C_{10}H_9O_5$ (M-H)– 209.045; gem. 209.045

(2) Production of α-glucosylated MHET MHET (0.05 mol/l) and sucrose (0.4 mol/l) are dissolved in 0.05 M phosphate buffer (0.05 mol/l, pH=6) and a suspension of microorganisms (*Protaminobacter rubrum* Z 12 (CBS 574.77)) is added. In an alternative embodiment, an α-glucosidase solution (100 U in phosphate buffer) is added.

Sucrose consists of α-D-glucose and β-D-fructose, which are linked via an α,β-1,2-glycosidic bond. The microorganism *Protaminobacter rubrum* Z 12 contains an enzyme, an α-glucosidase. It catalyses the cleavage of the sucrose used into α-D-glucose and β-D-fructose. The α-D-glucose chemically binds to the MHET during the reaction.

For this purpose, the reaction mixture is shaken at a temperature of 37° C. in a water bath. After optimal product formation, the reaction is terminated. The product α-glycosylated MHET is obtained. Optimal product formation is determined by continuous sampling and thin-layer chromatography. α-glucosylated MHET is shown in FIG. 13 as an example.

The test results of the embodiment with a suspension of microorganisms (*Protaminobacter rubrum* Z 12 (CBS 574.77)) are as follows.

The product is confirmed by mass spectrometry (MT203).

MS (ESI, negative): calculated for $C_{16}H_{19}O_{10}$ (M-H)⁻ 371.0978; according to 371.09727

(3) Production of β-glucosylated MHET

MHET (0.05 mol/l) and cellobiose (0.4 mol/l) are dissolved in sodium acetate buffer (0.05 mol/l, pH=5.2) or phosphate buffer (0.05 mol/l, pH=7) and a β-glucosidase solution (100 U in sodium acetate buffer or phosphate buffer) is added. Cellobiose is a disaccharide consisting of two glucose molecules linked together by β-1,4-glucoside.

The enzyme β-glucosidase enables the degradation of cellobiose to glucose. The glucose binds chemically to the MHET during the reaction.

Figure 15:
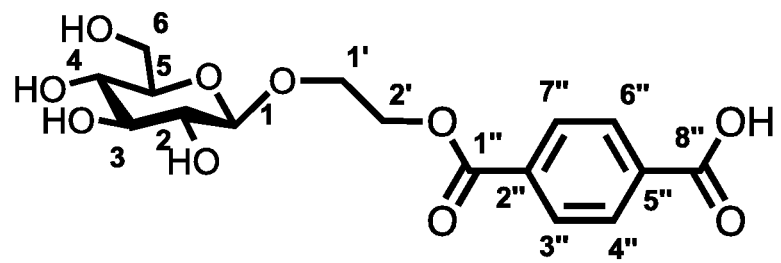
FIG. 15: Exemplary representation of the structure of β-glycosylated MHET.

The reaction mixture is also shaken at a temperature of 37° C. in a water bath. After optimal product formation, the reaction is terminated. After column chromatography, β-glucosylated MHET is obtained. β-glucosylated MHET is shown in FIG. 15 as an example.

The test results of the embodiment with sodium acetate buffer are as follows.

The product is confirmed by mass spectrometry (MT204).

Figure 16:
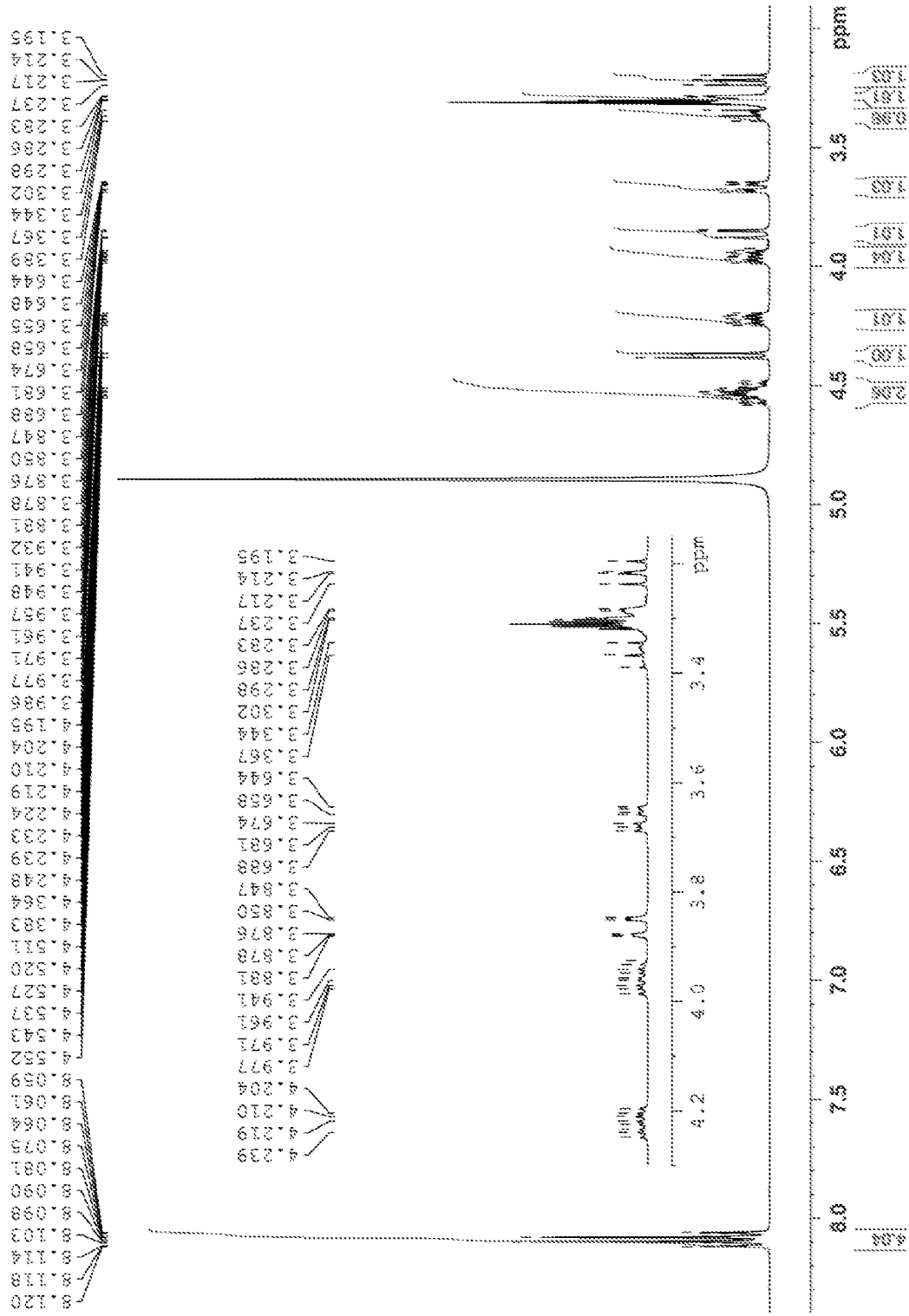
FIG. 16: $^1$H-NMR spectrum of β-glycosylated MHET.
Figure 17:
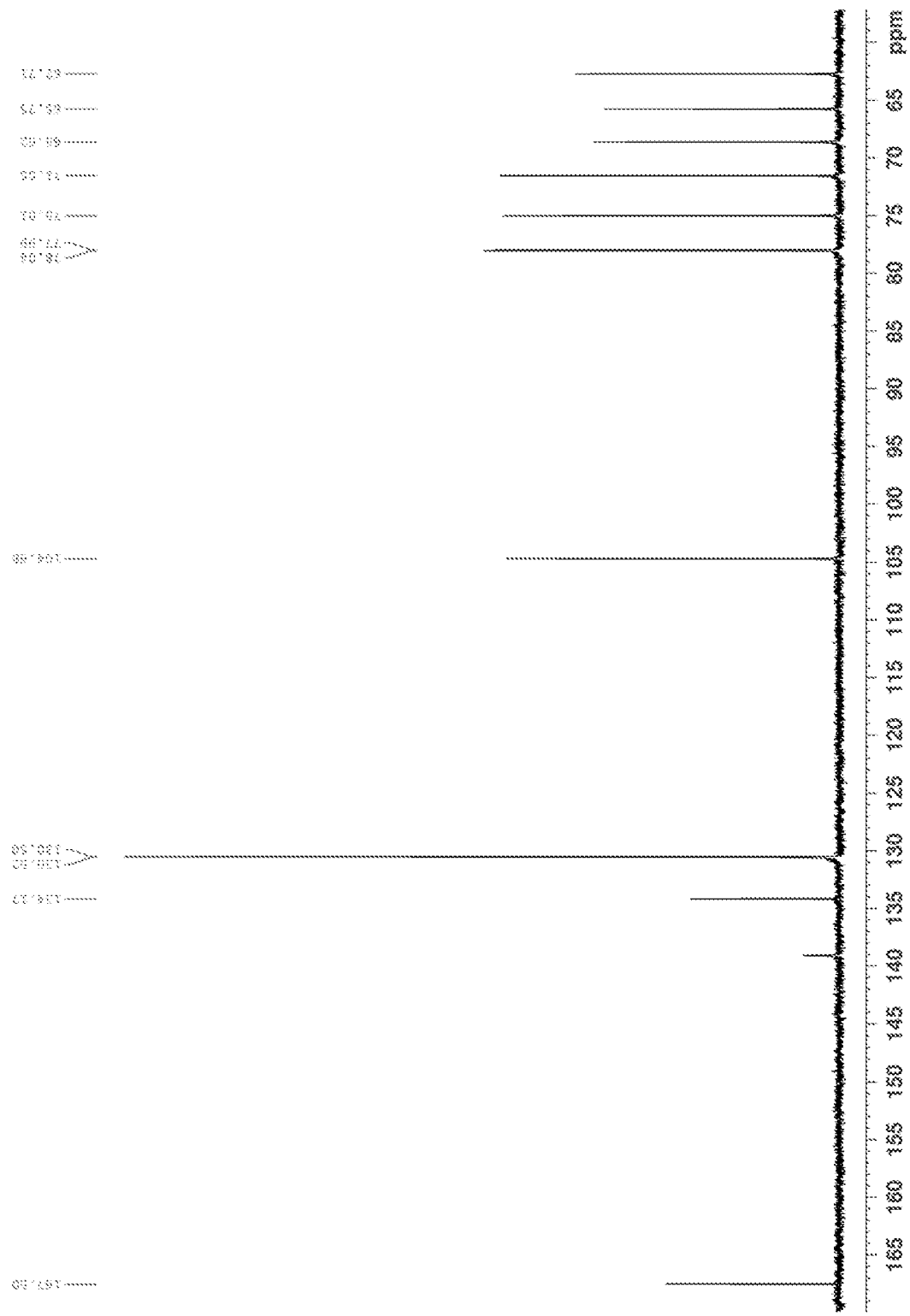
FIG. 17: $^{13}$C-NMR spectrum of β-glycosylated MHET.

MS (ESI, negative): calculated for $C_{16}H_{19}O_{10}$ (M-H)⁻ 371.0978; according to 371.0972. Further test results are shown in FIG. 16, FIG. 17 and the following tables.

TABLE 3

Signal assignment ¹H-NMR spectrum of β-glucosylated MHET

| δ [ppm] | Assignment | Relative integral | Multiplicity | Coupling ratio J [Hz] |
|---|---|---|---|---|
| 8.09 | H-3", H-4", H-6", H-7" | 4H | 2 doublets | 8.66 |
| 4.58-4.48 | H-2 | 2H | Multiplet | |
| 4.37 | H-1 | 1H | Doublet | 7.76 |
| 4.22 | H-1'a | 1H | Doublet of the doublet of the doublet | 11.65 5.87 3.53 |
| 3.96 | H-1'b | 1H | Doublet of the doublet of the doublet | 11.65 5.87 3.65 |
| 3.86 | H-6a | 1H | Multiplet | |
| 3.68-3.64 | H-6b | 1H | Multiplet | |
| 3.36 | H-3 | 1H | Tripplet | 9.02 |
| 3.32-3.28 | H-4, H-5. | 2H | Multiplet | |
| 3.22 | H-2 | 1H | Doublet of the doublet | 9.02 7.76 |

TABLE 4

Signal assignment $^{13}$C-NMR spectrum of β-glucosylated MHET

| δ [ppm] | Assignment |
|---|---|
| 167.50 | C-1", C-8" |
| 134.17 | C-2", C-5" |
| 130.52 | C-3", C-4", |
| 130.50 | C-6", C-7" |
| 104.68 | C-1 |
| 78.04 | C-5 |
| 77.99 | C-3 |
| 75.01 | C-2 |
| 71.55 | C-4 |
| 68.62 | C-1' |
| 65.75 | C-2' |
| 62.71 | C-6 |

Di-1,3-β-glucosylated MHET

Figure 18:
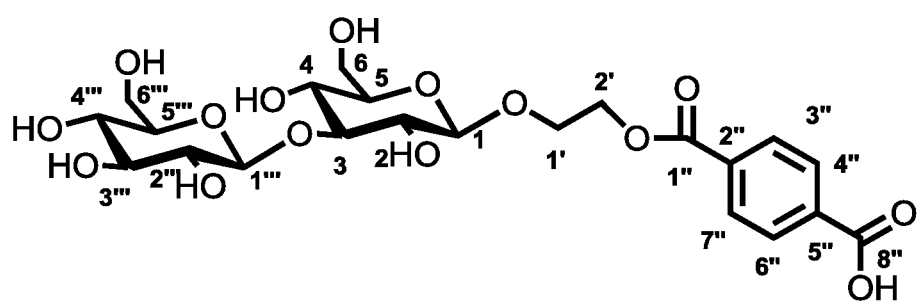
FIG. 18: Exemplary representation of the structure of Di-1,3-β-glucosylated MHET.

MS (ESI, positive): calculated for $C_{22}H_{30}NaO_{15}$ (M-H)⁻ 557.1482; according to 557.1477. Di-1,3β-glucosylated MHET is shown as an example in FIG. 18. Further test results are shown in the following tables.

TABLE 5

Signal assignment ¹H-NMR spectrum of Di-1,3-β-glucosylated MHET

| δ [ppm] | Assignment | Relative integral | Multiplicity | Coupling ratio J [Hz] |
|---|---|---|---|---|
| 8.09-8.03 | H-3", H-4", H-6", H-7" | 4H | 2 doublets | 8.66 |

TABLE 5-continued

Signal assignment $^1$H-NMR spectrum of Di-1,3-β-glucosylated MHET

| δ [ppm] | Assignment | Relative integral | Multiplicity | Coupling ratio J [Hz] |
|---|---|---|---|---|
| 4.57 | H-1''' | 1H | Doublet | 7.68 |
| 4.57-4.50 | H-2' | 2H | Multiplet | |
| 4.44 | H-1 | 1H | Doublet | 7.88 |
| 4.25-4.18 | H-1'a | 1H | Multiplet | |
| 4.00-3.94 | H-1'b | 1H | Multiplet | |
| 3.88 | H-6'''a | 1H | Doublet of the doublet | 11.92 6.44 |
| 3.88 | H-6a | 1H | Doublet of the doublet | 11.78 6.54 |
| 3.69 | H-6b | 1H | Doublet of the doublet | 11.86 5.46 |
| 3.64 | H-6'''b | 1H | Doublet of the doublet | 11.76 6.16 |
| 3.57 | H-3 | 1H | Triplet | 8.57 |
| 3.45-3.21 | H-2, H-2''', H-3''', H-4, H-4''', H-5, H-5''' | 7H | Multiplet | |

TABLE 6

Signal assignment $^{13}$C-NMR spectrum of Di-1,3-β-glucosylated MHET

| δ [ppm] | Assignment |
|---|---|
| 167.69 | C-1'', C-8'' |
| 133.39 | C-2'', C-5'' |
| 130.34 | C-3'', C-4'', C-6'', C-7'' |
| 105.21 | C-1''' |
| 104.20 | C-1 |
| 87.77 | C-3 |
| 78.13 | C-5''' |
| 77.73 | C-5 |
| 77.65 | C-4''' |
| 75.47 | C-2''' |
| 74.37 | C-3 |
| 71.51 | C-4 |
| 69.95 | C-2 |
| 68.65 | C-1' |
| 65.62 | C-2' |
| 62.56 | C-6, C-6''' |

(4) Production of β-galactosylated MHET

MHET (0.05 mol/l) and cellobiose (0.4 mol/l) are dissolved in sodium acetate buffer (0.05 mol/l, pH=5.2) or phosphate buffer (0.05 mol/l, pH=7) and a β-glucosidase solution (100 U in sodium acetate buffer or phosphate buffer) is added. Lactose consists of D-galactose and D-glucose, which are linked by a β-1,4-glycosidic bond. β-galactosidase enzymatically catalyses the hydrolysis of this bond, producing galactose, which chemically binds to the MHET during the reaction.

Figure 19:
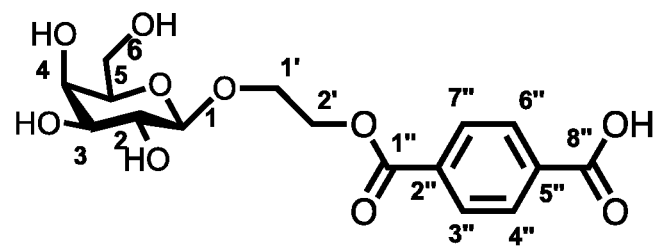
FIG. 19: Exemplary representation of the structure of β-galactosylated MHET.

For this purpose, the reaction mixture is shaken at a temperature of 37° C. in a water bath. After optimal product formation, the reaction is terminated. The product β-galactosylated MHET is isolated by column chromatography.

β-galactosylated MHET is shown in FIG. 19 as an example. The test results of the embodiment with sodium acetate buffer are as follows.

The product is confirmed by mass spectrometry (MT206).

Figure 20:
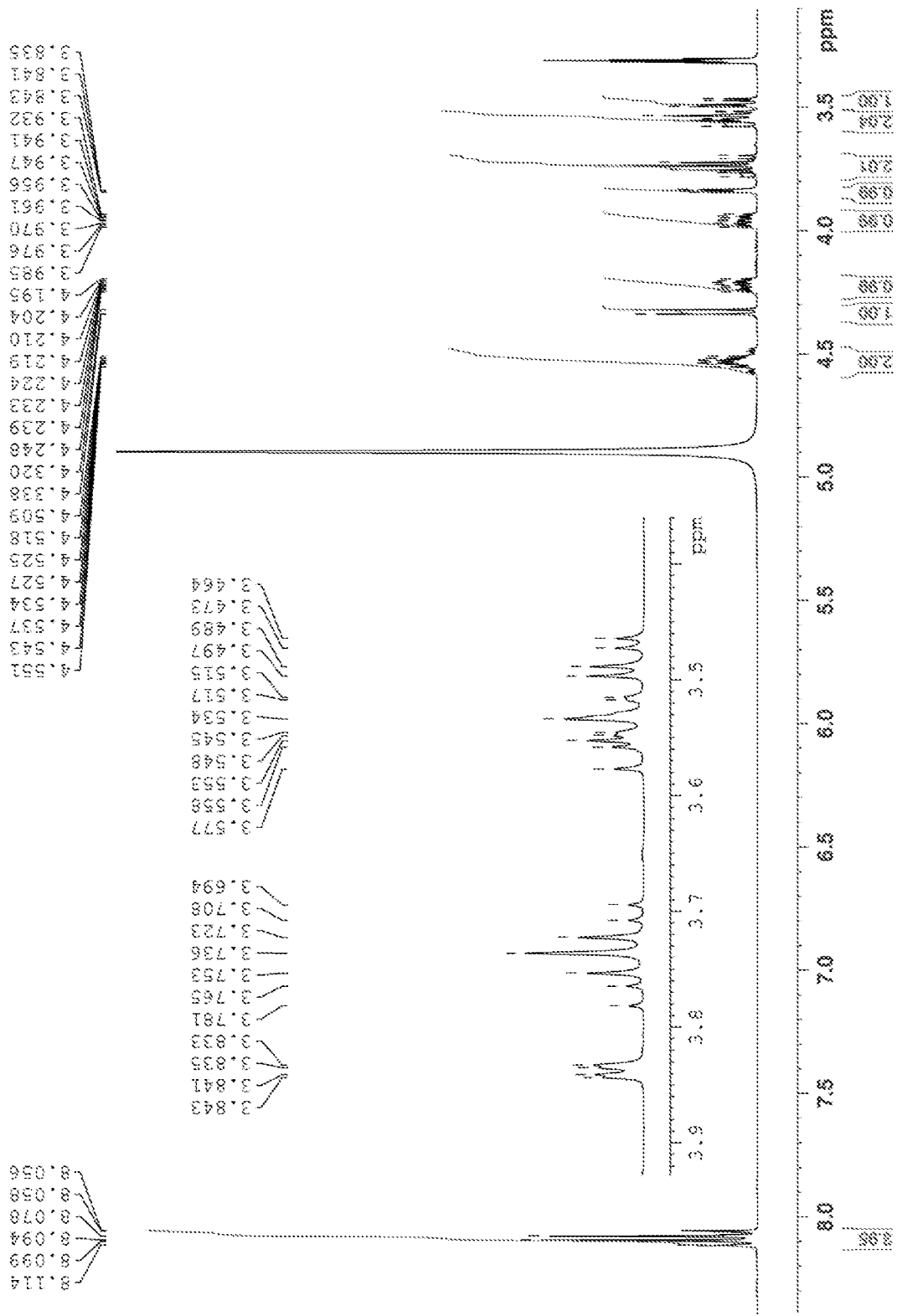
FIG. 20: $^1$H-NMR spectrum of β-galactosylated MHET.
Figure 21:
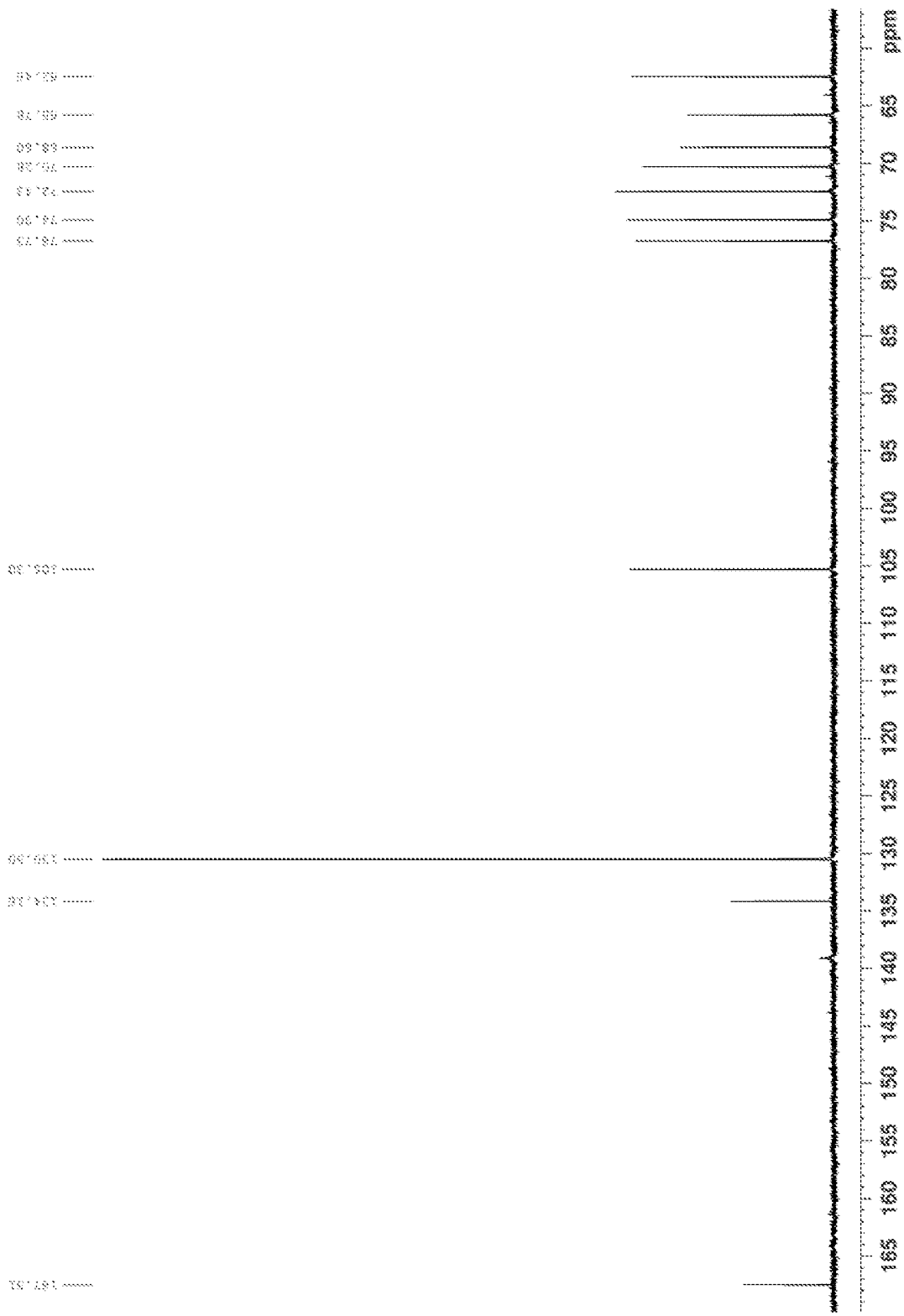
FIG. 21: $^{13}$C-NMR spectrum of β-galactosylated MHET.

MS (ESI, negative): calculated for $C_{16}H_{19}O_{10}$ (M-H)$^-$ 371.0978; according to 371.0975. Further test results are shown in FIG. 20, FIG. 21 and the following tables.

TABLE 7

Signal assignment $^1$H-NMR spectrum of β-galactosylated MHET

| δ [ppm] | Assignment | Relative integral | Multiplicity | Coupling ratio J [Hz] |
|---|---|---|---|---|
| 8.09 | H-3'', H-4'', H-6'', H-7'' | 4H | 2 doublets | 8.67 |
| 4.53 | H-2' | 2H | Multiplet | |
| 4.33 | H-1 | 1H | Doublet | 7.52 |
| 4.22 | H-1'a | 1H | Multiplet | |
| 3.96 | H-1'b | 1H | Multiplet | |
| 3.84 | H-4 | 1H | Doublet of the doublet | 3.32 0.92 |
| 3.76 | H-6a | 1H | Multiplet | |
| 3.72 | H-6b | 1H | Multiplet | |
| 3.56 | H-2 | 1H | Doublet of the doublet | 9.72 7.52 |
| 3.56-3.51 | H-3 | 1H | Multiplet | |
| 3.48 | H-5 | 1H | Doublet of the doublet | 9.72 3.32 |

TABLE 8

Signal assignment $^{13}$C-NMR spectrum of β-galactosylated MHET

| δ [ppm] | Assignment |
|---|---|
| 167.51 | C-1'', C-8'' |
| 134.16 | C-2'', C-5'' |
| 130.50 | C-3'', C-4'', C-6'', C-7'' |
| 105.30 | C-1 |
| 76.73 | C-3 |
| 74.90 | C-5 |
| 72.43 | C-2 |
| 70.28 | C-4 |
| 68.60 | C-1' |
| 65.78 | C-2 |
| 62.46 | C-6 |

(5) Production of Fructosylated MHET

MHET (0.05 mol/l) and sucrose (0.4 mol/l) were dissolved in sodium acetate buffer (0.05 mol/l, pH=5.2) and a fructosidase solution (100 U in sodium acetate buffer) was added.

The fructosidase solution enzymatically catalyses the cleavage of sucrose into α-D-glucose and β-D-fructose. The β-D-fructose chemically binds to the MHET during the reaction. For this purpose, the reaction mixture is also shaken at a temperature of 37° C. in a water bath. After optimal product formation, the reaction is terminated.

(6) Production of α-glucosylated bis(2-hydroxyethyl)terephthalate

Bis(2-hydroxyethyl)terephthalate (0.05 mol/l) and sucrose (0.4 mol/l) are dissolved in 0.05 M phosphate buffer (0.05 mol/l, pH=7) or are dissolved in 0.05 M phosphate buffer (0.05 mol/l, pH=6) dissolved and a suspension of microorganisms (*Protaminobacter rubrum* Z 12 (CBD 574.77)) is added. In an alternative embodiment example, α-glucosidase solution (100 U in phosphate buffer) is added.

Sucrose consists of α-D-glucose and β-D-fructose, which are linked via an α,β-1,2-glycosidic bond. The microorganism *Protaminobacter rubrum* Z 12 contains an enzyme, an α-glucosidase. It catalyses the cleavage of the used sucrose into α-D-glucose and β-D-fructose. The α-D-glucose chemically binds to the bis(2-hydroxyethyl)terephthalate during the reaction.

Figure 22:
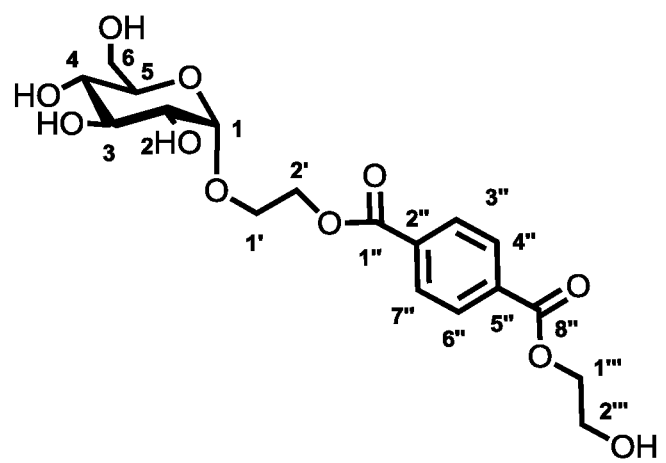
FIG. 22: Example of the structure of α-glucosylated bis(2-hydroxyethyl)terephthalate.
Figure 23:
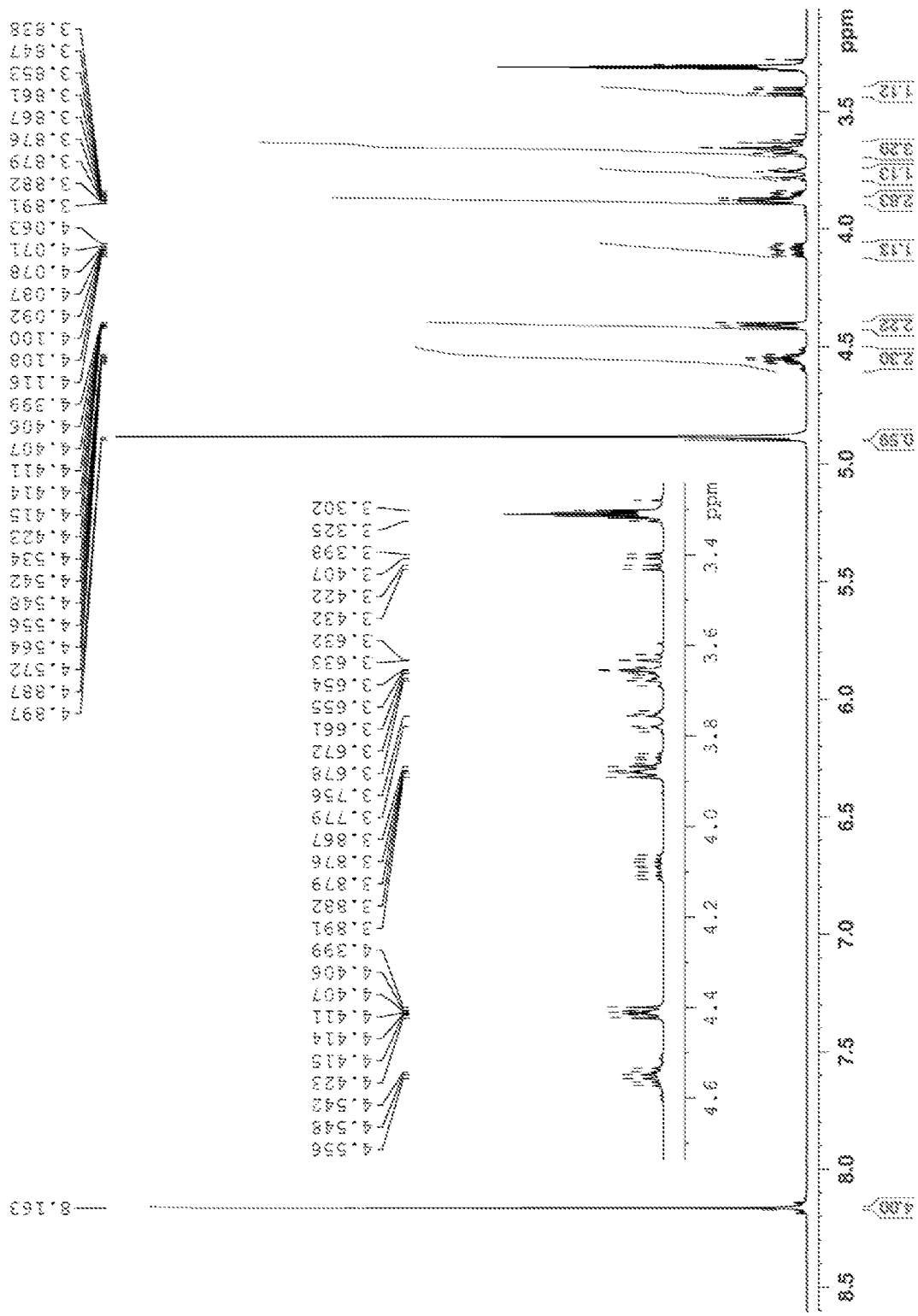
FIG. 23: $^1$H-NMR spectrum of α-glucosylated bis(2-hydroxyethyl)terephthalate.
Figure 24:
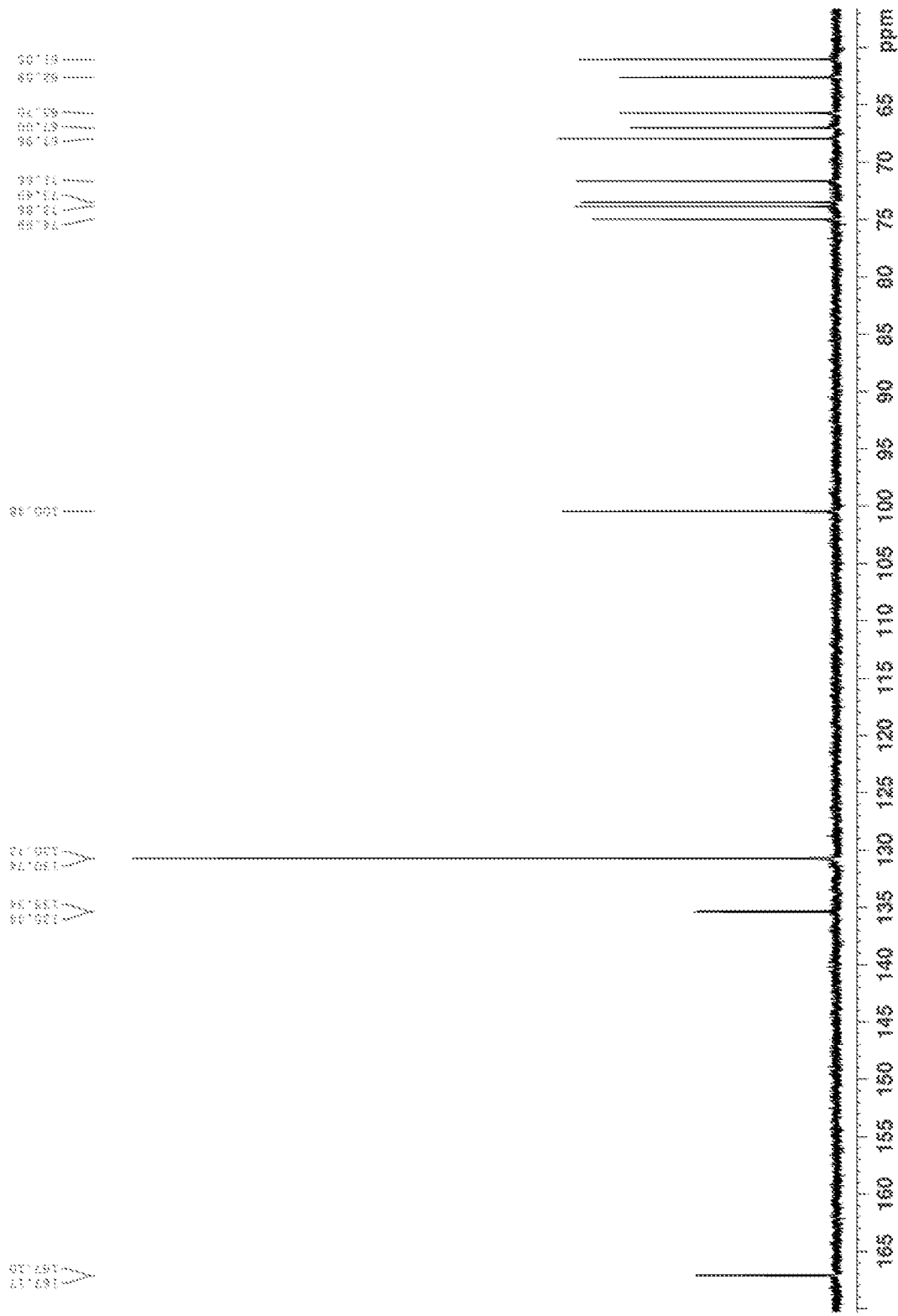
FIG. 24: $^{13}$C-NMR spectrum of α-glucosylated bis(2-hydroxyethyl)terephthalate.

For this purpose, the reaction mixture is shaken at a temperature of 37° C. in a water bath. After optimal product formation, the reaction is terminated. The product α-glycosylated bis(2-hydroxyethyl)terephthalate is obtained. Optimal product formation is determined by continuous sampling and thin-layer chromatography. α-glucosylated bis(2-hydroxyethyl)terephthalate is shown as an example in FIG. 22. Test results of the embodiment with 0.05 M phosphate buffer (0.05 mol/l, pH=6) and a suspension of microorganisms (*Protaminobacter rubrum* Z 12 (CBD 574.77)) are shown in FIG. 23, FIG. 24 and in the following tables.

TABLE 9

Signal assignment $^1$H-NMR spectrum of α-glucosylated bis(2-hydroxyethyl)terephthalate

| δ [ppm] | Assignment | Relative integral | Multiplicity | Coupling ratio J [Hz] |
|---|---|---|---|---|
| 8.16 | H-3", H-4", H-6", H-7" | 4H | Singlet | |
| 4.89 | H-1 | 1H | Doublet | 3.96 |
| 4.57-4.53 | H-2''' | 2H | Multiplet | |
| 4.41 | H-1''' | 2H | Multiplet | |
| 4.09 | H-1'a | 1H | Multiplet | |
| 3.87 | H-2' | 2H | Multiplet | |
| 3.88-3.84 | H-1'b | 1H | Multiplet | |
| 3.79-3.74 | H-6a | 1H | Multiplet | |
| 3.69-3.62 | H-3, H-4, H-6b | 3H | Multiplet | |
| 3.41 | H-2 | 1H | Doublet of the doublet | 9.72 3.76 |
| 3.30 | H-5 | 1H | Multiplet | |

TABLE 10

Signal assignment $^{13}$C-NMR spectrum of α-glucosylated bis(2-hydroxyethyl)terephthalate

| δ [ppm] | Assignment |
|---|---|
| 167.17 | C-1", C-8" |
| 167.10 | |
| 135.44 | C-2", C-5" |
| 135.34 | |
| 130.74 | C-3", C-4", C-6", C-7" |
| 130.73 | |
| 100.48 | C-1 |
| 74.99 | C-4 |
| 73.86 | C-3 |
| 73.49 | C-2 |
| 71.66 | C-5 |
| 67.96 | C-1''' |
| 67.00 | C-1' |
| 65.70 | C-2''' |
| 62.59 | C-6 |
| 61.05 | C-2' |

Di-α-1,6-glucosylated bis(2-hydroxyethyl)terephthalate

Figure 25:
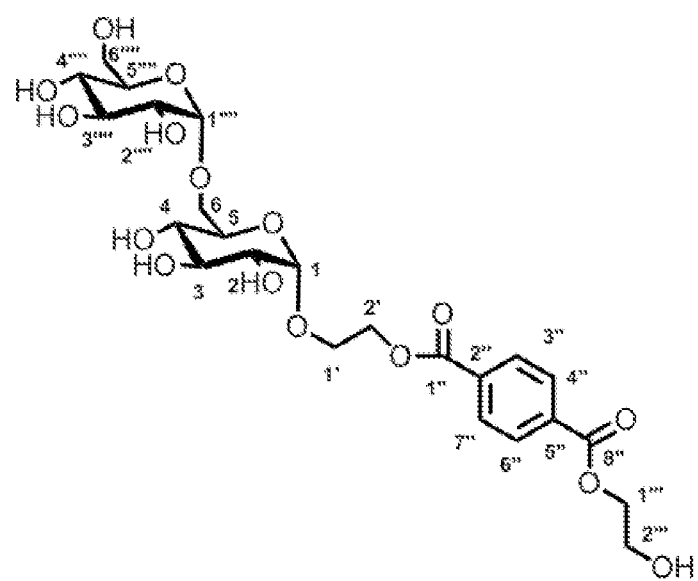
FIG. 25: Exemplary representation of the structure of di-α-1,6-glucosylated bis(2-hydroxyethyl)terephthalate.
Figure 26:
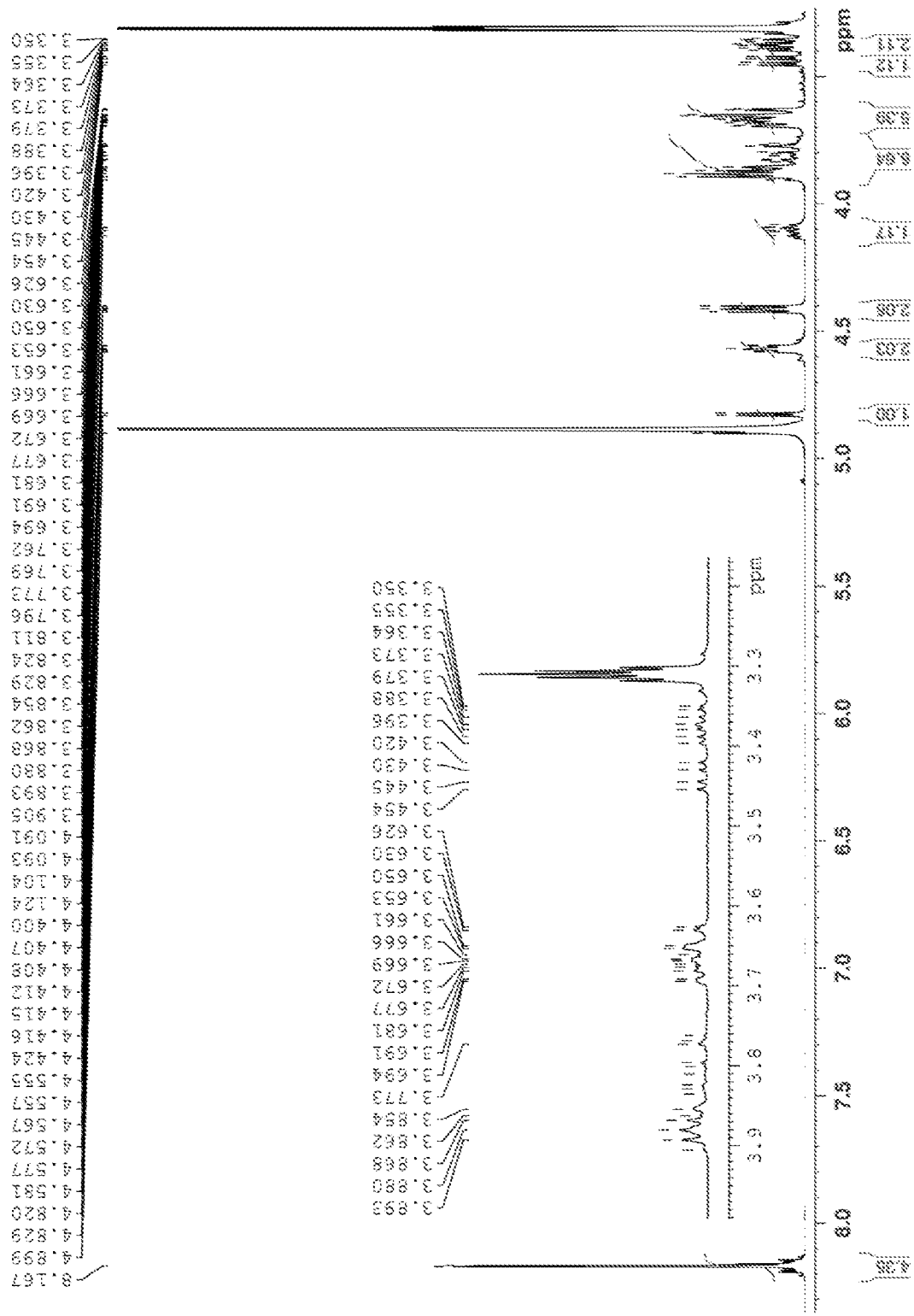
FIG. 26: $^1$H-NMR spectrum of di-α-1,6-glucosylated bis(2-hydroxyethyl)terephthalate.
Figure 27:
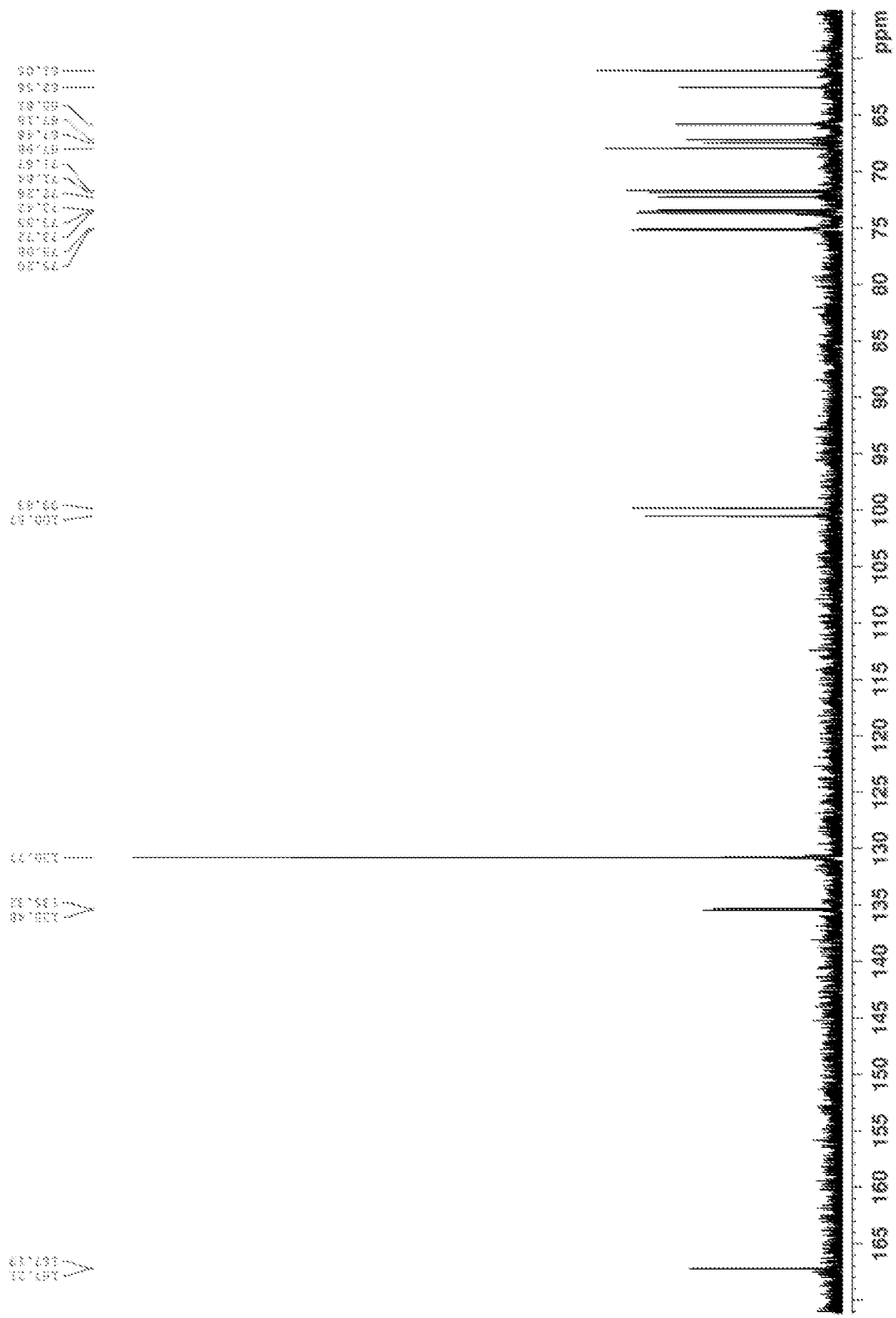
FIG. 27: $^{13}$C-NMR spectrum of di-α-1,6-glucosylated bis(2-hydroxyethyl)terephthalate.

Di-α-1,6-glucosylated bis(2-hydroxyethyl)terephthalate is shown in FIG. 25 as an example. Further test results are shown in FIG. 26, FIG. 27 and the following tables.

TABLE 11

Signal assignment $^1$H-NMR spectrum of Di-α-1,6-glucosylated bis(2-hydroxyethyl)terephthalate

| δ [ppm] | Assignment | Relative integral | Multiplicity | Coupling ratio J [Hz] |
|---|---|---|---|---|
| 8.17 | H-3", H-4", H-6", H-7" | 4H | Singlet | |
| 4.90 | H-1 | 1H | Doublet | |
| 4.82 | H-1'''' | 1H | Doublet | 3.68 |
| 4.57 | H-2' | 2H | Triplet | 5.24 |
| 4.41 | H-1''' | 2H | Triplet | 4.80 |

TABLE 11-continued

Signal assignment $^1$H-NMR spectrum of Di-α-1,6-glucosylated bis(2-hydroxyethyl)terephthalate

| δ [ppm] | Assignment | Relative integral | Multiplicity | Coupling ratio J [Hz] |
|---|---|---|---|---|
| 4.08 | H-1'a | 1H | Doublet of the doublet of the doublet | 11.74 5.56 4.04 |
| 3.91-3.82 | H-1'a, H-6a, H-2''', H-4, H-6''''a | 5H | Multiplet | |
| 3.69-3.63 | H-3, H-3'''', H-4, H-6b, H-6''''b | 5H | Multiplet | |
| 3.43 | H-2 | 1H | Doublet of the doublet | 9.70 3.78 |
| 3.73 | H-5'''' | 1H | Triplet | 9.26 |
| 3.21 | H-2'''' | 1H | Doublet of the doublet | 9.06 7.78 |
| 3.31 | H-5 | 1H | | MeOH |

TABLE 12

Signal assignment $^{13}$C-NMR spectrum of Di-α-1,6-glucosylated bis(2-hydroxyethyl)terephthalate

| δ [ppm] | Assignment |
|---|---|
| 167.21 | C-1", C-8" |
| 167.19 | |
| 135.48 | C-2", C-5" |
| 135.23 | |
| 130.77 | C-3", C-4", C-6", C-7" |
| 100.57 | C-1 |
| 99.83 | C-1'''' |
| 75.20 75.08 | C-3, C-3'''' |
| 73.72 | C-2''' |
| 73.55 | C-4'''' |
| 73.42 | C-2'''' |
| 72.26 | C-4 |
| 71.84 | C-5'''' |
| 71.67 | C-5 |
| 67.98 | C-1''' |
| 67.48 | C-6 |
| 67.18 | C-1' |
| 62.56 | C-6'''' |
| 61.05 | C-2''' |

(7) Production of β-glucosylated bis(2-hydroxyethyl)terephthalate

Bbis(2-hydroxyethyl)terephthalate (0.05 mol/l) and cellobiose (0.4 mol/l) are dissolved in sodium acetate buffer (0.05 mol/l, pH=5.2) and a β-glucosidase solution (100 U in sodium acetate buffer) is added. Cellobiose is a disaccharide consisting of two glucose molecules linked together by β-1,4-glucoside. The enzyme β-glucosidase enables the degradation of cellobiose to glucose. The glucose chemically binds to the bis(2-hydroxyethyl)terephthalate during the reaction.

Figure 28:
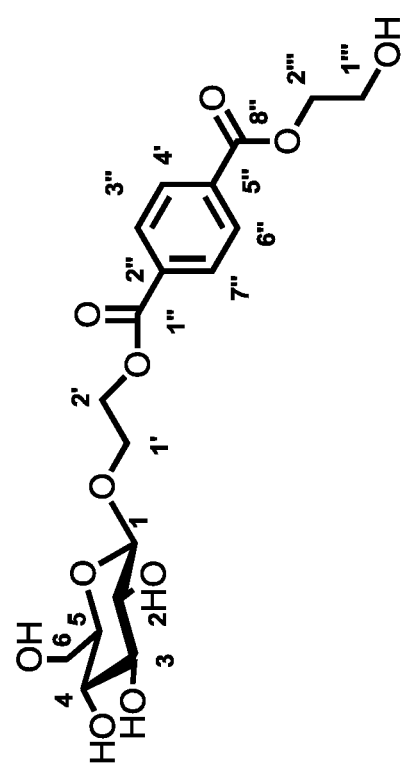
FIG. 28: Example of the structure of β-glucosylated bis(2-hydroxyethyl)terephthalate.
Figure 29:
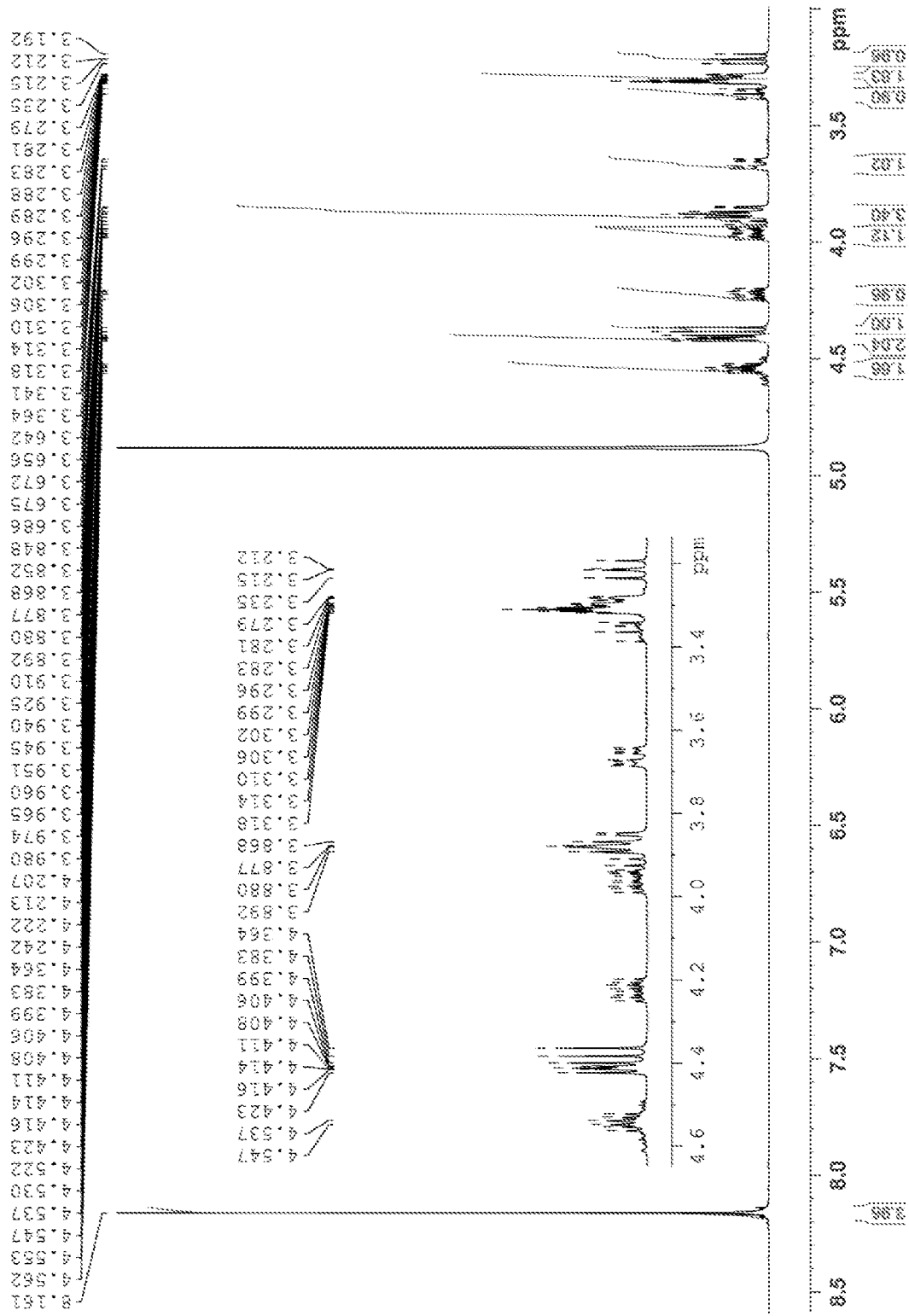
FIG. 29: $^1$H-NMR spectrum of β-glucosylated bis(2-hydroxyethyl)terephthalate.
Figure 30:
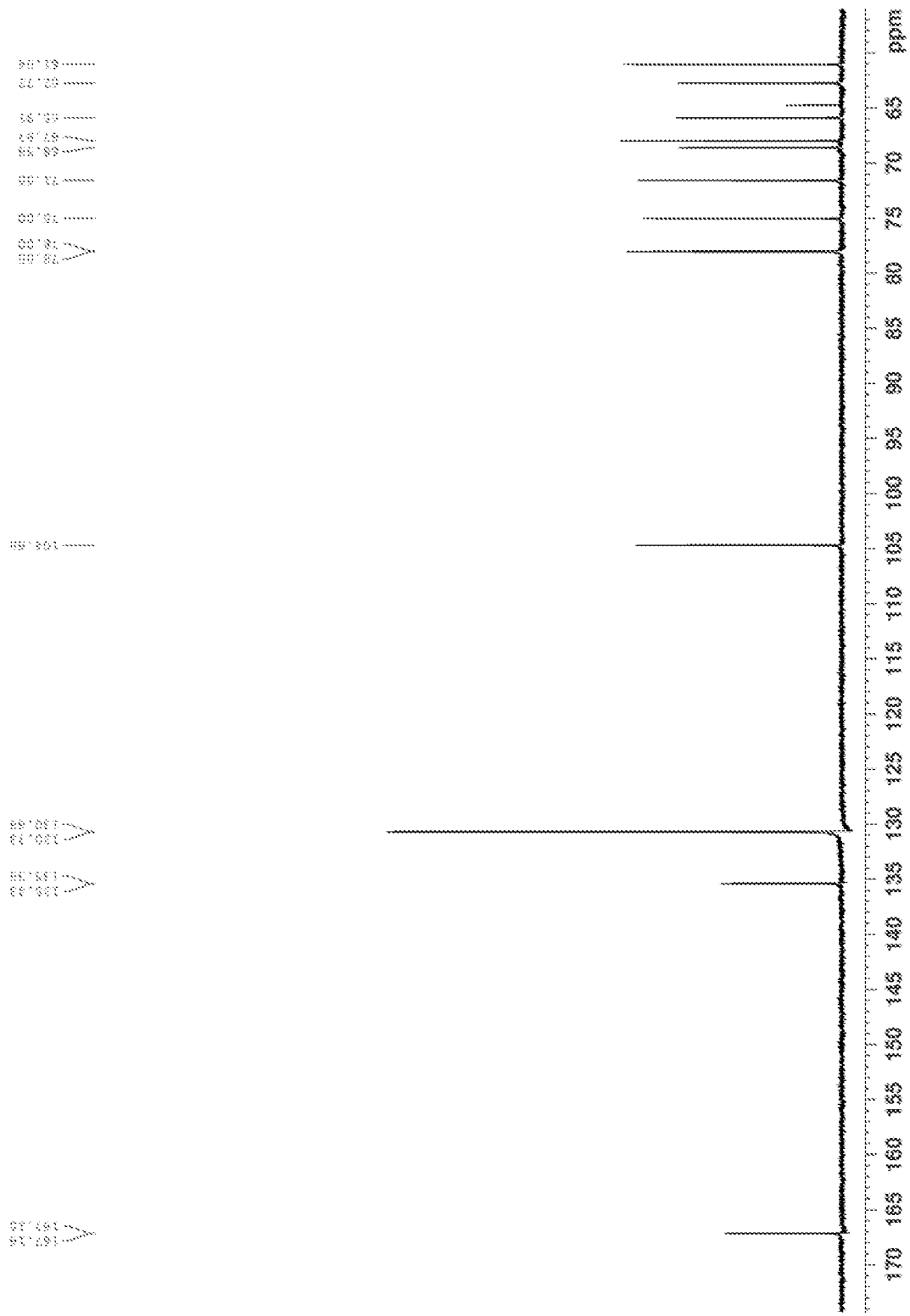
FIG. 30: $^{13}$C-NMR spectrum of β-glucosylated bis(2-hydroxyethyl)terephthalate.

The reaction mixture is also shaken at a temperature of 37° C. in a water bath. After optimal product formation, the reaction is terminated. After column chromatography, 3-glucosylated bis(2-hydroxyethyl)terephthalate is obtained (see FIG. 28). Further test results are shown in FIG. 29, FIG. 30 and the following tables.

TABLE 13

Signal assignment $^1$H-NMR spectrum of β-glucosylated bis(2-hydroxyethyl)terephthalate

| δ [ppm] | Assignment | Relative integral | Multiplicity | Coupling ratio J [Hz] |
|---|---|---|---|---|
| 8.16 | H-3", H-4", H-6", H-7" | 4H | Singlet | |
| 4.56-4.52 | H-2' | 2H | Multiplet | |
| 4.41 | H-2''' | 2H | Multiplet | |
| 4.37 | H-1 | 1H | Triplet | 7.76 |
| 4.22 | H-1'a | 1H | Doublet of the doublet of the doublet | 11.72 5.88 3.54 |
| 3.99-3.94 | H-1'b | 1H | Multiplet | |
| 3.88 | H-1''' | 2H | Triplet | 4.80 |
| 3.87-3.85 | H-6a | 1H | Multiplet | |
| 3.69-3.64 | H-6b | 1H | Multiplet | |
| 3.36 | H-3 | 1H | Triplet | 9.02 |
| 3.30-3.28 | H-4 | 1H | Multiplet | |
| 3.21 | H-2 | 1H | Doublet of the doublet | 9.06 7.78 |

TABLE 14

Signal assignment $^{13}$C-NMR spectrum of β-glucosylated bis(2-hydroxyethyl) terephthalate

| δ [ppm] | Assignment |
|---|---|
| 167.16 | C-1", C-8" |
| 167.15 | |
| 135.43 | C-2", C-5" |
| 135.38 | |
| 130.73 | C-3", C-4", |
| 130.68 | C-6", C-7" |
| 104.68 | C-1 |
| 78.05 | C-4 |
| 78.00 | C-3 |
| 75.00 | C-2 |
| 71.55 | C-5 |
| 68.58 | C-2' |
| 67.97 | C-2''' |
| 65.91 | C-1' |
| 62.72 | C-6 |
| 61.04 | C-1''' |

(8) Production of β-galactosylated bis(2-hydroxyethyl)terephthalate

Bis(2-hydroxyethyl)terephthalate (0.05 mol/l) and lactose (0.4 mol/l) are dissolved in sodium acetate buffer (0.05 mol/l, pH=5.2) or phosphate buffer (0.05 mol/l, pH=7) and a β-galactosidase solution (100 U in sodium acetate buffer or phosphate buffer) is added. Lactose consists of D-galactose and D-glucose, which are linked by a β-1,4-glycosidic bond. β-galactosidase enzymatically catalyses the hydrolysis of this bond, producing galactose, which chemically binds to bis(2-hydroxyethyl)terephthalate during the reaction.

Figure 31:
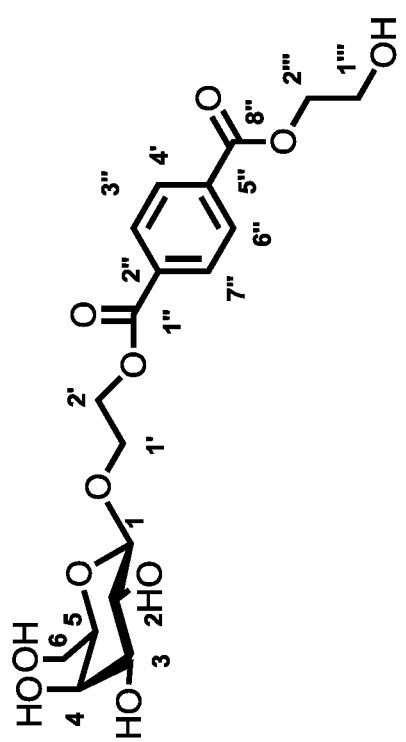
FIG. 31: Example of the structure of β-galactosylated bis(2-hydroxyethyl)terephthalate.
Figure 32:
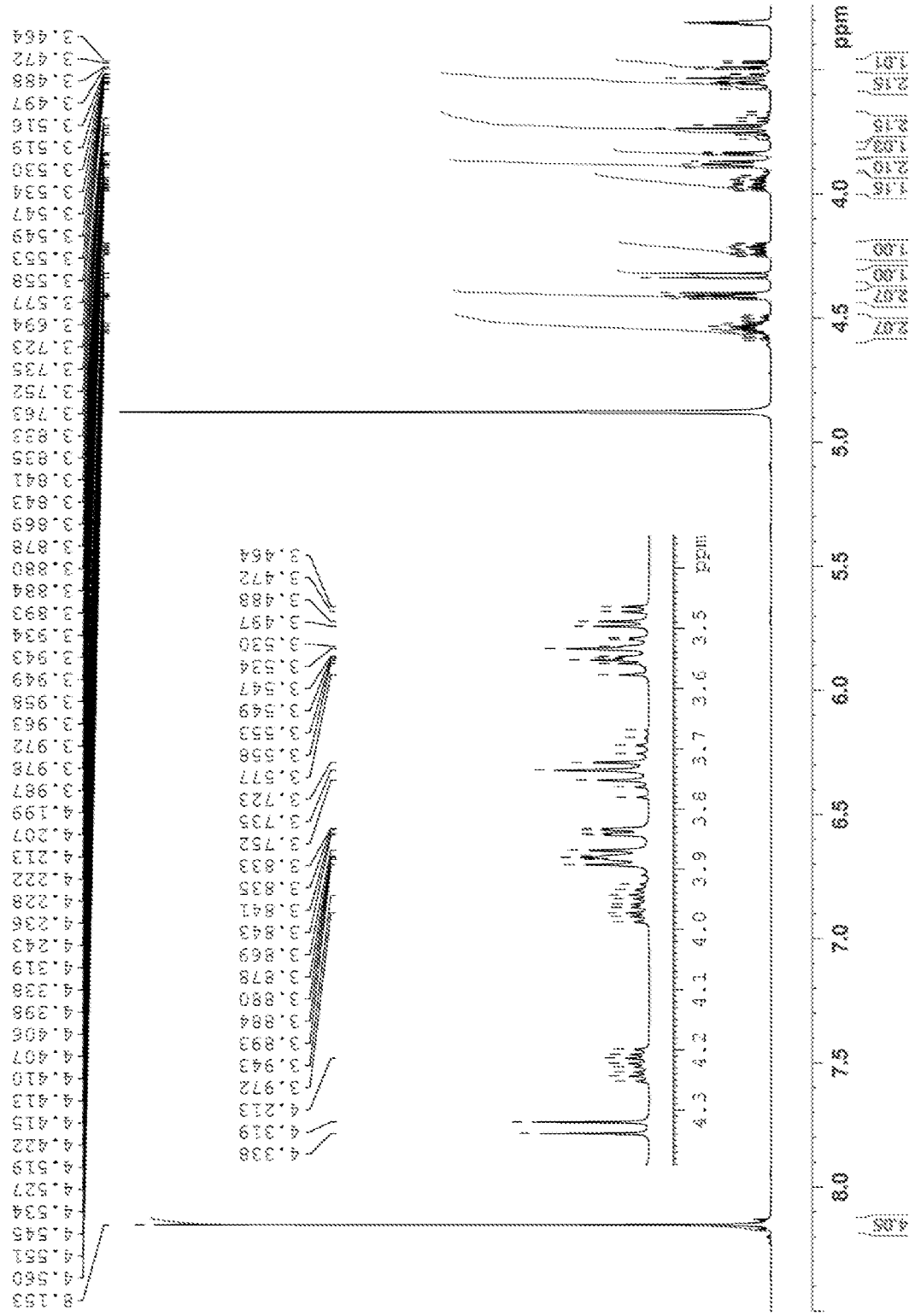
FIG. 32: $^1$H-NMR spectrum of β-galactosylated bis(2-hydroxyethyl)terephthalate.
Figure 33:
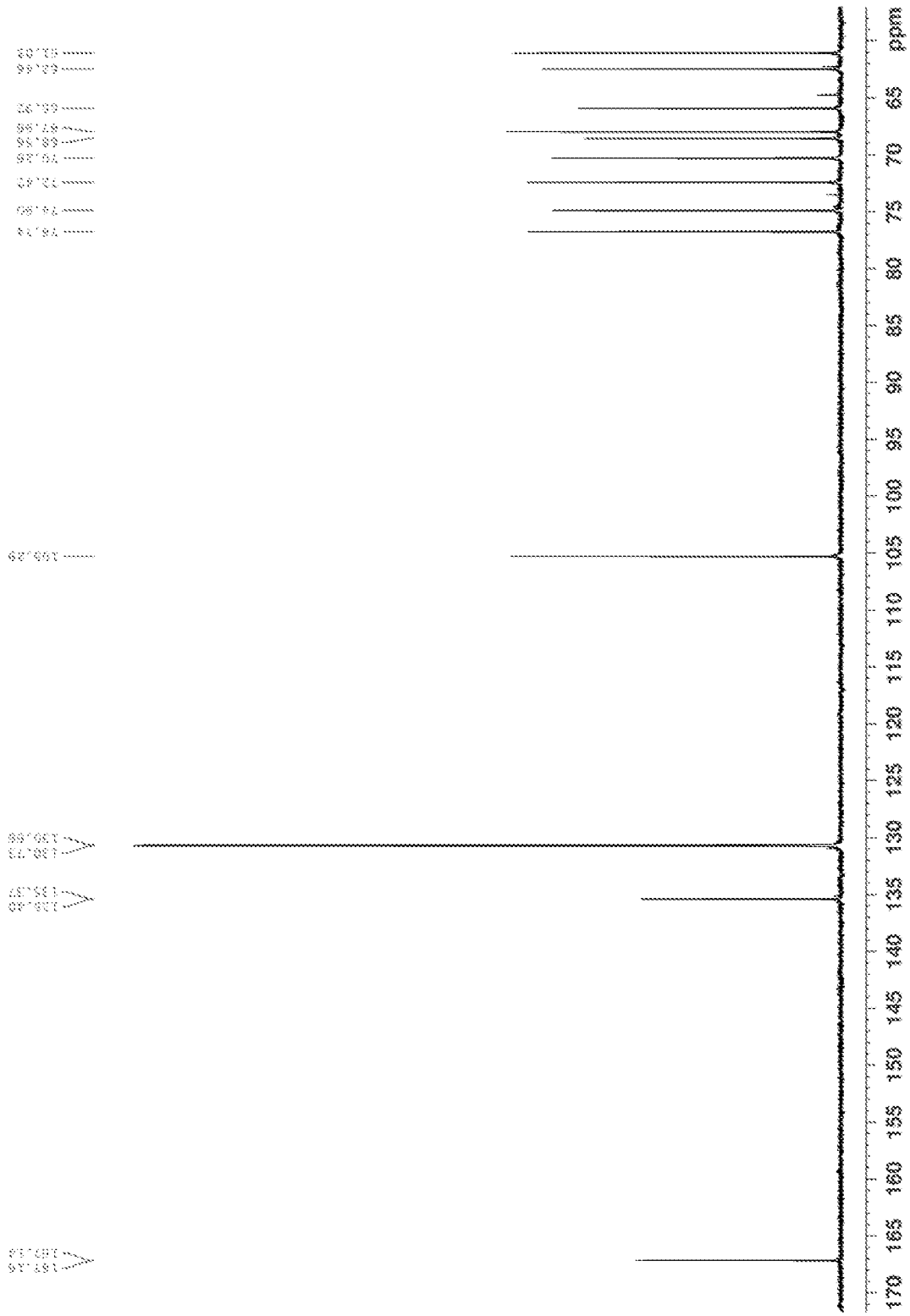
FIG. 33: $^{13}$C-NMR spectrum of β-galactosylated bis(2-hydroxyethyl)terephthalate.

For this purpose, the reaction mixture is also shaken at a temperature of 37° C. in a water bath. After optimal product formation, the reaction is terminated. The product 3-galactosylated bis(2-hydroxyethyl)terephthalate is isolated by column chromatography.

β-galactosylated bis(2-hydroxyethyl)terephthalate is shown as an example in FIG. 31. Test results of the embodiment with sodium acetate buffer are shown in FIG. 32, FIG. 33 and in the following tables.

TABLE 15

Signal assignment $^1$H-NMR spectrum of β-galactosylated bis(2-hydroxyethyl)terephthalate

| δ [ppm] | Assignment | Relative integral | Multiplicity | Coupling ratio J [Hz] |
|---|---|---|---|---|
| 8.15 | H-3", H-4", H-6", H-7" | 4H | Singlet | |
| 4.54 | H-2 | 2H | Multiplet | |
| 4.41 | H-2''' | 1H | Multiplet | |
| 4.31 | H-1 | 1H | Doublet | 7.60 |
| 4.23 | H-1'a | 1H | Multiplet | |
| 3.96 | H-1'b | 1H | Multiplet | |
| 3.89-3.87 | H-1''' | 2H | Multiplet | |
| 3.84 | H-4 | 1H | Doublet of the doublet | 3.30 0.94 |
| 3.78-3.68 | H-6 | 2H | Multiplet | |
| 3.56 | H-2 | 1H | Doublet of the doublet | 9.80 7.60 |
| 3.55-3.52 | H-5 | 1H | Multiplet | |
| 3.48 | H-3 | 1H | Doublet of the doublet | 9.70 3.34 |

TABLE 16

Signal assignment $^{13}$C-NMR spectrum of β-galactosylated bis(2-hydroxyethyl) terephthalate

| δ [ppm] | Assignment |
|---|---|
| 167.16 | C-1", C-8" |
| 167.14 | |
| 135.40 | C-2", C-5" |
| 135.37 | |
| 130.73 | C-3", C-4", |
| 130.66 | C-6", C-7" |
| 105.29 | C-1 |
| 76.74 | C-5 |
| 74.90 | C-3 |
| 72.42 | C-2 |
| 70.26 | C-4 |
| 68.56 | C-1' |
| 67.96 | C-2''' |
| 65.92 | C-2 |
| 62.46 | C-6 |
| 61.03 | C-1''' |

Di-β-galactosylated bis(2-hydroxyethyl)terephthalate

MS (ESI, positive): calculated for $C_{24}H_{34}NaO_{16}$ (M-H)$^-$ 601.1745; according to 601.1739.

Di-β-glucosylated bis(2-hydroxyethyl)terephthalate

Figure 34:
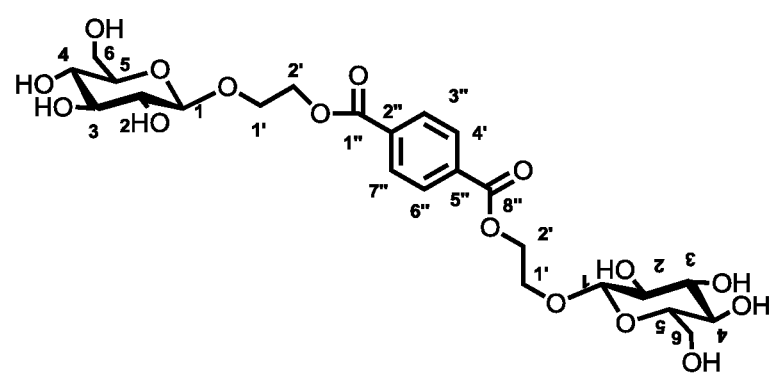
FIG. 34: Exemplary representation of the structure of Di-β-glucosylated bis(2-hydroxyethyl)terephthalate.

Di-β-glucosylated bis(2-hydroxyethyl)terephthalate is shown as an example in FIG. 34.

The product is confirmed by mass spectrometry.

MS (ESI, positive): calculated for $C_{24}H_{34}O_{16}Na$ (M-H)$^+$ 601.1745, according to 601.1739.

Figure 35:
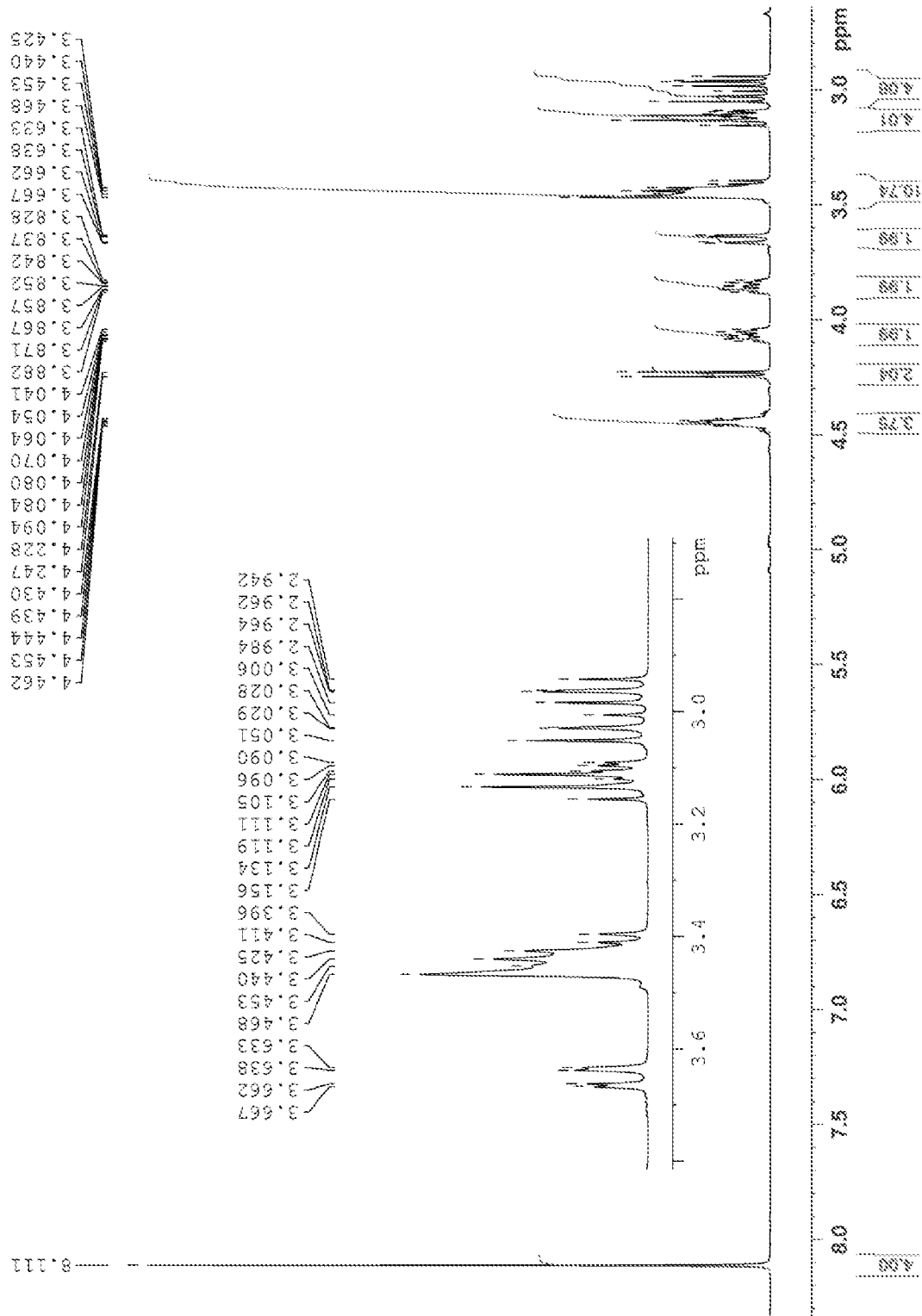
FIG. 35: $^1$H-NMR spectrum of Di-β-glucosylated bis(2-hydroxyethyl)terephthalate.
Figure 36:
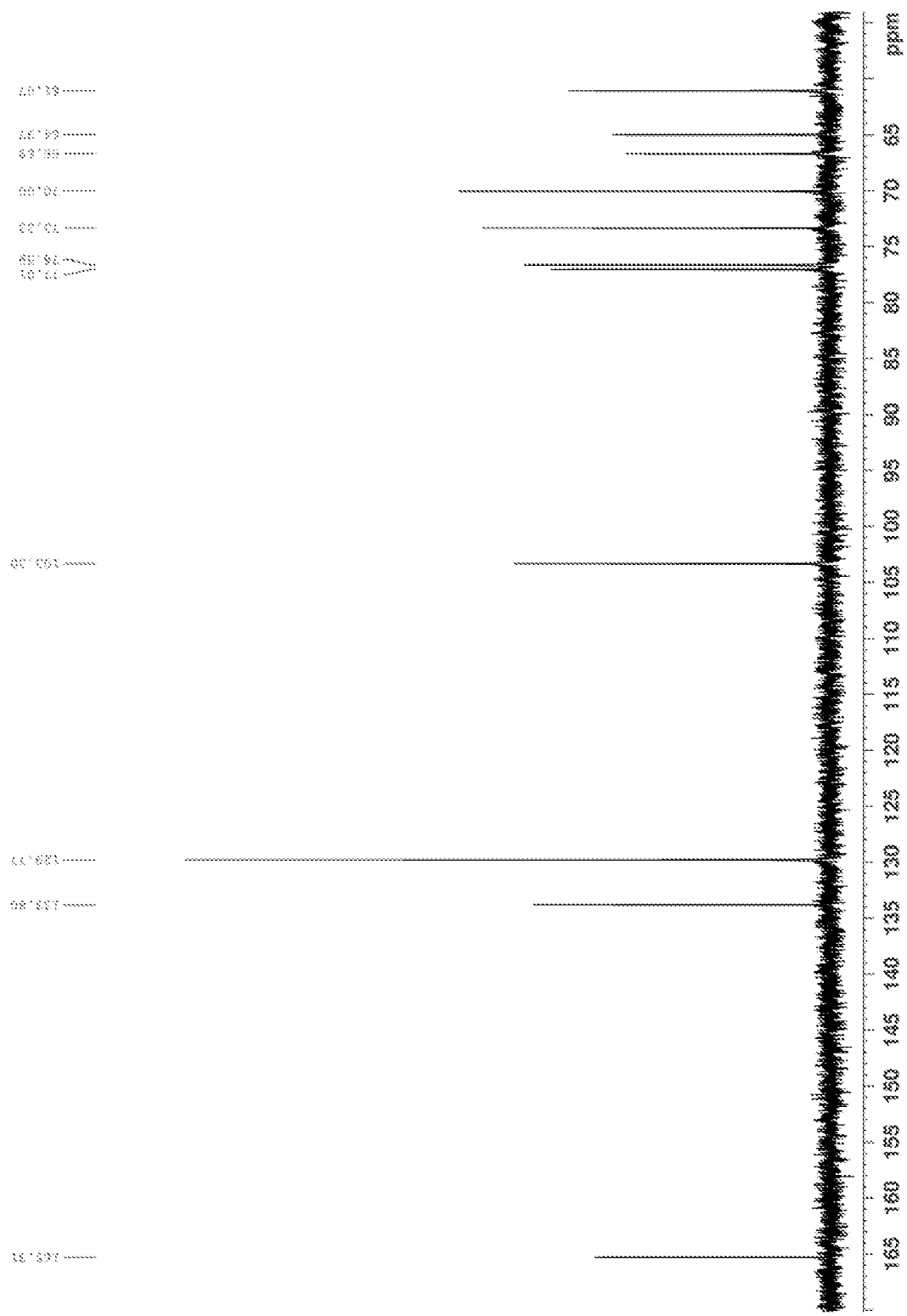
FIG. 36: $^{13}$C-NMR spectrum of Di-β-glucosylated bis(2-hydroxyethyl)terephthalate.

Further test results are shown in FIG. 35, FIG. 36 and the following tables.

TABLE 17

Signal assignment $^1$H-NMR spectrum of Di-β-glucosylated bis(2-hydroxyethyl)terephthalate

| δ [ppm] | Assignment | Relative integral | Multiplicity | Coupling ratio J [Hz] |
|---|---|---|---|---|
| 8.11 | H-3", H-4", H-6", H-7" | 4H | Singlet | |
| 4.64-4.43 | H-2' | 4H | Multiplet | |
| 4.24 | H-1 | 2H | Doublet | 7.80 |
| 4.09-4.04 | H-1'a | 2H | Multiplet | |
| 3.88-3.83 | H-1'b | 2H | Multiplet | |

TABLE 17-continued

Signal assignment ¹H-NMR spectrum of Di-β-glucosylated bis(2-hydroxyethyl)terephthalate

| δ [ppm] | Assignment | Relative integral | Multiplicity | Coupling ratio J [Hz] |
|---|---|---|---|---|
| 3.65 | H-6a | 2H | Doublet | 11.48 2.12 |
| 3.42 | H-6b | 2H | Triplet | 11.82 5.9 |
| 3.13 | H-3 | 2H | Triplet | 8.84 |
| 3.12-3.09 | H-5 | 2H | Multiplet | |
| 3.03 | H-4 | 2H | Doublet of the doublet | 9.50 8.82 |
| 2.96 | H-2 | 2H | Doublet of the doublet | 8.82 7.94 |

TABLE 18

Signal assignment ¹³C-NMR spectrum of Di-β-glucosylated bis(2-hydroxyethyl)terephthalate

| δ [ppm] | Assignment |
|---|---|
| 165.31 | C-1", C-8" |
| 133.80 | C-2", C-5" |
| 129.77 | C-3", C-4", C-6", C-7" |
| 103.30 | C-1 |
| 77.01 | C-5 |
| 76.59 | C-3 |
| 73.33 | C-2 |
| 70.00 | C-4 |
| 66.69 | C-1' |
| 64.97 | C-2' |
| 61.07 | C-6 |

(9) Production of Fructosylated BHET

BHET (0.05 mol/l) and sucrose (0.4 mol/l) were dissolved in sodium acetate buffer (0.05 mol/l, pH=5.2) and a fructosidase solution (100 U in sodium acetate buffer) was added. The fructosidase solution enzymatically catalyses the cleavage of sucrose into α-D-glucose and β-D-fructose. The β-D-fructose chemically binds to the BHET during the reaction. For this purpose, the reaction mixture is also shaken at a temperature of 37° C. in a water bath. After optimal product formation, the reaction is terminated.

MS (ESI, positive): calculated for $C_{16}H_{19}NaO_{10}$ (M-H)⁻ 439.1216; according to 439.1211.

(10) Production of Polyester from α-Glucosylated MHET

α-glucosylated MHET (20 mg) is heated to 250° C. for 50 sec. There is a gas formation. A brown-white solid remains, partially suspended and dissolved in water. Thin layer chromatography (MeOH/CH₂Cl₂) shows that a high polymer substance was formed from the substrate and is also UV-active.

Figure 37:
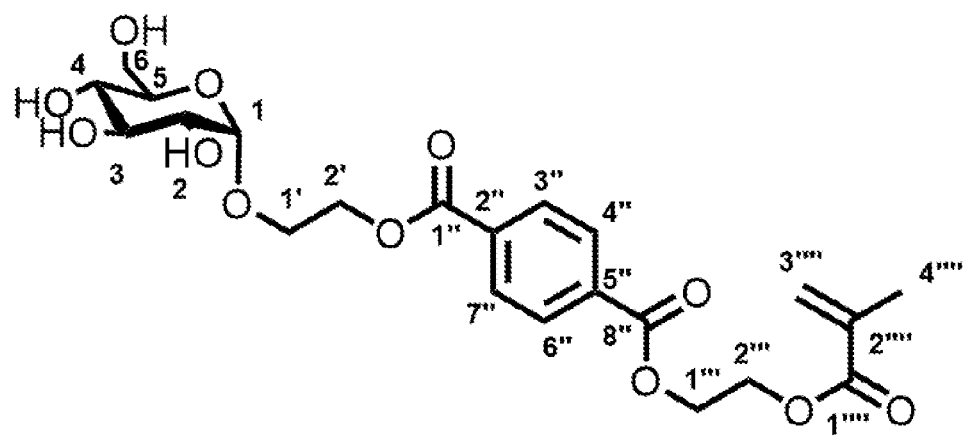
FIG. 37: Exemplary representation of the structure of glycosylated MA-BHET-α-Glc.

(11) Production of Glycosylated MA-BHET-α-Glc 40 mg α-glucosylated BHET and 72 μl vinyl methyl acrylate are dissolved in 2 ml tert-butanol. Then 25 mg Novozymes 435 are added (immobilized on acrylic resin). The suspension is shaken at 50° C. for 18 h. The suspension is then centrifuged, the supernatant is decanted and constricted at the rotary evaporator. The residue is chromatographed on silica gel 60 (Macherey Nagel, 0.044-0.063 mm). (Fluid system: 11 volumes ethyl acetate to 1 volume methanol). A white solid was obtained. Glycosylated MA-BHET-α-Glc is shown as an example in FIG. 37.

Figure 38:
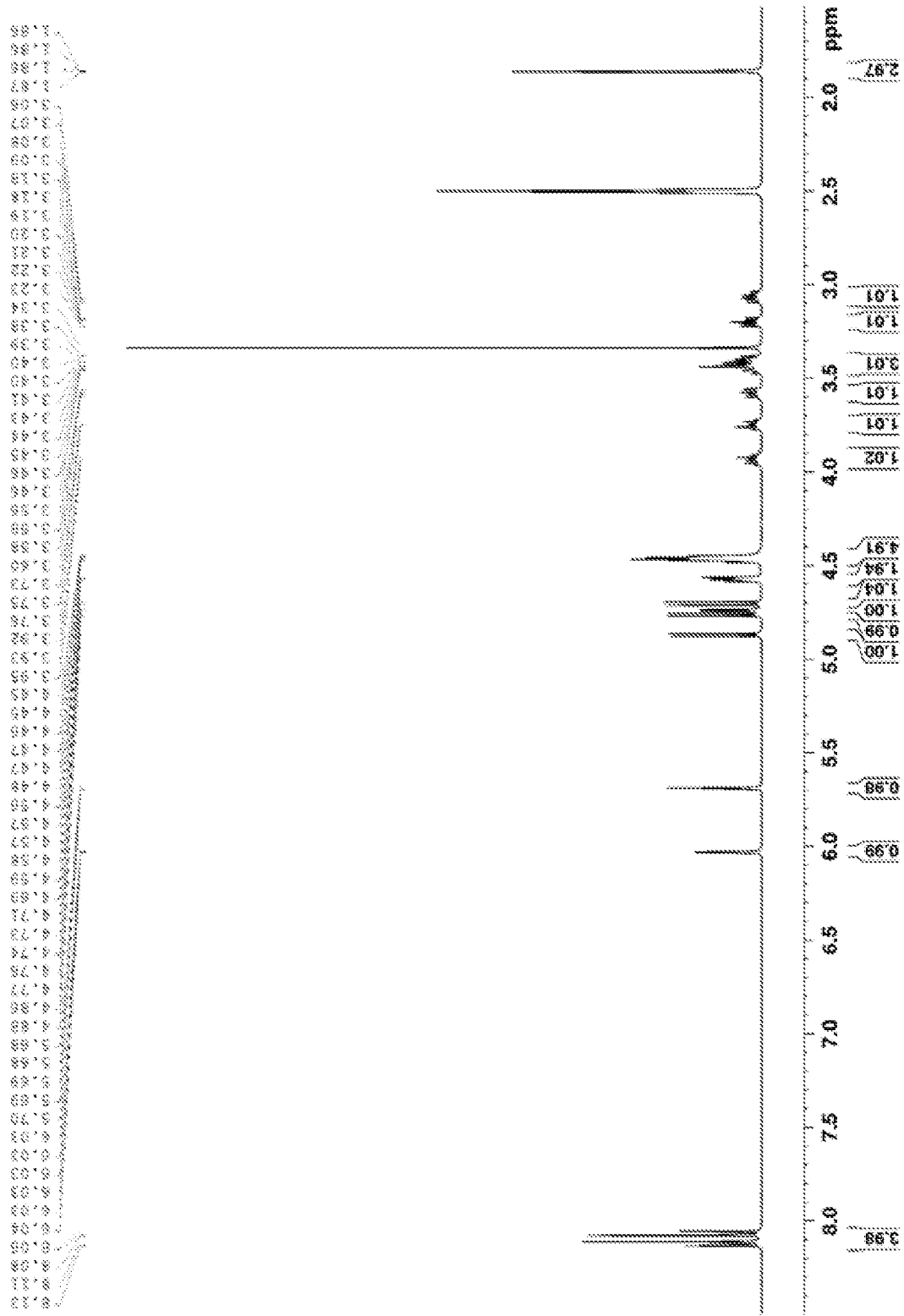
FIG. 38: $^1$H-NMR spectrum of glycosylated MA-BHET-α-Glc.
Figure 39:
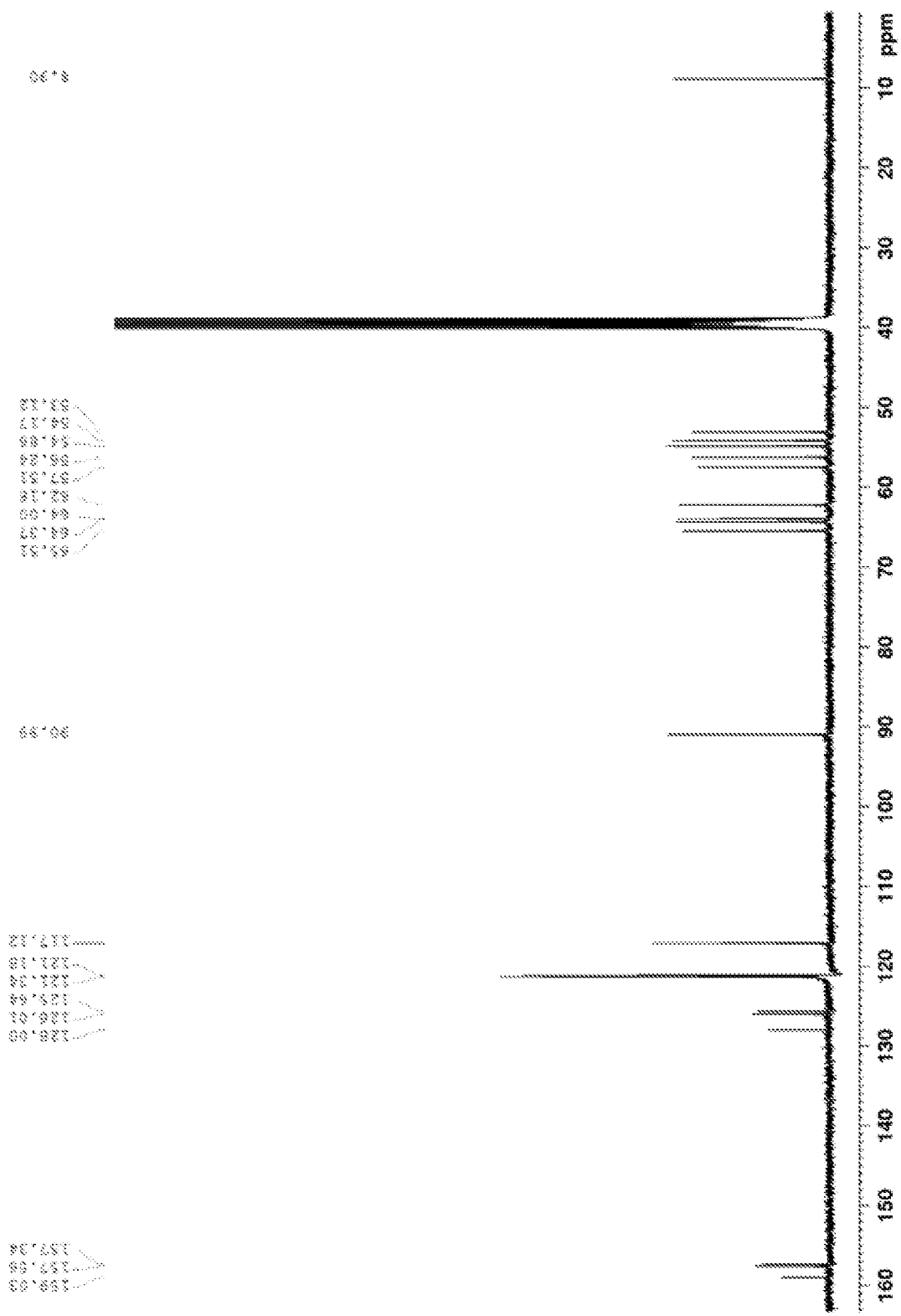
FIG. 39: $^{13}$C-NMR spectrum of glycosylated MA-BHET-α-Glc.

Further test results are shown in FIG. 38, FIG. 39 and the following tables.

NMR in deuterated $(CD_3)_2SO$.

TABLE 19

Signal assignment ¹H-NMR spectrum of glycosylated MA-BHET-α-Glc

| δ [ppm] | Assignment | Relative integral | Multiplicity | Coupling ratio J [Hz] |
|---|---|---|---|---|
| 8.12 | H-3", H-4", | 4H | Doublet | 8.72 |
| 8.07 | H-6", H-7" | | | |
| 6.03 | H-3""a | 1H | Doublet of Doublet of Doublet | 2.57 0.93 0.93 |
| 5.69 | H-3""b | 1H | Doublet of Doublet of Doublet | 3.21 1.59 1.59 |
| 4.88 | OH-1 | 1H | Doublet | 5.36 |
| 4.76 | OH-2 | 1H | Doublet | 4.88 |
| 4.74 | H-1 | 1H | Doublet | 3.68 |
| 4.70 | OH-3 | 1H | Doublet | 6.36 |
| 4.58-4.56 | H-2" | 2H | Multiplet | |
| 4.48-4.45 | H-2', H-1"", OH-4 | 4H | Multiplet | |
| 3.94 | H-1'a | 1H | Doublet from Triplet | 11.54 5.01 |
| 3.75 | H-1'b | 1H | Doublet from Triplet | 11.62 4.59 |
| 3.60-3.56 | H-6a | 1H | Multiplet | |
| 3.47-3.38 | H-6b, H-4, H-3 | 3H | Multiplet | |
| 3.23-3.18 | H-2 | 1H | Multiplet | |
| 3.09-3.04 | H-5 | 1H | Multiplet | |
| 3.41 | H-4"" | 1H | Doublet from Doublet | 9.72 3.76 |

TABLE 20

Signal assignment ¹³C-NMR spectrum of glycosylated MA-BHET-α-Glc

| δ [ppm] | Assignment |
|---|---|
| 159.03 | C-1"" |
| 157.56 | C-1", C-8" |
| 157.34 | |
| 128.00 | C-2"" |
| 126.01 | C-2", C-5" |
| 125.64 | |
| 121.34 | C-3", C-4", |
| 121.18 | C-6", C-7" |
| 117.12 | C-3"" |
| 90.99 | C-1 |
| 65.51 | C-3 |
| 64.37 | C-4 |
| 64.00 | C-2 |
| 62.18 | C-5 |
| 57.51 | C-1' |
| 56.24 | C-2' |
| 54.86 | C-2"' |
| 54.17 | C-1"' |
| 53.12 | C-6 |
| 8.90 | C-4"" |

(12) Production of Glycosylated MA₂-BHET-α-Glc 40 mg α-glucosylated BHET and 72 μl vinyl methyl acrylate are dissolved in 2 ml tert-butanol. Then 25 mg Novozymes 435 are added (immobilized on acrylic resin). At 50° C., the suspension is shaken for 30 h. The suspension is then centrifuged, the supernatant is decanted and constricted at the rotary evaporator. The residue is chromatographed on silica gel. (Fluid system: 11 volumes ethyl acetate to 1 volume methanol). A white solid was obtained.

Figure 40:
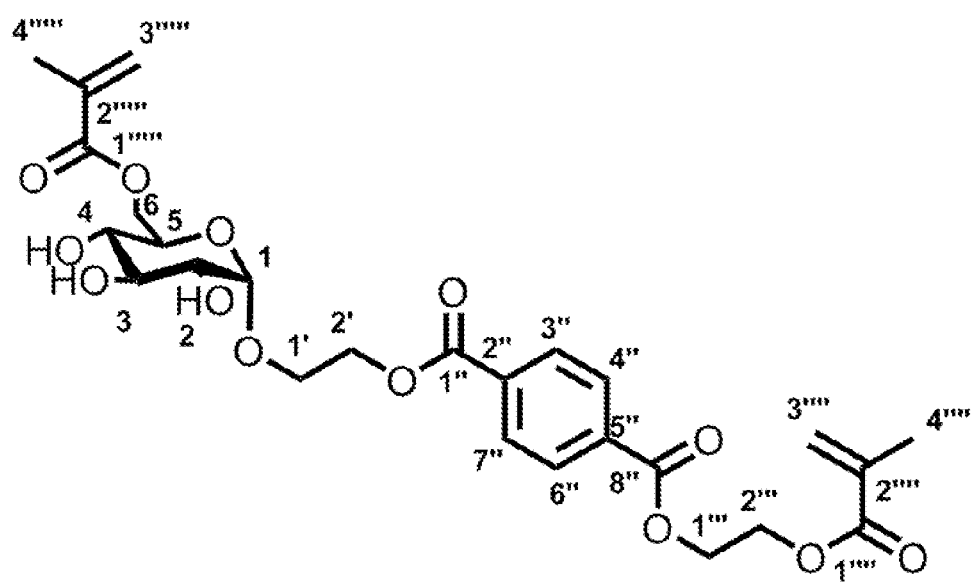
FIG. 40: Exemplary representation of the structure of glycosylated $MA_2$-BHET-α-Glc.
Figure 41:
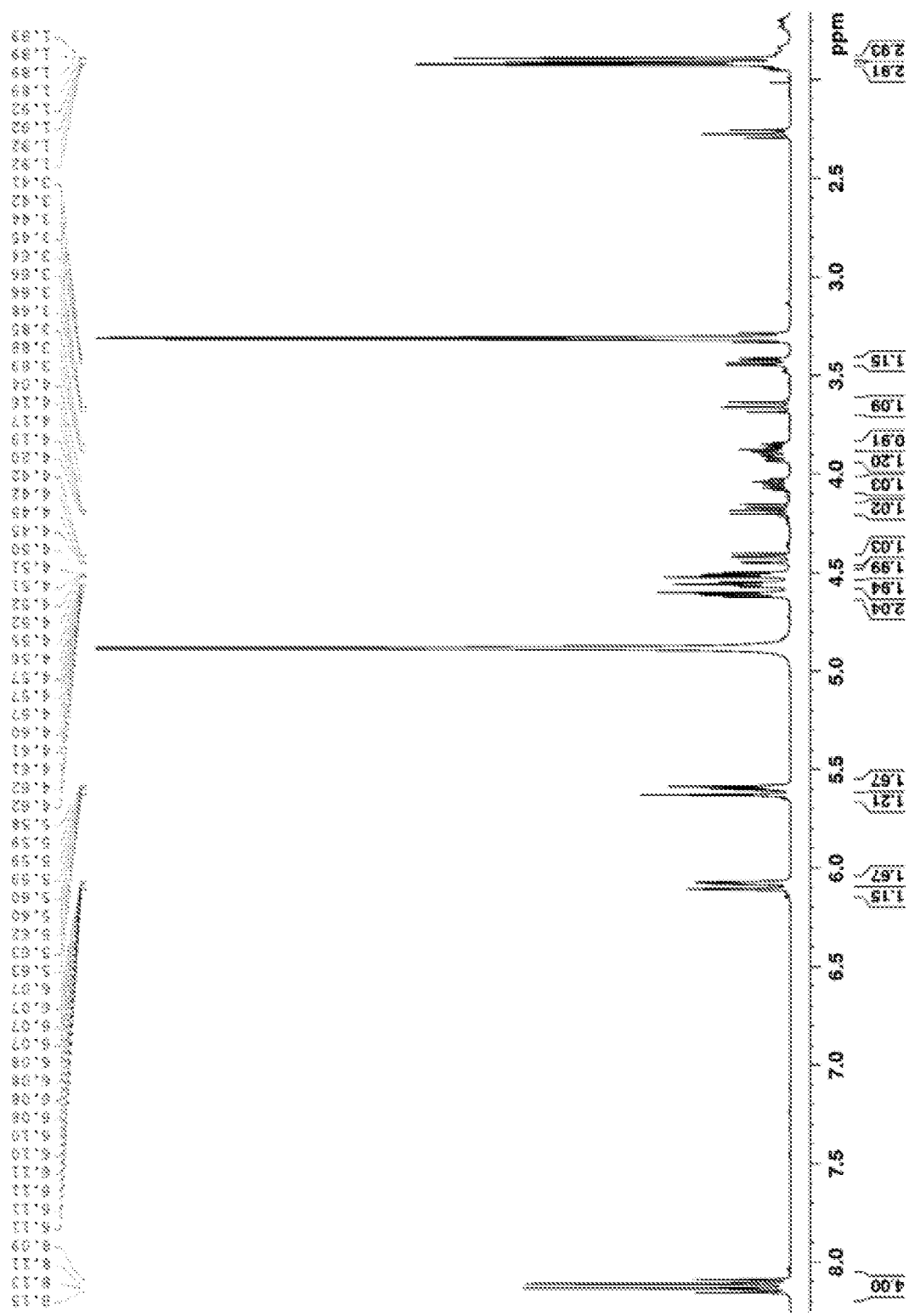
FIG. 41: $^1$H-NMR spectrum of glycosylated $MA_2$-BHET-α-Glc.
Figure 42:
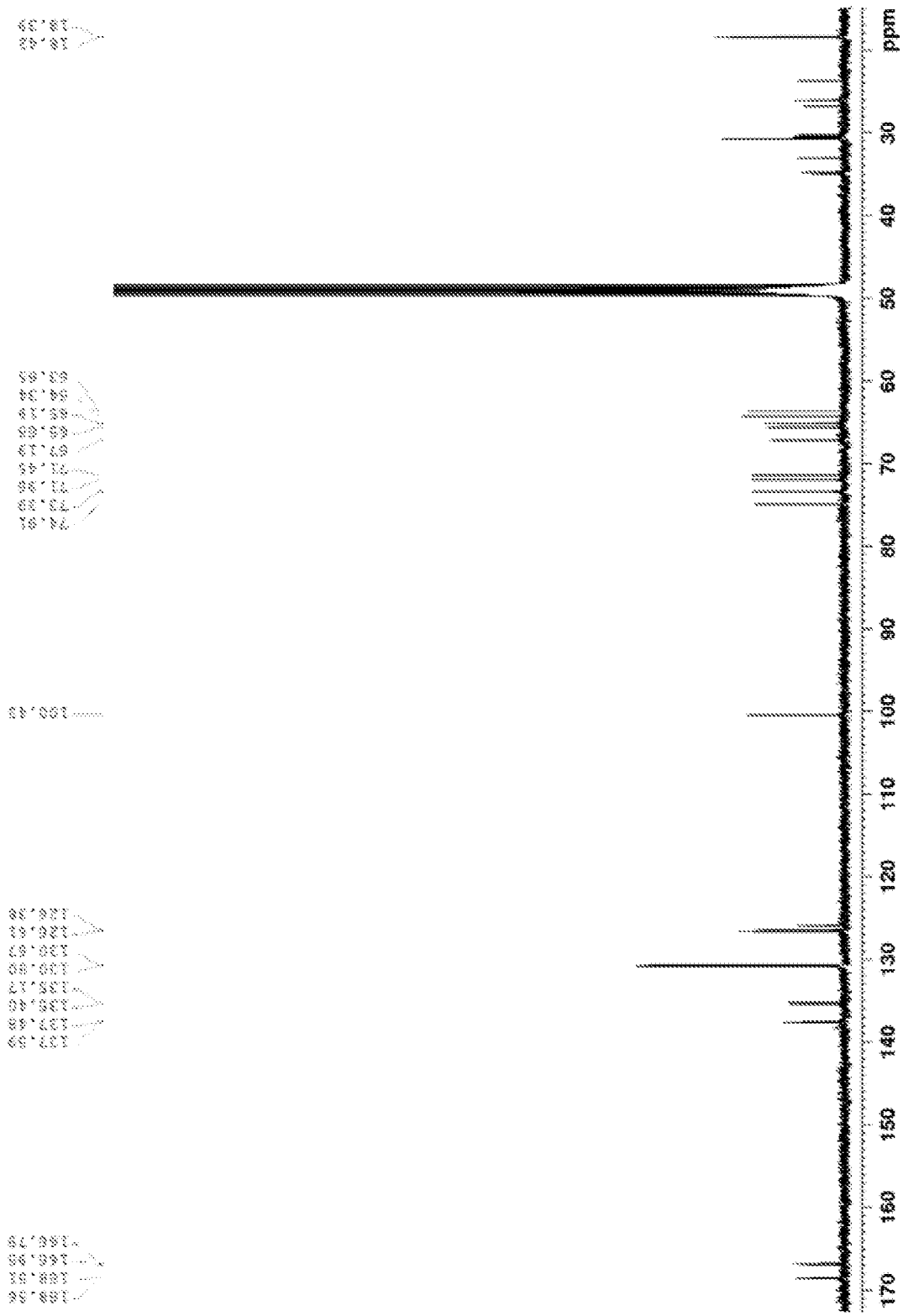
FIG. 42: $^{13}$C-NMR spectrum of glycosylated $MA_2$-BHET-α-Glc.

Glycosylated MA$_2$-BHET-α-Glc is shown as an example in FIG. 40. Further test results are shown in FIG. 41, FIG. 42 and the following tables.

NMR in CD$_3$OD.

TABLE 21

Signal assessment $^1$H-NMR spectrum of glycosylated MA$_2$-BHET-α-Glc

| δ [ppm] | Assignment | Relative integral | Multiplicity | Coupling ratio J [Hz] |
|---|---|---|---|---|
| 8.15-8.09 | H-3", H-4", H-6", H-7" | 4H | Multiplet | |
| 6.11 + 6.09 | H-3a'''' + H-3a''''' | 2H | Doublet from Triplet | 2.58 0.97 + 2.84 0.98 |
| 5.63 + 5.60 | H-3b'''' + H-3b''''' | 2H | Doublet from Triplet | 3.16 1.56 + 3.46 1.73 |
| ~4.88 | H-1 | 1H | below H$_2$O Peak | |
| 4.62-4.60 | H-1''' | 2H | Multiplet | |
| 4.57-4.55 | H-2' | 2H | Multiplet | |
| 4.52-4.50 | H-2''' | 2H | Multiplet | |
| 4.43 | H-6a | 1H | Doublet from Doublet | 11.80 2.12 |
| 4.18 | H-6b | 1H | Doublet from Doublet | 11.84 6.40 |
| 4.08-4.03 | H-1'a | 1H | Multiplet | |
| 3.94-3.83 | H-5, H-1'b | 2H | Multiplet | |
| 3.66 | H-3 | 1H | Doublet from Doublet | 9.54 8.98 |
| ~3.31 | H-2 | 1H | Under MeOH Peak | |
| 3.41 | H-4 | 1H | Doublet from Doublet | 9.72 3.76 |
| 1.90 + 1.89 | H-4'''' + H-4''''' | 2H | Doublet from Doublet | 1.58 1.02 + 1.50 1.02 |

TABLE 22

Signal assessment $^{13}$C-NMR spectrum of glycosylated MA$_2$-BHET-α-Glc

| δ [ppm] | Assignment |
|---|---|
| 168.56 | C-1''''' |
| 168.51 | C-1'''' |
| 166.95 | C-1", C-8" |
| 166.79 | |
| 137.59 | C-2''''' |
| 137.48 | C-2'''' |
| 135.40 | C-2", C-5" |
| 135.17 | |
| 130.80 | C-3", C-4", |
| 130.67 | C-6", C-7" |
| 126.61 | C-3'''', C-3''''' |
| 126.38 | |
| 100.43 | C-1 |
| 74.91 | C-3 |
| 73.39 | C-4 |
| 71.96 | C-2 |
| 71.45 | C-5 |
| 67.19 | C-1' |
| 65.66 | C-2' |
| 65.19 | C-6 |
| 64.34 | C-1''' |
| 63.65 | C-2''' |
| 18.42 18.39 | C-4'''', C-4''''' |

Figure 43:
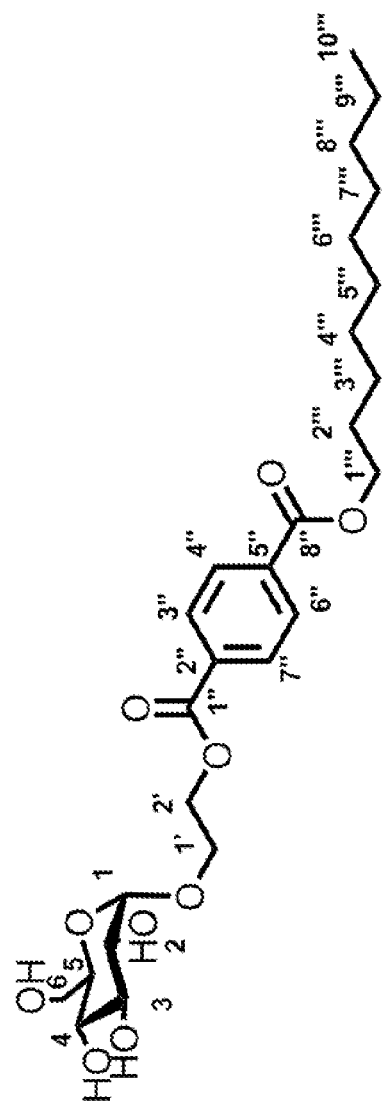
FIG. 43: Exemplary representation of the structure of glycosylated α-Glc-MHET decanol.
Figure 44:
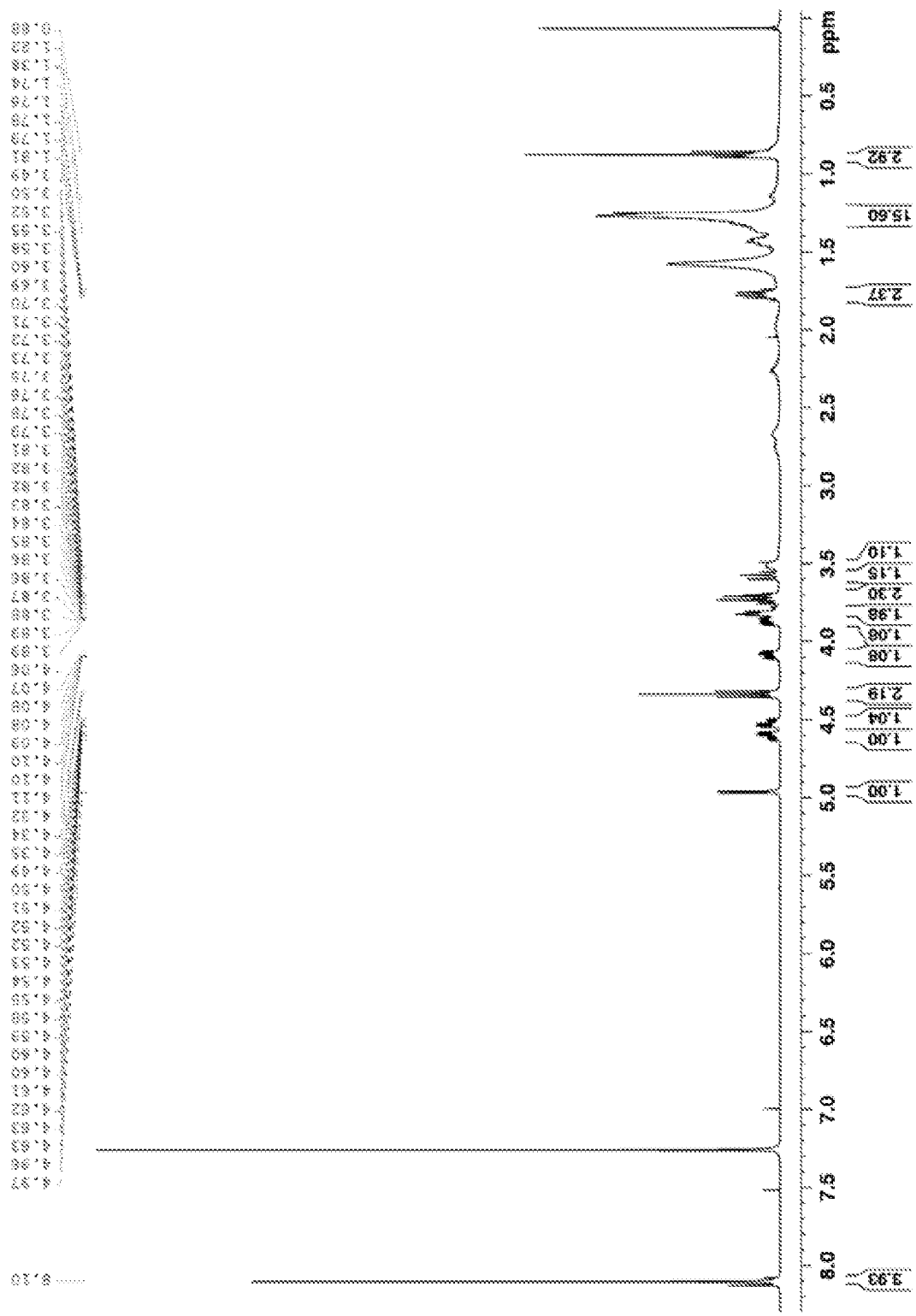
FIG. 44: $^1$H-NMR spectrum of glycosylated α-Glc-MHET decanol.
Figure 45:
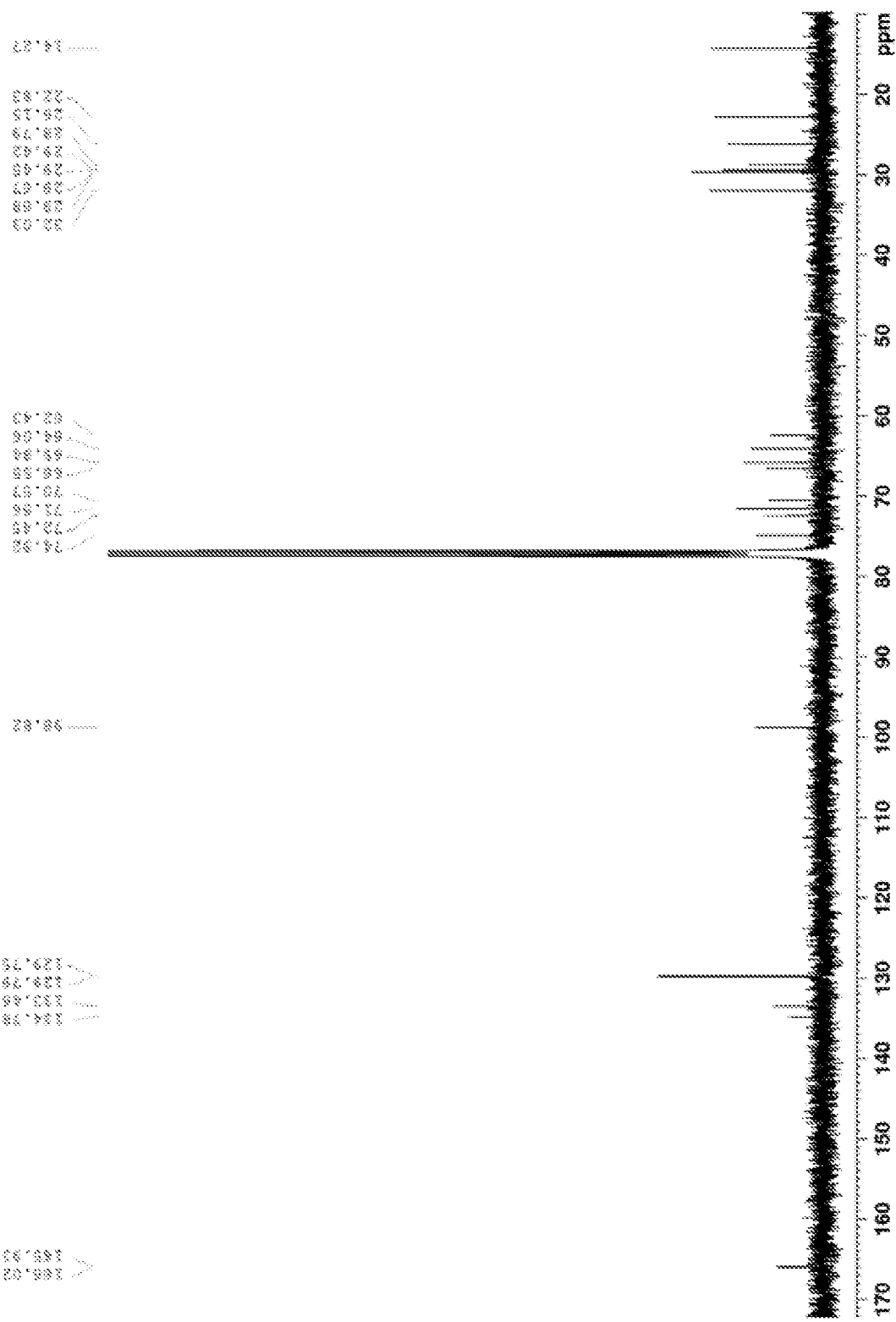
FIG. 45: $^{13}$C-NMR spectrum of glycosylated α-Glc-MHET decanol.

(13) Preparation of Glycosylated-Glc-MHET-Decanol 40 mg α-glucosylated BHET and 120 μl 1-decanol are added in 2 ml tert-butanol. Then 25 mg Novozymes 435 are added (immobilized on acrylic resin). At 50° C., the suspension is shaken for 24 h. The suspension is then centrifuged, the supernatant is decanted and constricted at the rotary evaporator. The residue is chromatographed on silica gel. (Fluid system: 11 volumes ethyl acetate to 1 volume methanol). A white solid was obtained. Glycosylated α-Glc-MHET-Decanol is shown as an example in FIG. 43. Further test results are shown in FIG. 44, FIG. 45 and the following tables.

NMR measured in CDCl$_3$.

TABLE 23

Signal assessment $^1$H-NMR spectrum of glycosylated α-Glc-MHET-Decanol

| δ [ppm] | Assignment | Relative integral | Multiplicity | Coupling ratio J [Hz] |
|---|---|---|---|---|
| 8.10 | H-3", H-4", H-6", H-7" | 4H | Singlet | |
| 4.96 | H-1 | 1H | Doublet | 3.88 |
| 4.61 | H-2"a | 1H | Doublet of Doublet of Doublet | 12.18 6.28 3.10 |
| 4.52 | H-2"b | 1H | Doublet of Doublet of Doublet | 12.17 6.31 3.05 |
| 4.34 | H-1''' | 2H | Triplet | 6.72 |
| 4.09 | H-1"a | 1H | Doublet of Doublet of Doublet | 11.70 6.24 3.04 |
| 3.87 | H-1"b | 1H | Doublet of Doublet of Doublet | 11.69 6.29 3.09 |
| 3.82 | H-6 | 2H | Doublet from Doublet | 5.88 4.00 |
| 3.73 | H-3 | 1H | Triplet | 9.18 |
| 3.71 | H-2 | 1H | Doublet from Doublet | 9.57 4.04 |
| 3.58 | H-4 | 1H | Triplet | 9.30 |
| 3.52-3.49 | H-5 | 1H | Multiplet | |

TABLE 23-continued

Signal assessment $^1$H-NMR spectrum of glycosylated
α-Glc-MHET-Decanol

| δ [ppm] | Assignment | Relative integral | Multiplicity | Coupling ratio J [Hz] |
|---|---|---|---|---|
| 1.78 | H-2''' | 2H | Doublet of the triplet | 14.46 6.98 |
| 1.46-1.41 | H-3''' | 2H | Multiplet | |
| 1.38-1.22 | H-(4, 5, 6, 7, 8, 9)''' | 12H | Multiplet | |
| 0.88 | H-10''' | 3H | Singlet | |

TABLE 24

Signal assessment $^{13}$C-NMR spectrum
of glycosylated α-Glc-MHET-Decanol

| δ [ppm] | Assignment |
|---|---|
| 166.02 | C-1'', C-8'' |
| 165.93 | |
| 134.78 | C-2'', C-5'' |
| 133.46 | |
| 129.79 | C-3'', C-4'', |
| 129.75 | C-6'', C-7'' |
| 98.82 | C-1 |
| 74.92 | C-3 |
| 72.45 | C-5 |
| 71.56 | C-2 |
| 70.57 | C-4 |
| 66.55 | C-1' |
| 65.84 | C-1''' |
| 64.06 | C-2' |
| 62.43 | C-6 |
| 32.03 | C-9''' |
| 29.68 29.67 | C-4''', C-5''', |
| 29.45 29.42 | C-6''', C-7''' |
| 28.79 | C-2''' |
| 26.15 | C-3''' |
| 22.83 | C-8''' |
| 14.27 | C-10''' |

Figure 46:
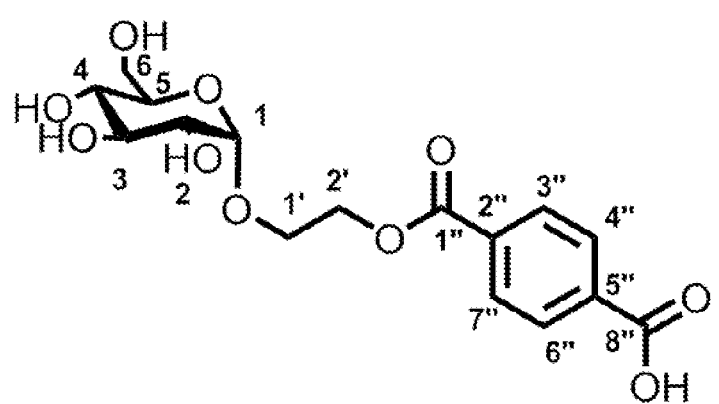
FIG. 46: Exemplary representation of the structure of α-glucosylated MHET.
Figure 47:
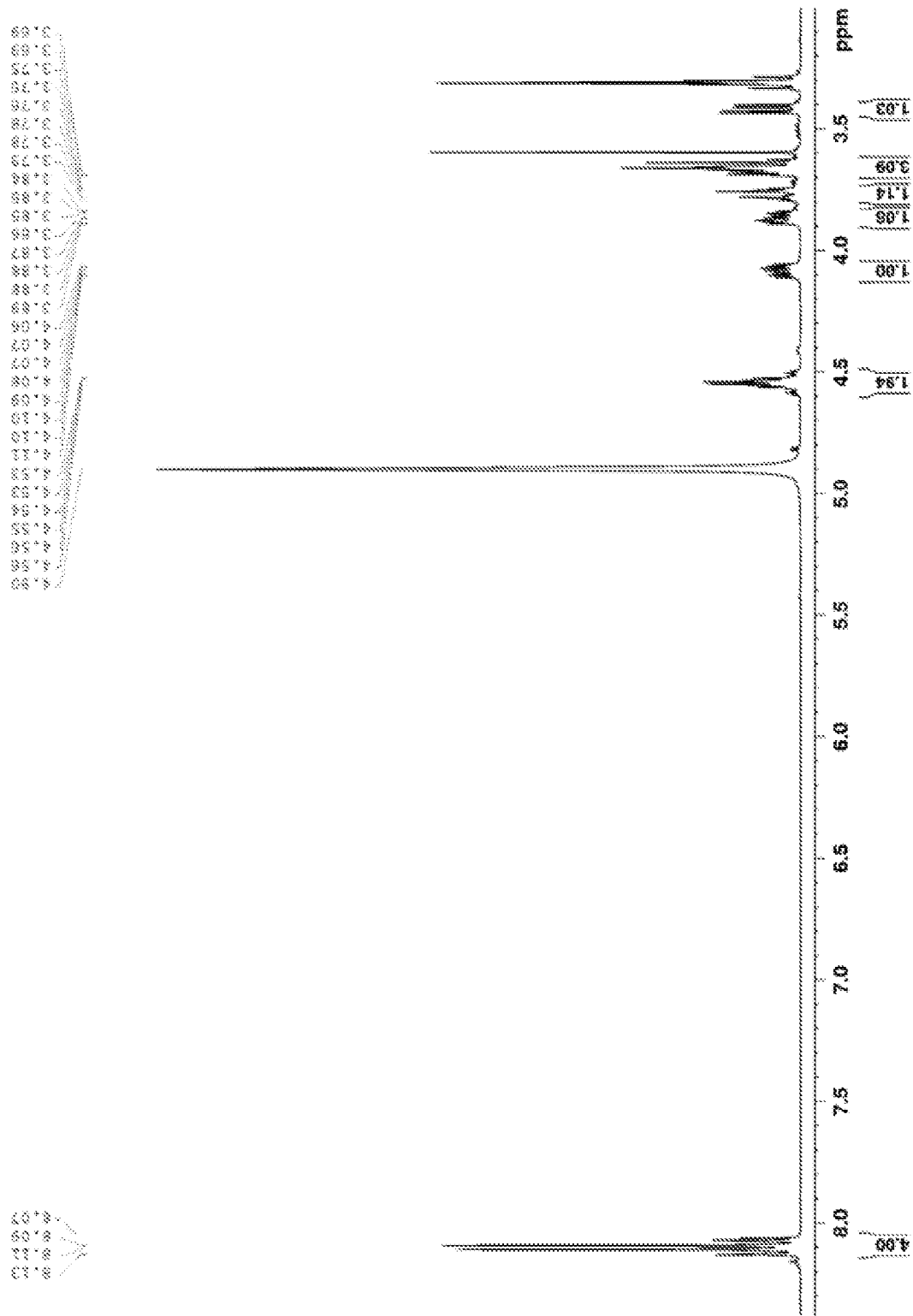
FIG. 47: $^1$H-NMR spectrum of α-glucosylated MHET.
Figure 48:
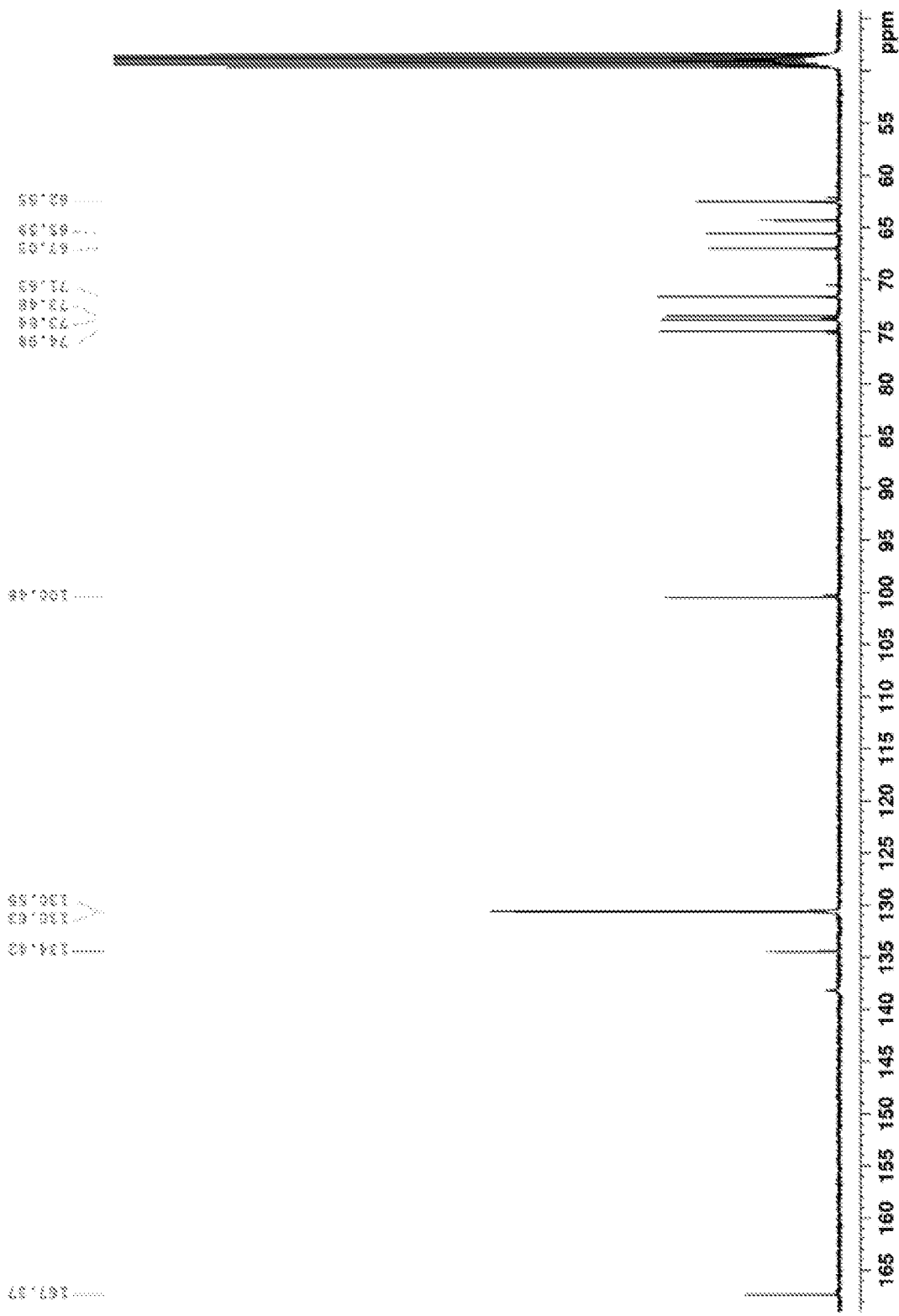
FIG. 48: $^{13}$C-NMR spectrum of α-glucosylated MHET.

(14) Alternative Production of α-Glucosylated MHET 40 mg α-glucosylated BHET are added to 2 ml 50 mM HEPES buffer pH 7.5. Then 25 mg Novozymes 435 (immobilised on acrylic resin) are added. At 50° C., the suspension is shaken for 24 h. The pH value of 7.5 of the solution is kept constant by adding 1 N NaOH solution. The suspension is then centrifuged, the supernatant is decanted and constricted at the rotary evaporator. The residue is chromatographed on silica gel. (Fluid system: 6 volumes ethyl acetate to 3 volumes isopropanol and 1 volume water). A white solid was obtained.

α-glucosylated MHET is shown as an example in FIG. 46. Further test results are shown in FIG. 47, FIG. 48 and the following tables.

NMR in CD$_3$OD.

TABLE 25

Signal assignment $^1$H-NMR spectrum of α-glucosylated MHET

| δ [ppm] | Assignment | Relative integral | Multiplicity | Coupling ratio J [Hz] |
|---|---|---|---|---|
| 8.12 | H-3'', H-4'', | 4H | Doublet | 8.60 8.72 |
| 8.08 | H-6'', H-7'' | | | |
| ~4.9 | H-1 | 1H | Below H$_2$O Peak | |
| 4.56-4.53 | H-2' | 2H | Multiplet | |

TABLE 25-continued

Signal assignment $^1$H-NMR spectrum of α-glucosylated MHET

| δ [ppm] | Assignment | Relative integral | Multiplicity | Coupling ratio J [Hz] |
|---|---|---|---|---|
| 4.08 | H-1'a | 1H | Doublet of Doublet of Doublet | 11.64 6.28 3.52 |
| 3.87 | H-1'b | 1H | Doublet of Doublet of Doublet | 11.65 5.62 3.51 |
| 3.79-3.75 | H-6'a | 1H | Multiplet | |
| 3.69-3.63 | H-3, H-4, H-6'b | 1H | Multiplet | |
| 3.42 | H-2 | 1H | Doublet from Doublet | 9.70 3.74 |
| ~3.31 | H-5 | 1H | Under MeOH Peak | |

TABLE 26

Signal assignment $^{13}$C-NMR spectrum
of α-glucosylated MHET

| δ [ppm] | Assignment |
|---|---|
| 167.37 | C-1'', C-8'' |
| 134.42 | C-2'', C-5'' |
| 130.63 | C-3'', C-4'', |
| 130.55 | C-6'', C-7'' |
| 100.48 | C-1 |
| 74.94 | C-3 |
| 73.84 | C-4 |
| 73.48 | C-2 |
| 71.63 | C-5 |
| 67.03 | C-1' |
| 65.59 | C-2' |
| 62.55 | C-6 |

Figure 49:
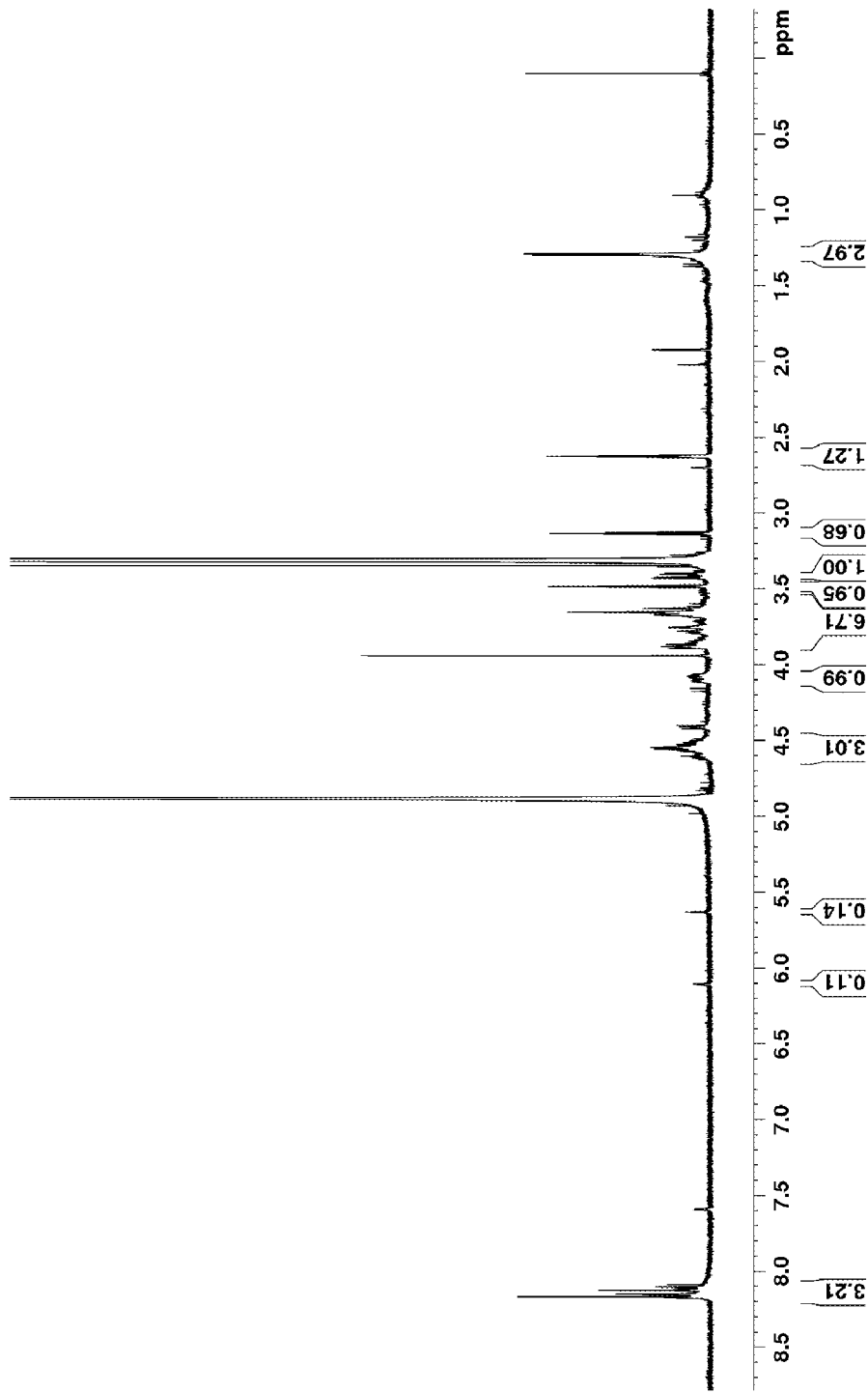
FIG. 49: Detection of the polymer; the $^1$H-NMR spectrum of the polymer is shown.

(15) Polymerisation of MA-BHET-α-Glc 1 ml water and 50 mg MA-BHET-α-Glc and 1 mg K$_2$O$_8$S$_2$ are added to 2 ml DMSO. This solution is rinsed with nitrogen for 2 hours. Then the reaction is closed and shaken at 50° C. for 12 hours. The solvents were removed by freeze-drying, then part of the residue was dissolved overnight in deuterated methanol at 50° C. and a $^1$H-NMR 400 MHz measured. Test results are shown in FIG. 49.

INDUSTRIAL APPLICABILITY

This invention can be used commercially in many ways. For example, the further use of degradation products from the hydrolysis of PET in the form of biohybrid polymers is made possible. According to the invention, biohybrid polymers have an increased biocompatibility, compostability and/or enable improved adhesion of cultured cells to surfaces.

Key to Figures

Figure 2:
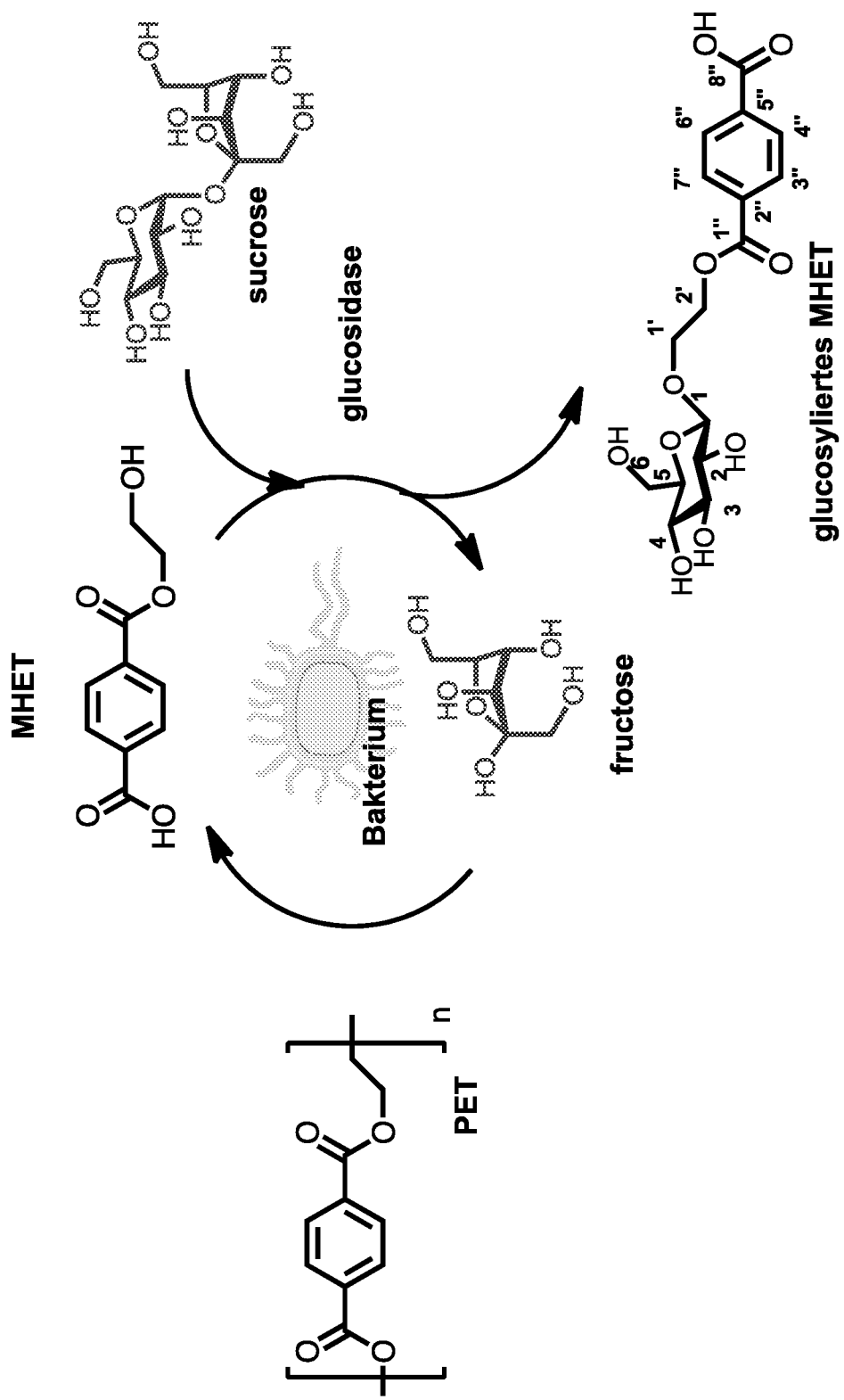
FIG. 2: Exemplary representation of the MHET obtained from PET using microorganisms.

| FIG. 2: | |
|---|---|
| Bakterium glucosyliertes MHET | Bacterium glycosylated MHET |

Figure 3:
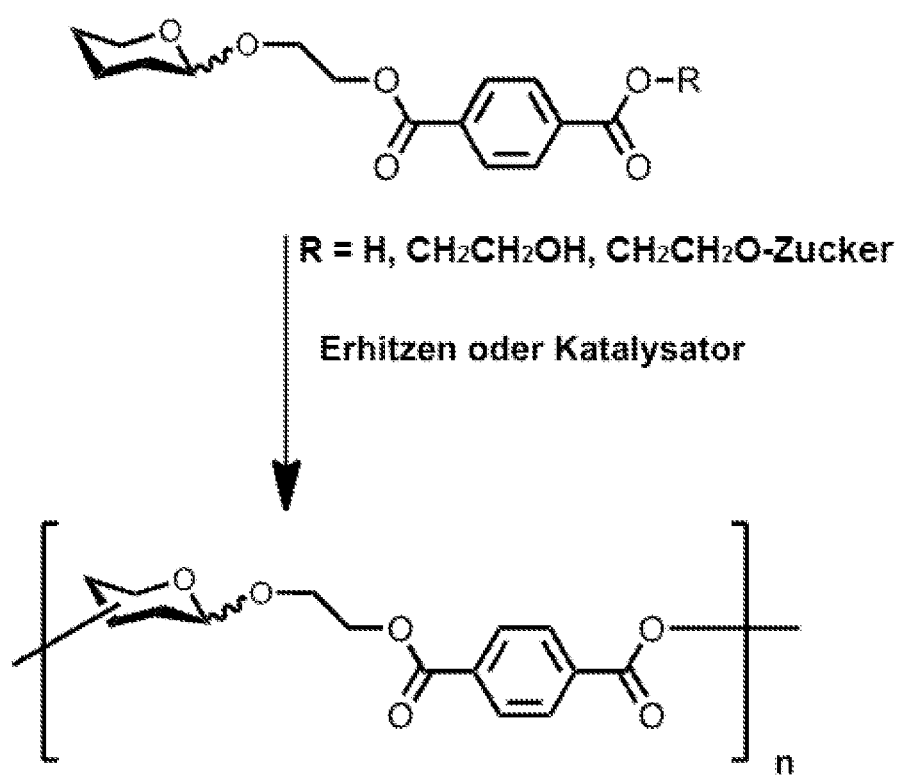
FIG. 3: A biohybrid polymer made of glycosylated MHET.

| FIG. 3: | |
|---|---|
| R = H, CH$_2$CH$_2$OH, CH$_2$CH$_2$O-Zucker | R = H, CH$_2$CH$_2$OH, CH$_2$CH$_2$O-Sugar |
| Erhitzen oder Katalysator | Heating or catalyst |

| FIG. 4: | |
|---|---|
| Biohybrid-Polymere | biohybrid polymers |
| Feinchemikalien | fine chemicals |
| Wirkstoffe | active substance |

Figure 6:
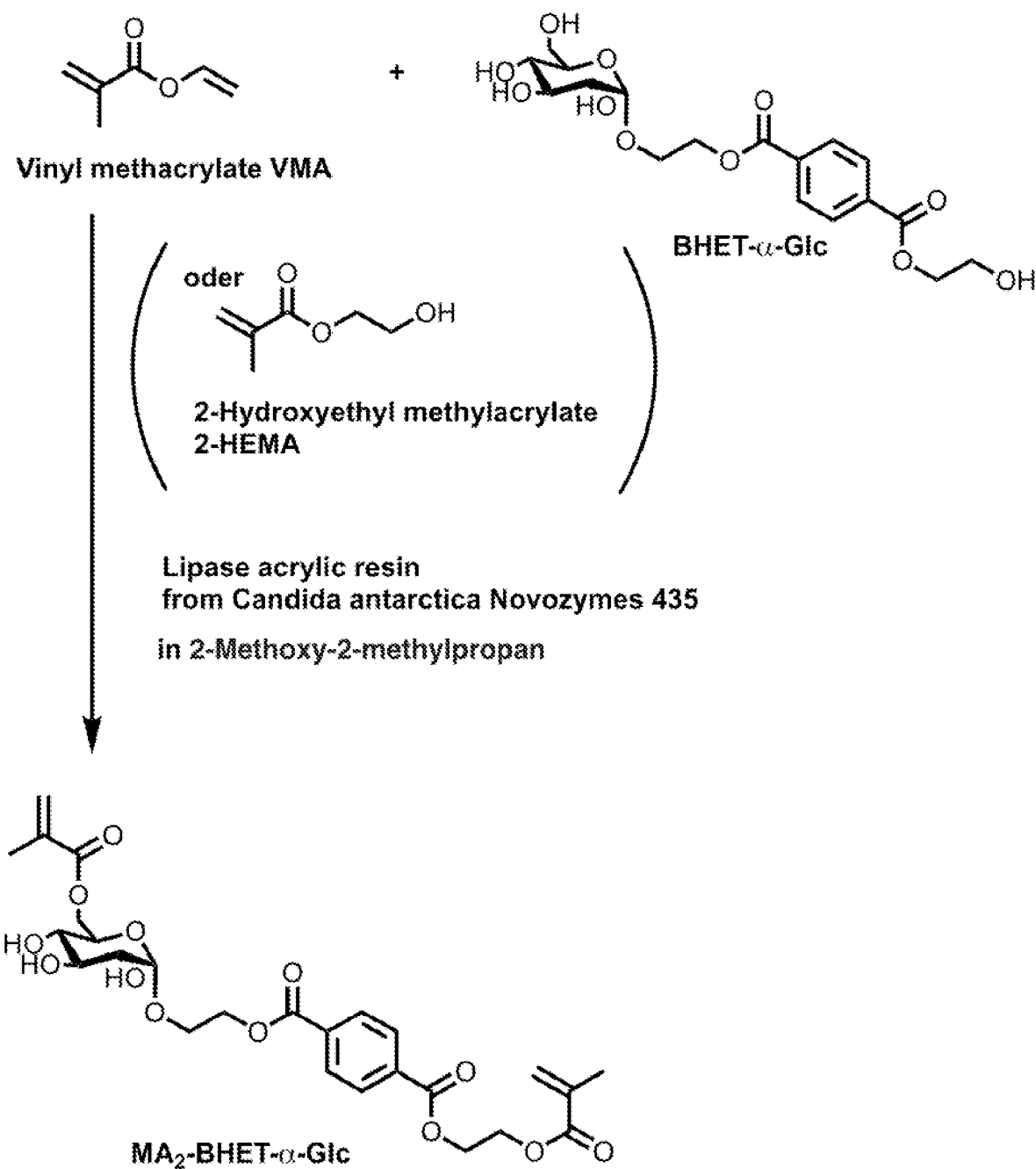
FIG. 6: Glycosylated MHET and glycosylated bis(2-hydroxyethyl) terephthalic acid can be combined with methacrylate. For this purpose, methacrylate is esterified enzymatically with one or more alcohol functions of MHET or bis(2-hydroxyethyl) terephthalic acid.

| FIG. 6: | |
|---|---|
| oder | or |

Figure 7:
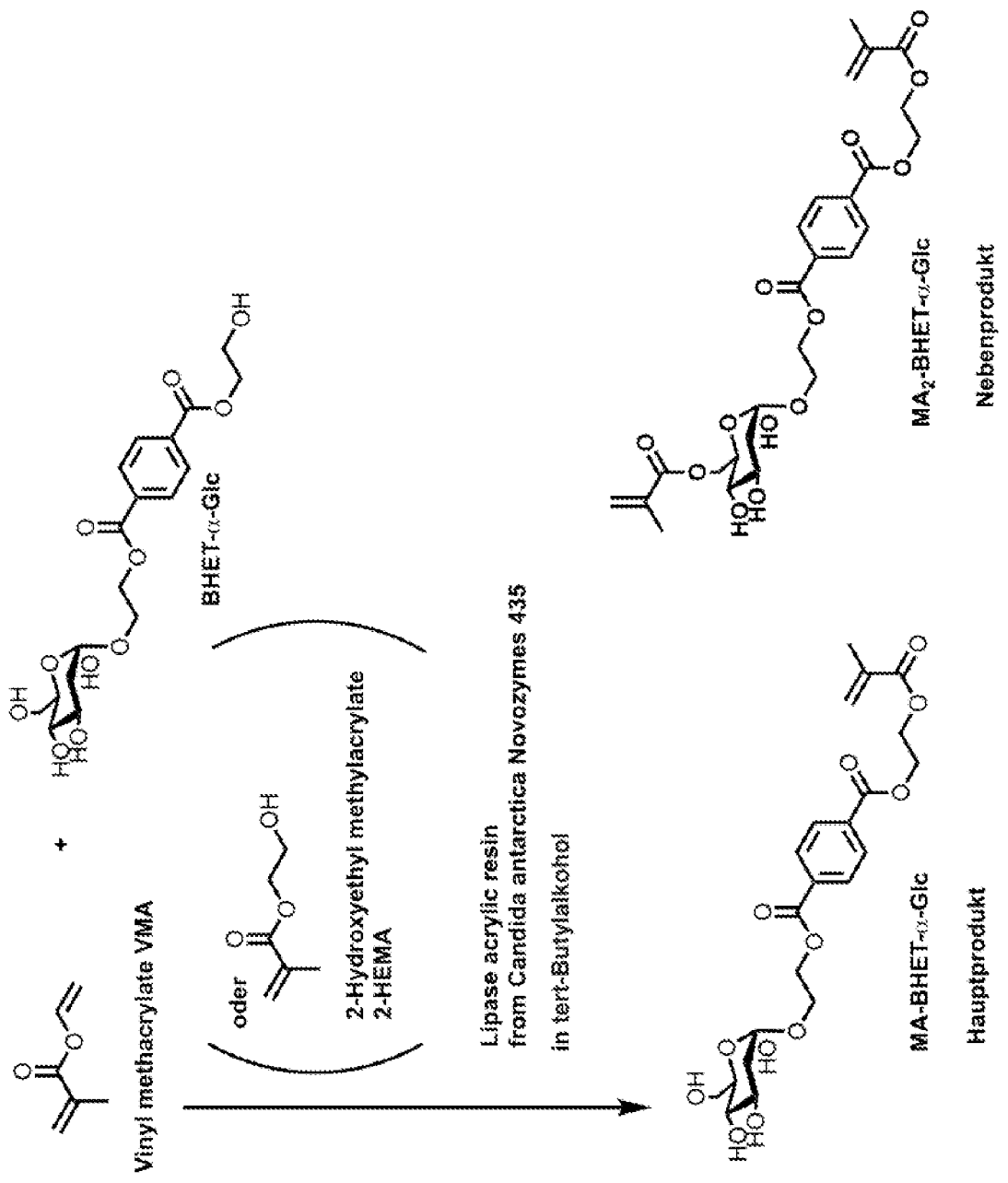
FIG. 7: Glycosylated MHET and glycosylated bis(2-hydroxyethyl) terephthalic acid can be combined with methacrylate. For this purpose, methacrylate is esterified enzymatically with one or more alcohol functions of MHET or bis(2-hydroxyethyl) terephthalic acid.

| FIG. 7: | |
|---|---|
| oder | or |
| tert-Butylalkohol | tert-Butanol |
| Houptprodukt | main product |
| Nebenprodukt | byproduct |

| FIG. 9: | |
|---|---|
| Verzweigtes MA-BHET-α-Glc Polymer | branched MA-BHET-α-Glc polymer |

The invention claimed is:

1. A Compound comprising:
   i) glycosylated mono(2-hydroxyethyl) terephthalic acid (MHET) or glycosylated bis(2-hydroxyethyl) terephthalic acid (BHET); wherein the MHET or BHET and a saccharide are chemically bonded to each other via a glycosidic bond; or
   ii) mono(2-hydroxyethyl) terephthalic acid (MHET) or bis(2-hydroxyethyl) terephthalic acid chemically bonded to a saccharide; wherein the MHET or BHET and the saccharide are chemically bonded to each other via a glycosidic bond.

2. The compound according to claim 1, wherein the saccharide is a monosaccharide or disaccharide, wherein the monosaccharide or disaccharide is optionally selected from a group consisting of hexoses and pentoses, or wherein the monosaccharide or disaccharide is optionally selected from α-glucose, β-glucose, α-fructose, β-fructose, α-galactose and β-galactose, α-mannose and β-mannose, xylose, N-acetylglucosamine, glucosamine and glucuronic acid.

3. The compound according to claim 1, wherein the compound is obtained by enzymatic glycosylation of MHET or BHET, wherein the enzymatic glycosylation is optionally catalysed by a glucosidase, a galactosidase, or a fructosidase, and wherein the glucosidase is optionally an α-glucosidase or a β-glucosidase, and/or wherein the MHET or BHET is optionally obtained by bacterial degradation or enzymatic degradation from polyethylene terephthalate (PET), and wherein the MHET or BHET is optionally formed by bacterial degradation or enzymatic degradation from polyethylene terephthalate (PET), and wherein the enzymatic degradation of PET is optionally catalysed by a hydrolase, and wherein the hydrolase is optionally PETase from *Idionella sakaiensis*, and/or wherein the hydrolase optionally comprises the amino acid sequence shown in SEQ ID NO: 1, and/or wherein the enzyme for the enzymatic glycosylation of MHET or BHET and the enzyme for the enzymatic degradation of PET are optionally used together, wherein a microorganism containing the enzyme for enzymatic glycosylation and the enzyme for enzymatic degradation of PET is optionally used.

4. The compound according to claim 1, consisting of MHET or BHET chemically bonded to a saccharide via a glycosidic bond, and wherein the compound has one of the following structures (a) or (b):

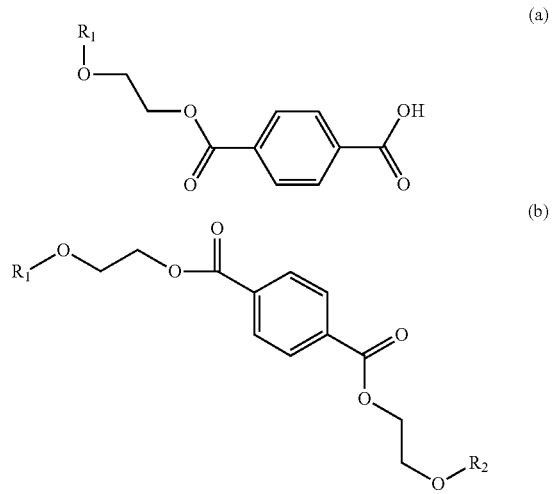

wherein $R_1$ comprises a saccharide bound via a glycosidic bond, and $R_2$ comprises a saccharide bound via a glycosidic bond or is H.

5. The compound according to claim 1, wherein the compound further comprises at least one methacrylic residue, wherein the compound optionally has the following structure:

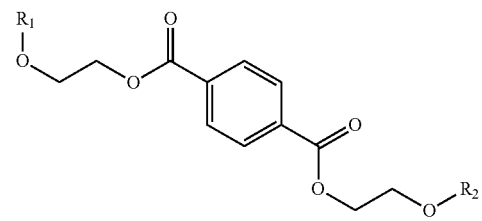

wherein $R_1$ comprises a saccharide bound via a glycosidic bond and $R_2$ comprises a methacrylic residue, wherein the compound optionally has the following structure:

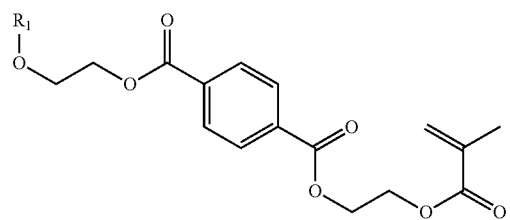

or, optionally, has the following structure:

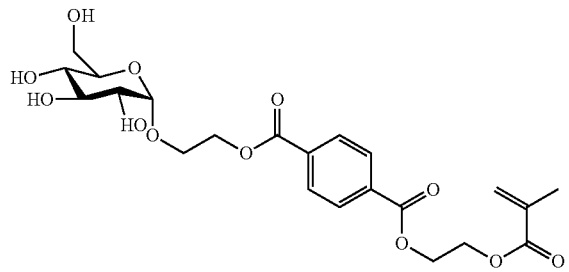

or, optionally, has the following structure:

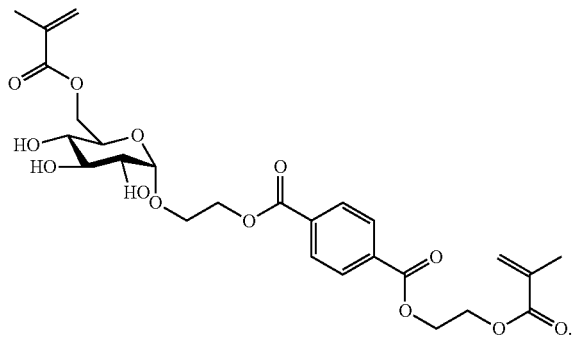

6. The compound according to claim 1, wherein the compound further comprises a lipophilic side chain wherein the compound optionally has the following structure:

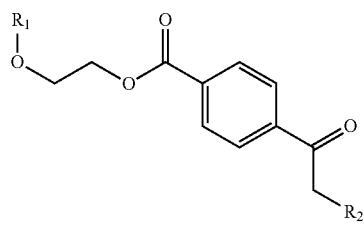

wherein $R_1$ comprises a saccharide bound via a glycosidic bond and $R_2$ comprises a lipophilic side chain, wherein $R_2$ is optionally a saturated or unsaturated aliphatic $C_5$ to $C_{20}$ hydrocarbon side chain, or wherein the compound is optionally selected from a compound having the following structure (a) to (j):

(a)
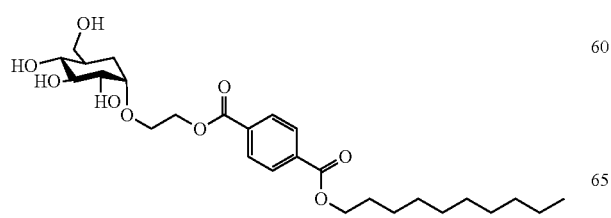

(b)
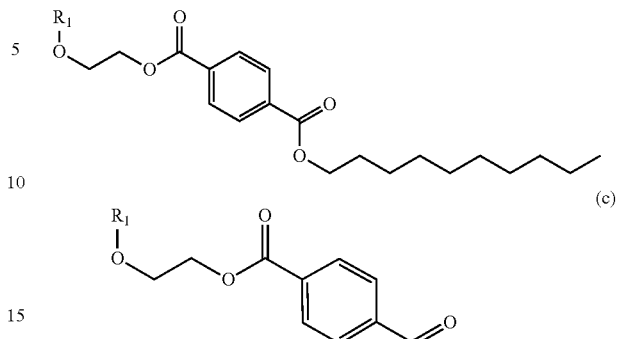

(c)
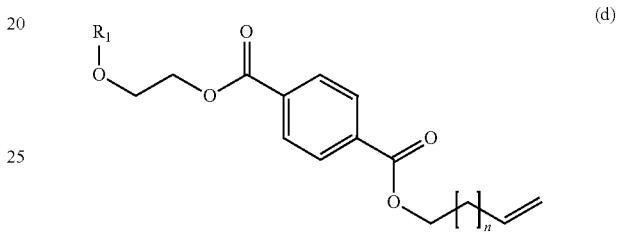

(d)
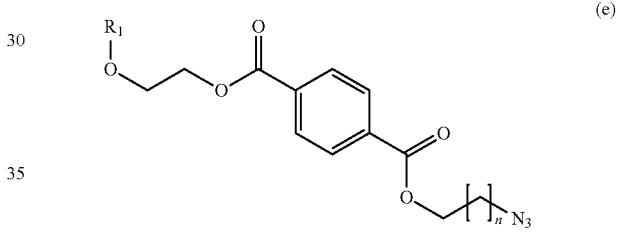

(e)
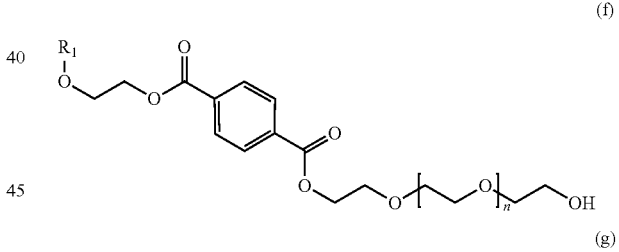

(f)
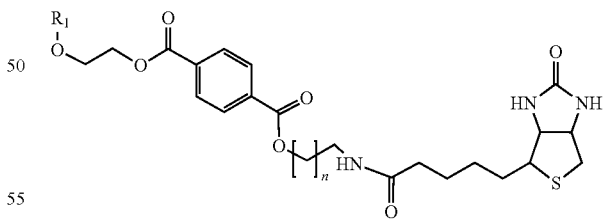

(g)
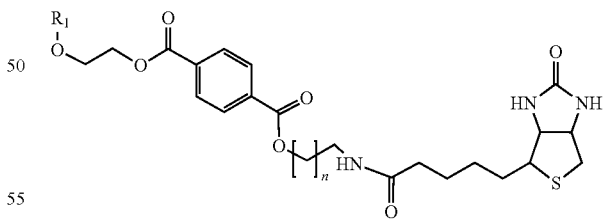

(h)
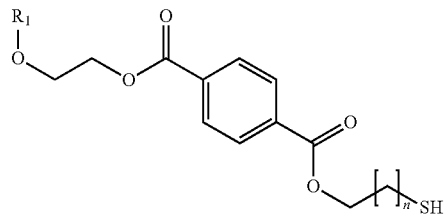

-continued

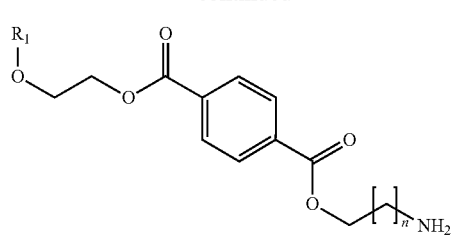

(i)

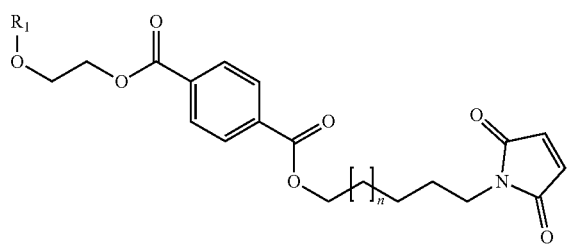

(j)

wherein n is 1, 2, 3, 4, 5, 6, 7, 8, 9, 10, 11, 12, 13, 14, 15, 16, 17, 18, 19 or 20.

7. The compound according to claim 1, wherein the saccharide chemically bonded to MHET or BHET via a glycosidic bond is methacrylated.

8. A polymer of a compound according to claim 1, said polymer optionally being a biohybrid polymer.

9. A method for preparing a compound of claim 1, said method comprising the step of enzymatic glycosylation of mono(2-hydroxyethyl) terephthalic acid (MHET) or bis(2-hydroxyethyl) terephthalic acid (BHET), wherein in the step of enzymatic glycosylation the MHET or BHET and a saccharide are chemically bonded together via a glycosidic bond, wherein the saccharide is optionally a monosaccharide or disaccharide, wherein the monosaccharide or disaccharide is optionally selected from a group containing hexoses and pentoses, and wherein the monosaccharide or disaccharide is optionally selected from α-glucose, β-glucose, α-fructose, β-fructose, α-galactose and β-galactose, α-mannose and β-mannose, xylose, N-acetylglucosamine, glucosamine and glucuronic acid.

10. The method according to claim 9, wherein the enzymatic glycosylation is catalysed by a glucosidase, a galactosidase or a fructosidase, wherein the glucosidase is optionally an α-glucosidase or a β-glucosidase.

11. The method according to claim 9, wherein the MHET or BHET is obtainable by bacterial degradation or enzymatic degradation from polyethylene terephthalate (PET), wherein the enzymatic degradation of PET is optionally catalysed by a hydrolase, wherein the hydrolase is optionally PETase from *Idionella sakaiensis*, and/or wherein the hydrolase optionally comprises the amino acid sequence shown in SEQ ID NO: 1, wherein the enzyme for the enzymatic glycosylation of MHET or BHET and the enzyme for the enzymatic degradation of PET are optionally used together, and wherein a microorganism containing the enzyme for enzymatic glycosylation and the enzyme for enzymatic degradation of PET is optionally used.

12. The method according to claim 9, wherein a methacrylic residue is chemically bonded to the glycosylated MHET or BHET in a further step, wherein the methacrylic residue is optionally chemically bonded to the glycosylated MHET or BHET by addition of vinylmethyl methacrylate, or wherein in a further step a lipophilic side chain, is chemically bonded to the glycosylated MHET or BHET, wherein the lipophilic side chain is optionally a saturated or unsaturated $C_5$ to $C_{20}$ hydrocarbon side chain, wherein the lipophilic side chain is optionally bound by the addition of decanol.

13. The method according to claim 9, wherein a polymerisation step follows the enzymatic glycosylation step.

14. A polymer obtainable by the method according to claim 9, wherein a polymerisation step follows the enzymatic glycosylation step, wherein the polymer is optionally a biohybrid polymer.

15. The compound according to claim 1, wherein the saccharide is a monosaccharide or disaccharide, wherein the monosaccharide or disaccharide is optionally selected from a group consisting of hexoses and pentoses, or wherein the monosaccharide or disaccharide is optionally selected from α-glucose, β-glucose, α-fructose, β-fructose, α-galactose and β-galactose, α-mannose and β-mannose, xylose, N-acetylglucosamine, glucosamine and glucuronic acid.

16. The compound according to claim 1, wherein the compound is obtained by enzymatic glycosylation of MHET or BHET, wherein the enzymatic glycosylation is optionally catalysed by a glucosidase, a galactosidase or a fructosidase, and wherein the glucosidase is optionally an α-glucosidase or a β-glucosidase, and/or wherein the MHET or BHET is optionally obtained by bacterial degradation or enzymatic degradation from polyethylene terephthalate (PET), and wherein the MHET or BHET is optionally formed by bacterial degradation or enzymatic degradation from polyethylene terephthalate (PET), and wherein the enzymatic degradation of PET is optionally catalysed by a hydrolase, and wherein the hydrolase is optionally PETase from *Idionella sakaiensis*, and/or wherein the hydrolase optionally comprises the amino acid sequence shown in SEQ ID NO: 1, and/or wherein the enzyme for the enzymatic glycosylation of MHET or BHET and the enzyme for the enzymatic degradation of PET are optionally used together, wherein a microorganism containing the enzyme for enzymatic glycosylation and the enzyme for enzymatic degradation of PET is optionally used.

* * * * *

SEQUENCE LISTING

<160> NUMBER OF SEQ ID NOS: 1

<210> SEQ ID NO 1
<211> LENGTH: 290
<212> TYPE: PRT
<213> ORGANISM: Ideonella sakaiensis
<220> FEATURE:
<223> OTHER INFORMATION: PETase

<400> SEQUENCE: 1

```
Met Asn Phe Pro Arg Ala Ser Arg Leu Met Gln Ala Ala Val Leu Gly
1               5                   10                  15

Gly Leu Met Ala Val Ser Ala Ala Thr Ala Gln Thr Asn Pro Tyr
                20                  25                  30

Ala Arg Gly Pro Asn Pro Thr Ala Ala Ser Leu Glu Ala Ser Ala Gly
            35                  40                  45

Pro Phe Thr Val Arg Ser Phe Thr Val Ser Arg Pro Ser Gly Tyr Gly
50                  55                  60

Ala Gly Thr Val Tyr Tyr Pro Thr Asn Ala Gly Gly Thr Val Gly Ala
65                  70                  75                  80

Ile Ala Ile Val Pro Gly Tyr Thr Ala Arg Gln Ser Ser Ile Lys Trp
                85                  90                  95

Trp Gly Pro Arg Leu Ala Ser His Gly Phe Val Val Ile Thr Ile Asp
            100                 105                 110

Thr Asn Ser Thr Leu Asp Gln Pro Ser Ser Arg Ser Ser Gln Gln Met
        115                 120                 125

Ala Ala Leu Arg Gln Val Ala Ser Leu Asn Gly Thr Ser Ser Ser Pro
    130                 135                 140

Ile Tyr Gly Lys Val Asp Thr Ala Arg Met Gly Val Met Gly Trp Ser
145                 150                 155                 160

Met Gly Gly Gly Gly Ser Leu Ile Ser Ala Ala Asn Asn Pro Ser Leu
                165                 170                 175

Lys Ala Ala Ala Pro Gln Ala Pro Trp Asp Ser Ser Thr Asn Phe Ser
            180                 185                 190

Ser Val Thr Val Pro Thr Leu Ile Phe Ala Cys Glu Asn Asp Ser Ile
        195                 200                 205

Ala Pro Val Asn Ser Ser Ala Leu Pro Ile Tyr Asp Ser Met Ser Arg
    210                 215                 220

Asn Ala Lys Gln Phe Leu Glu Ile Asn Gly Gly Ser His Ser Cys Ala
225                 230                 235                 240

Asn Ser Gly Asn Ser Asn Gln Ala Leu Ile Gly Lys Lys Gly Val Ala
                245                 250                 255
```

```
Trp Met Lys Arg Phe Met Asp Asn Asp Thr Arg Tyr Ser Thr Phe Ala
            260                 265                 270
Cys Glu Asn Pro Asn Ser Thr Arg Val Ser Asp Phe Arg Thr Ala Asn
            275                 280                 285
Cys Ser
    290
```